US010245273B2

(12) United States Patent
Salameh et al.

(10) Patent No.: US 10,245,273 B2
(45) Date of Patent: Apr. 2, 2019

(54) ORAL PHARMACEUTICAL PRODUCTS AND METHODS OF USE COMBINING TESTOSTERONE ESTERS WITH HYPOLIPIDEMIC AGENTS

(71) Applicant: Clarus Therapeutics, Inc., Northbrook, IL (US)

(72) Inventors: Wael Salameh, Northbrook, IL (US); Panayiotis Constantinides, Northbrook, IL (US)

(73) Assignee: Clarus Therapeutics, Inc., Northbrook, IL (US)

( * ) Notice: Subject to any disclaimer, the term of this patent is extended or adjusted under 35 U.S.C. 154(b) by 0 days.

(21) Appl. No.: 15/107,492

(22) PCT Filed: Dec. 24, 2014

(86) PCT No.: PCT/US2014/072332
§ 371 (c)(1),
(2) Date: Jun. 23, 2016

(87) PCT Pub. No.: WO2015/100406
PCT Pub. Date: Jul. 2, 2015

(65) Prior Publication Data
US 2016/0317553 A1 Nov. 3, 2016

Related U.S. Application Data

(60) Provisional application No. 61/920,982, filed on Dec. 26, 2013.

(51) Int. Cl.
*A61K 31/568* (2006.01)
*A61K 31/192* (2006.01)
*A61K 31/195* (2006.01)
*A61K 31/216* (2006.01)
*A61K 9/107* (2006.01)
*A61K 9/20* (2006.01)
*A61K 9/48* (2006.01)
*A61K 45/06* (2006.01)
*A61K 9/14* (2006.01)

(52) U.S. Cl.
CPC .......... *A61K 31/568* (2013.01); *A61K 9/1075* (2013.01); *A61K 9/20* (2013.01); *A61K 9/2009* (2013.01); *A61K 9/48* (2013.01); *A61K 9/485* (2013.01); *A61K 9/4858* (2013.01); *A61K 31/192* (2013.01); *A61K 31/195* (2013.01); *A61K 31/216* (2013.01); *A61K 45/06* (2013.01); *A61K 9/143* (2013.01)

(58) Field of Classification Search
CPC ........ A61K 31/568; A61K 45/06; A61K 9/20; A61K 9/48; C07J 1/00
See application file for complete search history.

(56) References Cited

U.S. PATENT DOCUMENTS

| 4,147,783 | A | 4/1979 | Van Der Vies |
| 6,054,136 | A | 4/2000 | Farah |
| 6,140,375 | A | 10/2000 | Nagahama |
| 6,191,105 | B1 | 2/2001 | Ekwuribe |
| 6,280,770 | B1 | 8/2001 | Pather |
| 6,303,662 | B1 | 10/2001 | Nagahama |
| 6,306,434 | B1 | 10/2001 | Hong |
| 6,309,665 | B2 | 10/2001 | Barthelemy |
| 6,312,704 | B1 | 11/2001 | Farah |
| 6,623,765 | B1 | 9/2003 | Dennis |
| 2003/0180352 | A1 | 9/2003 | Patel |
| 2005/0100608 | A1 | 5/2005 | Ebert |
| 2005/0101517 | A1 | 5/2005 | De Nijs |
| 2005/0129718 | A1 | 6/2005 | Sherman |
| 2013/0022674 | A1* | 1/2013 | Dudley .................. A61K 47/14 424/456 |
| 2013/0303495 | A1 | 11/2013 | Dhingra |

FOREIGN PATENT DOCUMENTS

| WO | 9524893 | 9/1995 |
| WO | 0059482 | 10/2000 |
| WO | 2015100406 A1 | 7/2015 |

OTHER PUBLICATIONS

Szapary et al (Am.Heart H., 2004, 148, 211-21).*
Otvos et al (Circulation, 2006, 113, 1556-1563).*
Miida, T. et al., Bezafibrate Increases Preb1-HDL at the Expense of HDL2b in Hypertriglyceridemia, Arterioscler Thromb Vasc Biol 20, 2428-2433, 2000.
Mombelli, G. et al., Paradoxical Decrease in High-Density Lipoprotein Choloesterol with Fenofibrate: A Quite Rare Phenomenon Indeed, Cardiovascular Therapeutics 28, 153-160, 2010.
PCT/US2014/072332 International Search Report and Written Opinion, dated Mar. 25, 2015, 8 pages.
Williams, P., Low HDL3 reduces the odds of men surviving to age 85 during 53-year follow-up, J Am Geriatr Soc 60(3), 1-14, 2012.
Al-Sukhun, et al., "Lipid Drug Delivery Systems and Their Fate after Oral Administration," Ph.D. Dissertation, University of Bath, UMI No. U601432, ProQuest LLC: Ann Arbor, MI (2002).
Amory, et al., "Oral testosterone in Oil Plus Dutasteride in Men: A Pharmacokinetic Study," J. Clin Endocrinol. & Metab., 90(5): 2610-2617 (2005).
Anby, et al., "Lipid Digestion as a Trigger for Supersaturation: Evaluation of the Impact of Supersaturation Stabilization on the in Vitro and in Vivo Performance of Self-Emulsifying Drug Delivery Systems," Mol. Pharm., 9: 2063-2079 (2012).
Ansari, et al., "Microemulsions as Potential Drug Delivery Systems: A Review," PDA J Pharm. Sci. Tech., 62(1): 66-79 (2008).
Araya, et al., "The novel formulation design of O/W microemulsion for improving the gastrointestinal absorption of poorly water soluble compounds, " Int. J. Pharm., 305: 61-74 (2005).

(Continued)

*Primary Examiner* — Sudhakar Katakam
(74) *Attorney, Agent, or Firm* — Dennis A. Bennett; Brock D. Levin

(57) ABSTRACT

Pharmaceutical products comprising a hypolipidemic agent and a testosterone ester such as testosterone undecanoate are provided. Methods of safely treating a testosterone deficiency or its symptoms with the inventive pharmaceutical products are also provided.

11 Claims, 22 Drawing Sheets

(56) References Cited

OTHER PUBLICATIONS

Araya, et al., "The Novel Formulation Design of Self-emulsifying Drug Delivery Systems (SEDDS) Type O/W Microemulsion I: Enhancing Effects on Oral Bioavailability of Poorly Water Soluble Compounds in Rats and Beagle Dogs," Drug Metab. Pharmacokinet., 20(4): 244-256 (2005).
BCS Classification-Formulations Report entitled Intra-Agency Agreement Between the Eunice Kennedy Shriver National Institute of Child Health and Human Development (NICHD) and the U.S. Food and Drug Administration (FDA) Oral Formulations Platform—Report 1 as of Mar. 11, 2016.
Bittner, et al., "Formulations and Related Activities for the Oral Administration of Poorly Water-soluble Compounds in Early Discovery Animal Studies," Drugs made in Germany, 45(1): 18-24 (2002).
Bittner, et al., "Formulations and Related Activities for the Oral Administration of Poorly Water-soluble Compounds in Early Discovery Animal Studies," Pharm. Ind., 64(8): 800-807 (2002).
Bowtle, et al., "Materials, Process, and Manufacturing Considerations for Lipid-Based Hard-Capsule Formats," Chapter 4, pp. 79-106, in Oral Lipid Based Formulations; Enhancing the Bioavailability of Poorly Water-Soluble Drugs, Hauss, ed., Informa Healthcare USA, Inc.: New York, NY (2007).
Brouwers, et al., "Supersaturating drug delivery systems: The answer to solubility-limited oral bioavailability?," J. Pharm. Sci., 98(8): 2549-2572 (2009).
Chakraborty, et al., "Lipid: an emerging platform for oral delivery of drugs with poor bioavailability," Eur. J. Pharm. Biopharm., 73: 1-15 (2009).
Chambin, et al., "Interest of multifunctional lipid excipients: Case of Gelucirel 44/14," Drug Dev. Ind. Pharm., 31: 527-534 (2005).
Charman, "Lipids, lipophilic drugs, and oral drug delivery-some emerging concepts," J. Pharm. Sci., 89: 967-978 (2000).
Charman, et al., "Absorption of danazol after administration to different sites of the gastrointestinal tract and the relationship to single- and doublepeak phenomena in the plasma profiles," J. Clin.Pharmacol., 33: 1207-1213 (1993).
Charman, et al., "Effect of food and a monoglyceride emulsion formulation on danazol bioavailability," J. Clin. Pharmacol., 33: 381-386 (1993).
Charman, et al., "Effects of lipid class and lipid vehicle volume on the intestinal lymphatic transport of DDT," Int. J. Pharm. 33: 165-172 (1986).
Charman, et al., "Physicochemical and physiological mechanisms for the effects of food on drug absorption: the role of lipids and pH," J. Pharm.Sci., 86: 269-282 (1997).
Charman, Susan A. et al., "Self-Emulsifying Drug Delivery Systems: Formulation and Biopharmaceutic Evaluation of an Investigational Lipophilic Compound", Pharmaceutical Research 9(1):87-93, (1992).
Cheema, et al., "Lipid vehicles for intestinal lymphatic drug absorption," J. Pharm. Pharmacol., 39: 55-56 (1987).
Christensen, et al., "Solubilisation of poorly water-soluble drugs during in vitro lipolysis of medium- and long-chain triacylglycerols," Eur. J. Pharm. Sci., 23: 287-296 (2004).
Constantinides, et al., "Formulation and Intestinal Absorption Enhancement Evaluation of Water-in-Oil Microemulsions Incorporating Medium-Chain Glycerides," Pharm. Res., 11(10): 1385-1390 (1994).
Constantinides, "Self-Emulsifying Drug Delivery Formulations in the 21st Century: Challenges and Opportunities," Chapter 28, pp. 284-296, in Controlled Drug Delivery: Designing Technologies for the Future, Park et al., eds., ACS Symposium Series 752, American Chemical Society (2000).
Constantinides, et al., "Advances in lipid-based drug solubilization and targeting," Adv. Drug Del. Rev., Preface, 56(9): 1239-1240 (2004).
Constantinides, et al., "Tocol emulsions for drug solubilization and parenteral delivery," Adv. Drug Del. Rev., 56: 1243-1255 (2004).

Constantinides, et al., "Advances in lipid nanodispersions for parenteral drug delivery and targeting," Adv. Drug Del. Rev., 60: 757-767 (2008).
Constantinides, et al., "Advances in the Use of Tocols as Drug Delivery Vehicles," Pharm. Res., 23(2): 243-255 (2006).
Constantinides, et al., "Considerations and recommendations on traditional and non-traditional uses of excipients in oral drug products," AAPS Open, 2: 1-6 (2016).
Constantinides, et al., "Formulation and physical characterization of water-in-oil microemulsions containing long versus medium-chain glycerides," Int. J. Pharm., 158: 57-68 (1997).
Constantinides, et al., "Formulation Development and Antitumor Activity of a Filter-Sterilizable Emulsion of Paclitaxel," Pharm. Res., 17(2): 175-182 (2000).
Constantinides, et al., "Lipid Formulation Strategies for Enhancing Intestinal Transport and Absorption of P-Glycoprotein (P-gp) Substrate Drugs: In vitro/In vivo Case Studies," J. Pharm. Sci., 96: 235-248 (2007).
Constantinides, P., "Lipid Microemulsions for Improving Drug Dissolution and Oral Absorption: Physical and Biopharmaceutical Aspects", Pharmaceutical Research, 12(11):1561-72, (1995).
Cruiné, "Increasing the Proportional Content of Surfactant (Cremophor EL) Relative to Lipid in Self-emulsifying Lipid-based Formulations of Danazol Reduces Oral Bioavailability in Beagle Dogs," Pharm. Res., 24(4): 748-757 (2007).
Cruiné, et al., "Evaluation of the Impact of Surfactant Digestion on the Bioavailability of Danazol after Oral Administration of Lipidic Self-Emulsifying Formulations to Dogs," J. Pharm. Sci., 96(2): 995-1012, (2008).
Dahan, A. et al., Ch. 6: Enhanced Gastrointestinal Absorption of Lipophilic Drugs, Enhancement in Drug Delivery, (2006) pp. 111-131.
Dahan, et al., "Rationalizing the selection of oral lipid based drug delivery systems by an in vitro dynamic lipolysis model for improved oral bioavailability of poorly water soluble drugs," J. Cont. Rel., 129: 1-10 (2008).
Devani, et al., "The emulsification and solubilisation properties of polyglycolysed oils in self-emulsifying formulations," J. Pharm. Pharmacol., 56: 307-317 (2004).
Dressman, et al., "Dissolution testing as a prognostic tool for oral drug absorption: immediate release dosage forms.," Pharm. Res., 15: 11-22 (1998).
Dressman, et al., "In vitro-in vivo correlations for lipophilic, poorly water-soluble drugs," Eur J. Pharm. Sci., 11: S73-S80 (2000).
Erlich, et al., "Relative bioavailability of danazol in dogs from liquid-filled hard gelatin capsule" Int. J. Pharm,. 179 (1): 49-53 (1999).
Excerpt from GlaxoSmithKline's New Drug Application No. 21-319 for DUAGEN (Dutasteride): Summary Review of Pharmacokinetics and Bioavailability, pp. 13-19 (Oct. 5, 2001).
Gao, et al., "Design and Development of Supersaturatable Self-Emulsifying Drug Delivery Systems for Enhancing the Gastrointestinal Absorption of Poorly Soluble Drugs," pp. 303-328 in Oral Lipid-Based Formulations: Enhancing the bioavailbility of poorly watersoluble drugs, 1st ed.; Hauss, ed.; Informa Healthcare: New York, vol. 170 (2007).
Gao, et al., "Development of a supersaturable SEDDS (S-SEDDS) formulation of paclitaxel with improved oral bioavailability." J. Pharm. Sci., 92(12): 2386-2398 (2003).
Gao, et al., "Development of supersaturatable selfemulsifying drug delivery system formulations for improving the oral absorption of poorly soluble drugs," Expert Opin. Drug Delivery, 3(1):97-110 (2006).
Gershanik, et al., "Self-dispersing lipid formulations for improving oral absorption of lipophilic drugs," Eur. J. Pharm. Biopharm., 50(1): 179-188 (2000).
Gershkovich, et al., "Inhibition of Intestinal Absorption of Cholesterol by Surface-Modified Nanostructured Aluminosilicate Compounds," J. Pharm. Sci., 98: 2390-2400 (2009).
Ghosh, et al., "Design and development of microemulsion drug delivery system of acyclovir for improvement of oral bioavailability," AAPS Pharm.Sci.Tech., 7: E1-E6 (2006).

(56) References Cited

OTHER PUBLICATIONS

Gibson, "Lipid-Based Excipients for Oral Drug Delivery," pp. 33-62 in Oral Lipid-Based Formulations: Enhancing the bioavailbility of poorly water-soluble drugs, Hauss, ed., Informa Heathcare: New York, vol. 170 (2007).
Glaxosmithkline, "An Evaluation of the Relative Bioavailability of the GI 198745 (Dutasteride) Soft Gelatin Capsule with Monodiglycerides of Caprylic/Capric Acid (MDC) in Healthy Adult Male Volunteers," Clinical Study Register for Study No. ARIA1004, pp. 1-4, downloaded from http://www.gskclinicalstudyregister.com/files2/917.pdf1109 (Jan. 2005).
Glaxosmithkline, AVODARTTM (dutasteride) Soft Gelatin Capsules, Prescribing Information, NDA 21-319/S-008, pp. 1-18 (Aug. 2004).
Gooren, et al., "Androgen Replacement Therapy: Present and Future," Drugs, 64(17): 1861-1891 (2004).
Grove, et al., "Bioavailability of seocalcitol II: development and characterisation of self-microemulsifying drug delivery systems (SMEDDS) for oral administration containing mediumand long chain triglycerides," Eur J. Pharm. Sci., 28: 233-242 (2006).
Groves, et al., "The self-emulsifying action of mixed surfactants in oil," Acta Pharm. Suec., 13: 361-372 (1976).
Gursoy, et al., "Self-emulsifying drug delivery systems (SEDDS) for improved oral delivery of lipophilic drugs," Biomed. Pharmacother., 58: 173-182 (2004).
Haskell, et al., "Perspectives in Pharmaceutical Nanotechnology," AAPS Newsmagazine, Jan. 2012, pp. 16-23 (2012).
Hauss, et al., "Lipid-Based Delivery Systems for Improving the Bioavailability and Lymphatic Transport of a Poorly Water-Soluble LTB4 Inhibitor", J. Pharm. Sci., 87(2): 164-169 (1998).
Hengge, et al., "Double-blind, randomized, placebo-controlled phase III trial of oxymetholone for the treatment of HIV wasting," AIDS, 17(5): 699-710 (2003).
Hong, et al., "A new self-emulsifying formulation of itroconazole with improved dissolution and oral absorption," J. Control Release, 110: 332-338 (2006).
Humberstone, et al., "Lipid-based vehicles for the oral delivery of poorly water soluble drugs," Adv. Drug Deliv. Rev., 25: 103-128 (1997).
James, K. C. et al., "Solubilities of Testosterone Proprionate and Related Esters in Organic Solvents", Journal of Pharmaceutical Sciences, 65(5):656-9, (1976).
James, K.C. et al., "The solubilities of the lower testosterone esters, Journal of Pharmacy and Pharmacology", 20:709-14, (1968).
Jannin, et al., "Approaches for the development of solid and semi-solid lipid based formulations," Adv. Drug Deliv. Rev., 60: 734-74 (2008).
Julianto, et al., "Improved bioavailability of vitamin E with a self-emulsifying formulation, " Int. J. Pharm., 200(25): 53-57 (2000).
Kang, et al., "Development of self-microemulsifying drug delivery systems (SMEDDS) for oral bioavailability enhancement of simvastatin in beagle dogs," Int. J. Pharm., 274: 65-73 (2004).
Kaur, et al., "Nanomedicine: Trends and Perspectives on Technologies and Products," Chapter 7, pp. 95-107 in Advances in NanoTechnology and Applications, vol. 2, Center for Nanotechnology Education, Research and Applications (Centera), Sullivan University, College of Pharmacy, Louisville, KY (2010).
Kawakami, et al., "Micro emulsion formulation for enhanced absorption of poorly soluble drug I Prescription design," J. Controlled Rel., 81: 65-74 (2002).
Khoo, et al., "Formulation design and bioavailability assessment of lipidic self-emulsifying formulations of halofantrine," Int. J. Pharm,. 167 (1-2): 155-164 (1998).
Kim, et al., "Preparation and In Vitro Evaluation of Self-Microemulsifying Drug Delivery Systems Containing Idebenone," Drug Dev. Ind. Pharm., 26: 523-529 (2000).
Kincl, et al., "Increasing Intestinal Absorption of Drugs by Formulation," Arch. Pharm., 319: 615-624 (1986).

Köhn, et al., "A new oral testosterone undecanoate formulation," World J. Urol., 21:311-315 (2003).
Kommuru, et al., "Self-emulsifying drug delivery systems (SEDDS) of coenzyme Q10: formulation development and bioavailability assessment," Int. J. Pharm., 212: 233-246 (2001).
Kossena, et al., "Probing drug solubilization patterns in the gastrointestinal tract after administration of lipid-based delivery systems: a phase diagram approach," J. Pharm. Sci., 93: 332-348 (2004).
Kossena, et al., "Separation and characterization of the colloidal phases produced on digestion of common formulation lipids and assessment of their impact on the apparent solubility of selected poorly water-soluble drugs," J. Pharm. Sci., 92: 634-648 (2003).
Kostewicz, et al., "Predicting the precipitation of poorly soluble weak bases upon entry in the small intestine," J. Pharm. Pharmacol., 56: 43-51 (2004).
Koukonen, et al., "Drug Solubilization Behavior During in Vitro Digestion of Simple Triglyceride Lipid Solution Formulaions," Pharm. Res., 2 (2): 245-253 (2004).
Koukonen, et al., "Drug Solubilization Behavior During in Vitro Digestion of Suspension Formulations of Poorly Water-Soluble Drugs in Triglyceride Lipids," Pharm. Res., 21 (2): 254-260 (2004).
Kuehl, et al. "Formulation and In Vivo Evaluation of Chlorpropham (CIPC) Oral Formulations," J. Pharm. Sci., 97(12): 5222-5228 (2008).
Liang, et al., "Inhibition of steriod 5α-reductase by specific aliphatic unsaturated fatty acids," Biochem. J., 285: 557-562 (1992).
Liu, et al., "Research and development in drug innovation: reflections from the 2013 bioeconomy conference in China, lessons learned and future perspectives," Acta Pharmaceutica Sinica B., 4(2): 112-119 (2014).
Loper, et al., "Equivalence of a self-emulsifying drug delivery system (SEDDS) and soybean oil for oral delivery of a 5a-reductase inhibitor in rhesus monkeys," pp. 369-372 in Proc. Eur. Symp. Formulation of Poorly-available Drugs for Oral Absorption, Couvreur et al., eds., Editions de Sante: Paris (1996).
MacGregor, et al., "Lipolysis of oily formulations in the gastro-intestinal tract," Adv. Drug Delivery Rev., 25: 33-46 (1996).
MacGregor, KJ, et al., 'Influence of lipolysis on drug absorption from the gastro-intestinal tract,' Advanced Drug Delivery Reviews 25 (1997) 33-46.
Mackenzie, et al., "Targeting Mitochondrial STAT3 with the Novel Phospho-Valproic Acid (MDC-1112) Inhibits Pancreatic Cancer Growth in Mice," PLoS One, 8(5): 1-11 (2013).
Maisey et al., 'Clinical Efficacy of Testosterone Undecanoate in Male Hypogonadism,' Clinical Endocrinology, 1981, pp. 625-629, vol. 14.
Mattheolabakis, et al., "Nanodelivery strategies in cancer chemotherapy: biological rationale and pharmaceutical perspectives," Nanomedicine, 7(10): 1577-1590 (2012).
Mattheolabakis, et al., "Pegylation Improves the Pharmacokinetics and Bioavailability of Small-Molecule Drugs Hydrolyzable by Esterases: A Study of Phospho-Ibuprofen," J. Pharmacol. Exp. Ther., 351: 61-66 (2014).
Mattheolabakis, et al., "Sterically Stabilized Liposomes Incorporating the Novel Anticancer Agent Phospho-Ibuprofen (MDC-917): Preparation, Characterization, and In Vitro/In Vivo Evaluation," Pharm. Res., 29: 1435-1443 (2012).
Miller, et al., "Targeted Intestinal Delivery of Supersaturated Itraconazole for Improved Oral Absorption," Pharm. Res., 25 (6): 1450-1459 (2008).
Mohsin, et al., "Design of Lipid-Based Formulations for Oral Administration of Poorly Water-Soluble Drugs: Precipitation of Drug after Dispersion of Formulations in Aqueous Solution," J. Pharm. Sci., 98(10): 3582-3595.
Muchow, et al., "Production and characterization of testosterone undecanoate-loaded NLC for oral bioavailability enhancement," Drug Dev. Ind. Pharm., 37(1): 8-14 (2011).
Muchow, M. et al., Testosterone undecanoate—increase of oral bioavailability by nanostructured lipid carriers (NLC), Journal of Pharmaceutical Technology & Drug Research (2013), pp. 1-10.
Müllertz, et al., "New perspectives on lipid and surfactant based drug delivery systems for oral delivery of poorly soluble drugs," J. Pharm. Pharmacol., 62: 1622-1636 (2010).

(56) References Cited

OTHER PUBLICATIONS

Nicolaides, et al., "Biorelevant dissolution testing to predict the plasma profile of lipophilic drugs after oral administration," Pharm. Res., 18: 380-388 (2001).
Noguchi, T, et al., 'The effect of drug lipophilicity and lipid vehicles on the lymphatic absorption of various testosterone,' International Journal of Pharmaceutics, 24 (1985) 173-184.
O'Driscoll, "Lipid-based formulations for intestinal lymphatic delivery," Eur. J. Pharm. Sci., 15: 405-415 (2002).
Patel, et al., "A Self Micro Emulsifying Drug Delivery System (SMEDDS)," Int. J. Pharma. Sci. Rev. Res., 4(3): 29-35 (2010).
Porter, C. et al., "Lipid-Based Formulations for Oral Administration: Opportunities for Bioavailability Enhancement and Lipoprotein Targeting of Lipophilic Drugs", Journal of Receptor & Signal Transduction Research, 21(2&3):215-57, (2001).
Porter, et al., "Enhancing intestinal drug solubilisation using lipid-based delivery systems," Adv. Drug Del. Rev., 60: 673-691 (2008).
Porter, et al., "In vitro assessment of oral lipid based formulations," Adv. Drug Deliv. Rev., 50: S127-S147 (2001).
Porter, et al., "Lipid based formulations: Exploring the link between in vitro Supersaturation and in vivo exposure," Bull. Tech. Gattefoss, 104: 61-69 (2011).
Porter, et al., "Lipids and lipid-based formulations: optimizing the oral delivery of lipophilic drugs," Nature Reviews Drug Discovery, 6: 231-248 (2007).
Porter, et al., "Lymphatic transport of halofantrine in the triple-cannulated anaesthetized rat model; effect of lipid vehicle digestion," J. Pharm. Sci., 85: 351-356 (1996).
Porter, et al., "Preface: Lipid-based systems for the enhanced delivery of poorly water soluble drugs," Adv. Drug Del. Rev., 60(6): 615-616 (2008).
Porter, et al., "Susceptibility to Lipase-Mediated Digestion Reduces the Oral Bioavailability of Danazol After Administration as a Medium-Chain Lipid-Based Microemulsion Formulation," Pharm. Res., 21(8): 1405-1412 (2004).
Porter, et al., "Uptake of drugs into the intestinal lymphatics after oral administration," Adv. Drug Deliv. Rev., 25(1):71-89, (1997).
Porter, et al., "Use of in vitro lipid digestion data to explain the in vivo performance of triglyceride based lipid formulations for the oral administration of poorly water-soluble drugs: Studies with Halofantrine," J. Pharm. Sci., 93: 1110-1121 (2004).
Pouton, "Self-emulsifying drug delivery systems: Assessment of the efficiency of emulsification," Int. J. Pharm., 27: 335-348 (1985).
Pouton, "Assessment of the efficiency of self-emulsifying formulations," J. Pharm. Pharmacol., 36: 51P (1984).
Pouton, "Effects of the inclusion of a model drug on the performance of self-emulsifying formulations," J. Pharm. Pharmacol., 37: 1P (1985).
Pouton, "Formulation of poorly watersoluble drugs for oral administration: Physicochemical and physiological issues and the lipid formulation classification system," Eur. J. Pharm. Sci., 29: 278-287 (2006).
Pouton, "Formulation of self-emulsifying drug delivery systems," Adv. Drug Del. Rev., 25(1): 47-58 (1997).
Pouton, "Lipid formulations for oral administration of drugs: non-emulsifying, self-emulsifying and 'self-microemulsifying' drug delivery systems," Eur. J. Pharm. Sci., 11(Suppl. 2): S93-S98 (2000).
Pouton, et al., "Key issues when formulating with lipids." Bull. Tech. Gattefosse, 92: 41-50 (1999).
Pouton, et al., "Self-emulsifying systems for oral delivery of drugs," Proc. Int. Symp. Control. Rel. Bioact. Mater., 14: 113-114 (1987).
Pouton, et al., "Formulation of lipid-based delivery systems for oral administration: Materials, methods and strategies," Adv. Drug Del. Rev., 60: 625-637 (2008).
Pouton, Ph.D. thesis, University of London, London, UK (1982).
Quan, et al., "Studies on Preparation and Absolute Bioavailability of a Self-Emulsifying System Containing Puerarin," Chem. Pharm. Bull., 55(5): 800-803 (2007).

Rajesh, et al., "Lipid Based Self-Emulsifying Drug Delivery System (SEDDS) for Poorly Water-Soluble Drugs: A Review," J. Global Pharma Tech., 2(3): 47-55 (2010).
Reddy, et al., "Review on self micro emulsifying drug delivery systems," Int. J. Res. Pharm. Sci., 2(3): 382-392 (2011).
Reddy, et al., "Lymphatic transport of orally administered drugs," Indian J. Exp. Biol., 40: 1097-1109 (2002).
Reymond, et al., In Vivo Model for Ciclosporin Intestinal Absorption in Lipid Vehicle,. Pharm.Res., (10): 677-679 (1988).
Robinson, "Semi-solid formulations for oral drug delivery," Bulletin Technique-Gattefosse, 89: 11-13 (1996).
Roth, M.Y. et al., Steady-state pharmacokinetics of oral testosterone undecanoate with concomitant inhibition of 5a-reductase by finasteride, International Journal of Andrology, (2001) vol. 34, No. 601, pp. 541-547.
Rytting, Erik et al. "Aqueous and cosolvent solubility data for drug-like organic compounds." The AAPS journal7A (2005): E78-E105.
Sek, et al., "Examination of the impact of a range of Pluronic surfactants on the in vitro solubilisation behaviour and oral bioavailability of lipidic formulations of atovaquone," J. Pharm. Pharmacol., 58: 809-820 (2006).
Sek, et al.,"Evaluation of the in-vitro digestion profiles of long and medium chain glycerides and the phase behaviour of their lipolytic products," J. Pharm. Pharmacol., 54: 29-41 (2002).
Shah, et al., "Self-emulsifying drug delivery systems (SEDDS) with polyglycolyzed glycerides for improving in vitro dissolution and oral absorption of lipophilic drugs," Int. J. Pharm., 106(1): 15-23 (1994).
Shen, et al., "Preparation and evaluation of self-microemulsifying drug delivery systems (SMEDDS) containing atorvastatin," J. Pharm. Pharmacol., 58: 1183-1191 (2006).
Sivak, et al., "Protonated nanostructured aluminosilicate (NSAS) reduces plasma cholesterol concentrations and atherosclerotic lesions in Apolipoprotein E deficient mice fed a high cholesterol and high fat diet," Lipids in Health and Disease, 8: 30-34 (2009).
Solomon, et al., "Inhibition of lipolysis of medium-chain triglycerides by non-ionic surfactants, a structure/activity study," pp. 437-438 in Formulation of Poorly Available Drugs for Oral Administration, Couvreur et al., eds., Editions de Sante, Paris, Couvreur (1996).
Stegemann, et al., "When poor solubility becomes an issue: From early stage to proof of concept," Eur. J. Pharma. Sci., 31(5): 249-261 (2007.
Strickley, "Currently marketed oral lipid-based dosage forms: drug products and excipients," pp. 1-31 in "Oral Lipid-Based Formulations: Enhancing the Bioavailability of Poorly Water-Soluble Drugs," Nauss, ed., New York: Informa Healthcare (2007).
Subramanian, et al., "Formulation design of self-emulsifying drug delivery systems for improved oral bioavailability of celecoxib," Biol. Pharm. Bull., 27: 1993-1999 (2004).
Sunesen, et al., "Effect of liquid volume and food intake on the absolute bioavailability of danazol, a poorly soluble drug," Eur. J. Pharm. Sci., 24: 297-303 (2005).
Swerdloff, et al., "Dihydrotestosterone: Biochemistry, Physiology, and Clinical Implications of Elevated Blood Levels," Endocr. Rev., 38(3): 220-254 (2017).
Swerdloff, et al., "Long-Term Pharmacokinetics of Transdermal Testosterone Gel in Hypogonadal Men," J. Clin. Endocrinol. & Metab., 85(12): 4500-4510 (2000).
Talegaonkar, "Microemulsions: A Novel Approach to Enhanced Drug Delivery," Recent Patents Drug Del. Form., 2: 238-257 (2008).
Tarr, et al., "Enhanced intestinal absorption of cyclosporine in rats through the reduction of emulsion droplet size," Pharm. Res., 6: 40-43 (1989).
Trull, et al., "Enhanced absorption of new oral cyclosporin microemulsion formulation, Neoral, in liver transplant recipients with external biliary diversion," Transplant. Proc., 26: 2977-2978 (1994).
Tuleu, et al., "Comparative bioavailability study in dogs of a self-emulsifying formulation of progesterone presented in a pellet and liquid form compared with an aqueous suspension of progesterone" J. Pharm. Sci., 93: 1495-1502 (2004).

(56) References Cited

OTHER PUBLICATIONS

Vertzoni, et al., "Dissolution media simulating the intralumenal composition of the small intestine: physiological issues and practical aspects," J. Pharm. Pharmacol., 56: 453-462 (2004).
Wakerly, "Self-emulsifying drug delivery systems based on nonionic surfactant-oil mixtures," Ph.D. thesis, University of Bath, Bath, UK (1989).
Wakerly, et al., "Evaluation of the self-emulsifying performance of a non-ionic surfactantvegetable oil mixture," J. Pharm. Pharmacol., 39: 6P (1987).
Wakerly, et al., "Self-emulsification of vegetable oil-nonionic surfactant mixtures: A proposed mechanism of action," Chapter 18, pp. 242-255, in Phenomena in Mixed Surfactant Systems, Scamehorn et al., eds., ACS Symp. Ser. 311, American Chemical Society (1986).
Wakerly, et al., "The effect of surfactant HLB on the self-emulsifying efficiency of non-ionic surfactant vegetable oil mixtures," J. Pharm. Pharmacol., 38: 2P (1986).
Wong, et al., "Carboxylesterases 1 and 2 Hydrolyze Phospho-Nonsteroidal Anti-Inflammatory Drugs: Relevance to Their Pharmacological Activity," J. Pharmacol. Exp. Therapeutics, 340(2): 422-432 (2012).
Xie, et al., "In Vitro and In Vivo Metabolic Studies of Phospho-aspirin (MDC-22)," Pharm. Res., 29: 3292-3301 (2012).
Xie, et al., "Regioselective oxidation of phospho-NSAIDs by human cytochrome P450 and flavin monooxygenase isoforms: implications for their pharmacokinetic properties and safety," Br. J. Pharmacol., 167: 222-232 (2012).
Yalkowsky, "Solubilization by Cosolvents," Chapter 6, pp. 236-320, in Solubility and Solubilization in Aqueous Media, American Chemical Society, Oxford Univ. Press: New York, NY (1999).
Yáñez, et al., "Intestinal lymphatic transport for drug delivery," Adv. Drug Del. Rev., 63: 923-942 (2011).
Yap, et al., "Influence of lipolysis and droplet size on tocotrienol absorption from self-emulsifying formulations," Int. J. Pharm., 281 (2004): 67-78 (2004).
Yin, A. et al., "Reexamination of Pharmacokinetics of Oral Testosterone Undecanoate in Hypogonadal Men With a New Self-Emulsifying Formulation", Journal of Andrology, 33(2):190-201, (2012).
Zangerberg, et al., "A dynamic in vitro lipolysis model. II: evaluation of the model," Eur. J. Pharm. Sci., 14: 237-244 (2001).
Zhu, et al., "Phospho-Sulindac (OXT-328) Inhibits the Growth of Human Lung Cancer Xenografts in Mice: Enhanced Efficacy and Mitochondria Targeting by its Formulation in Solid Lipid Nanoparticles," Pharm. Res., 29: 3090-3101 (2012).
Zhu, et al., "Phosphosulindac (OXT-328) Selectively Targets Breast Cancer Stem Cells In Vitro and in Human Breast Cancer Xenografts," Stem Cells, 30: 2065-2075 (2012).
International Application No. PCT/US2014/072332; International Preliminary Report on Patentability, dated Jun. 28, 2016; 6 pages.
International Application No. PCT/US2014/072332; International Search Report and Written Opinion of the International Search Authority, dated Mar. 25, 2015; 8 pages.

* cited by examiner

ORAL PHARMACEUTICAL PRODUCTS AND METHODS OF USE COMBINING TESTOSTERONE ESTERS WITH HYPOLIPIDEMIC AGENTS

This application is a national stage entry of PCT/US2014/072332, filed Dec. 24, 2014, which claims the benefit of priority of U.S. Provisional Application No. 61/920,982, filed Dec. 26, 2013, the disclosures of which are hereby incorporated by reference as if written herein in their entireties.

FIELD OF THE INVENTION

The present invention relates generally to pharmaceutical products comprising oral formulations of testosterone esters for the treatment of testosterone deficiency, in combination with hypolipidemic agents. More particularly, the present invention relates to oral formulations of testosterone undecanoate (TU) with enhanced and extended absorption and pharmacokinetics (PK), in combination with an agonist of the peroxisome proliferator-activated receptor-α (PPARα).

BACKGROUND OF THE INVENTION

Testosterone (T) is a primary androgenic hormone produced in the interstitial cells of the testes and is responsible for normal growth, development and maintenance of male sex organs and secondary sex characteristics (e.g., deepening voice, muscular development, facial hair, etc.). Throughout adult life, testosterone is necessary for proper functioning of the testes and its accessory structures, the prostate and seminal vesicles; for sense of well-being; and for maintenance of libido and erectile potency.

Testosterone deficiency—insufficient secretion of T characterized by low serum T concentrations—can give rise to medical conditions (e.g., hypogonadism) in males. Symptoms associated with male hypogonadism include impotence and decreased sexual desire, fatigue and loss of energy, mood depression, regression of secondary sexual characteristics, decreased muscle mass, and increased fat mass. Furthermore, hypogonadism in men is a risk factor for osteoporosis, metabolic syndrome, type II diabetes, and cardiovascular disease.

Various testosterone replacement therapies (TRTs) are commercially available for the treatment of male hypogonadism. Pharmaceutical preparations include both testosterone and testosterone derivatives in the form of intramuscular injections, implants, oral tablets of alkylated T (e.g., methyltestosterone), topical gels, or topical patches. All of the current T therapies, however, fail to adequately provide an easy and clinically effective method of delivering T. For example, intramuscular injections are painful and are associated with significant fluctuations in serum T levels between doses; T patches are generally associated with levels of T in the lower range of normal (i.e., clinically ineffective) and often cause substantial skin irritation; and T gels have been associated with unsafe transfer of T from the user to women and children. As well, the sole "approved" oral T therapy, methyltestosterone, is associated with a significant occurrence of liver toxicity. Over time, therefore, the current methods of treating testosterone deficiency suffer from poor compliance and thus unsatisfactory treatment of men with low T.

Testosterone and its esters are poorly bioavailable—owing to extensive first pass intestinal and hepatic metabolism—or ineffective—due to an inability of the body to liberate testosterone from its testosterone prodrug. For example, testosterone and testosterone esters with side chains of less than 10 carbons in length are primarily absorbed via the portal circulation resulting in substantial, if not total, first pass metabolism. Fatty acid esters of long carbon chains (i.e., 14 or more carbons) may be absorbed by intestinal lymphatics, but the longer the fatty acid chain length, the slower the rate and extent of hydrolysis of the ester by esterases to liberate testosterone thus resulting in poor (i.e., clinically ineffective) pharmacological activity.

Other than selection of a testosterone ester, the formulation of the testosterone ester presents unique challenges. The gastrointestinal environment is decidedly aqueous in nature, which requires that drugs must be solubilized for absorption. However, testosterone and particularly its esters are extremely insoluble in water and aqueous media, and even if the T or T ester is solubilized initially in the formulation, the formulation must be able to maintain the drug in a soluble or dispersed form without precipitation or, otherwise, coming out of solution in vivo (although such a property can be tested in vitro, for example, by mixing the contents of a formulation in simulated intestinal fluid). Furthermore, an oral T formulation must, effectively release T or T ester according to a desired release profile. Hence, an effective formulation of T or T ester must balance good solubility with optimum release and satisfaction of a targeted plasma or serum concentration profile.

For these reasons, among others, no oral formulation of testosterone or testosterone esters has been approved by the United States Food and Drug Administration (FDA) to date. In fact, the only oral testosterone product ever approved to date by the FDA is methyltestosterone (in which a methyl group covalently bound to a testosterone "nucleus" at the C-17 position to inhibit hepatic metabolism; note, also, that methyltestosterone is not a prodrug of testosterone) and this approval occurred several decades ago. Unfortunately, use of methyltestosterone has been associated with a significant incidence of liver toxicity, and it is rarely prescribed to treat men with low testosterone.

As noted above, fatty acid esters of testosterone provide yet another mode of potential delivery of testosterone to the body (i.e., as a "prodrug"). Once absorbed, testosterone can be liberated from its ester via the action of non-specific tissue and plasma esterases. Furthermore, by increasing the relative hydrophobicity of the testosterone moiety and the lipophilicity of the resulting molecule as determined by its n-octanol-water partition coefficient (log P) value, such prodrugs can be absorbed, at least partially, via the intestinal lymphatics, thus reducing first-pass metabolism by the liver. In general, lipophilic compounds having a log P value of at least 5 and oil solubility of at least 50 mg/mL are transported primarily via the lymphatic system.

Oral formulations of testosterone esters providing clinically-effective serum testosterone levels to treat hypogonadal men (i.e., those with a serum T concentration of ≤300 ng/dL) over an extended period of time are disclosed in WO2011129812, which is incorporated in its entirety by reference.

It has long been recognized that TRT lowers serum high-density-lipoprotein (HDL) and its surrogate value, serum HDL-cholesterol (HDL-C) (Meriggiola, M. C., et al., *Int J Androl*, 1995. 18(5): p. 237-42; Semmens, J., et al., *Metabolism*, 1983. 32(5): p. 428-32). Two factors may influence the amount of HDL suppression: route of delivery, and dose. Typical HDL suppression is about 10% with formulations that deliver T levels at the lower end of the physiological range, such as gels. Other formulations such as such injectable testosterone enanthate (TE), implantable subcutaneous TU pellets, and oral TU (Andriol®) have much higher suppression of HDL than gels (up to 37% for pellets). Independent of the mode of delivery, supra-physiological doses of T, such as in athletes abusing anabolic steroids, lead to even higher HDL suppression.

It has also long been recognized that elevated serum levels of HDLc are associated with reduced risk of cardiovascular (CV) disease and its sequelae (Hislop, M. S., et al., *Atherosclerosis*, 2001. 159(2): p. 425-32). Because TRT lowers HDLc, there has been the concern that TRT may increase the risk of cardiovascular disease (CVD). However, the effect of raising or lowering HDLc on CV risk and mortality has recently come into question based on: a) clinical trials in which raising HDLc did not improve mortality (Toth, P. P., et al., *J Clin Lipidol*, 2013. 7(5): p. 484-525; Boden, W. E., et al., N Engl J Med, 2011, 365(24): p. 2255-67), but in fact worsened it; and b) based on populations who have very low HDLc, albeit with mutant HDL associated proteins, who have reduced CV risk (Dodani, S., et al., *J Clin Lipidol*, 2009. 3(2): p. 70-7). Thus due to the complexity of HDL biology that encompasses not only the measurement of total HDLc but also the composition and function of this lipid fraction, there does not seem to be a simple relationship between HDLc serum concentrations and CV risk/mortality. As the functional and compositional complexity of HDL becomes better understood, it has become clear that HDLc is a relatively crude index of CV risk, and the clinical significance of HDLc alone has been increasingly called into question (de la Llera-Moya, M., et al., *Arterioscler Thromb Vase Biol*, 2010. 30(4): p. 796-801; deGoma, E. M., et al., *J Am Coll Cardiol*, 2008. 51(23): p. 2199-211. 29; Vaisar, T., et al., *J Clin Invest*, 2007. 117(3): p. 746-56).

The inverse relationship between HDLc and CVD risk has been attributed to its function in reverse cholesterol transport (RCT) and other antiinflammatory or anti-oxidative functions (Toth, P. P., et al., *J Clin Lipidol*, 2013. 7(5): p. 484-525). The dogma that low HDLc is a therapeutic target has recently been challenged based on negative findings in outcome trials with niacin (Boden, W. E., et al., N Engl J Med, 2011, 365(24): p. 2255-67) and CETP inhibitors. These trials did not show a benefit in raising HDLc, and in fact treatment which raised HDLc had a deleterious effect on CVD risk (Barter, P. J., et al., *N Engl J Med*, 2007. 357(21): p. 2109-22). Furthermore, normal HDLc levels (men >40 mg/dL and women >50 mg/dL) are present in many patients with CV events, as exemplified in the Framingham study in which about 43% of the CV events occur in patients with low serum levels of low-density-lipoproteins (LDL) and normal levels of HDLc (Dodani, S., et al., *J Clin Lipidol*, 2009. 3(2): p. 70-7); Annema, W. and von Eckardstein, A., *Circ J*, 2013. 77(10): p. 2432-48). Finally low HDLc levels associated with mutant Apo-A1 such as Apo-A1 Milano are cardioprotective (Chiesa, G., and Sirtori, C. R., *Curr Opin Lipidol*, 2003. 14(2): p. 159-63). while other mutations in Apo-A1, ABCA1, and LCAT also lead to low HDLc level but are associated with increased cardiovascular risk (Tietjen, I., et al., *Biochim Biophys Acta*, 2011. 1821(3): p. 416-24). The conclusion from these observations is that HDLc is a relatively poor measure of HDL functionality and hence CV risk (Annema, W. and von Eckardstein, A., *Circ J*, 2013. 77(10): p. 2432-48). This has prompted the development of novel metrics of HDL function that may be more sensitive then the absolute level of HDLc in predicting risk. Among these metrics are in vitro CE capacity, pre-particle quantification, and HDL particle fractionation.

An exploratory analysis of the effects of exposure to oral TU or topical T gel on CE capacity and the quantitation of HDL particle numbers and HDL subfractions, demonstrated: 1) a modest but statistically significant drop in mean CE capacity in the oral TU group compared to T gel, but both treatments were associated with a decrease; 2) a decrease in total HDL particle number which was not statistically significant between the two groups; and 3) a redistribution in HDL subclasses in the oral TU group with a significant shift toward very small, more anti-atherogenic, HDL subclass particles (Example 7). This effect may be driven upregulation of hepatic lipase (to which oral T would be exposed upon its passage through the hepatic portal system), which breaks down large, cholesterol-laden HDL particles to smaller preβ-1 and nascent HDL particles, which are very efficient reverse cholesterol transporters through the ABCA1 receptor.

The peroxisome proliferator-activated receptor (PPAR) isoforms are members of the nuclear receptor superfamily of ligand-activated transcription factors. They were first identified in Xenopus frogs as receptors that induce the proliferation of peroxisomes (Dreyer et al. 1992. Cell 68: 879-887). Three PPAR isoforms are known: PPARα, PPARγ, and PPARδ. The PPARs control gene expression by interaction with specific response elements in the promoter region of target genes (Tugwood et al. 1996. Ann. New York Acad. Sci. 804: 252-265). The PPARs play a central role in carbohydrate and lipid homeostasis, and govern other biological processes such as energy metabolism, cell proliferation and differentiation, and inflammation (Chakrabarti and Rajagopalan. 2004. Curr. Med. Chem.: Immunol. Endocr. Metab. Agents 4: 67-73; Escher and Wahli. 2000. Mutation Res. 448: 121-138; Gilde and Van Bilsen. 2003. Acta Physiol. Scand. 178: 425-434; Kersten, S. 2002. Eur. J. Pharmacol. 440: 223-234; Mudaliar and Henry. 2002. Curr. Opin. Endocrinol. Diabetes 9: 285-302). The PPARα isoform, predominantly involved in fatty acid and lipid catabolism and import, activates genes involved in fatty acid oxidation in the liver, heart, kidney, and skeletal muscles (Fruchart et al. 2003. Prog. Exper. Cardiol. 8: 3-16; Gilde and Van Bilsen, supra).

The pharmocological effects of PPARα agonists are well established. In the liver, activation of PPARα leads to increased β-oxidation of fatty acids and decreased triglyceride-VLDL (very low density lipoprotein) synthesis (Fruchart and Duriez. 2004. Ann. Pharmaceut. Franc. 62: 3-18). Activation of PPARα also leads to the reduction of triglyceride because of repression of hepatic apolipoprotein C-III and to the increase in lipoprotein lipase gene expression (Gervois et al. 2000. Clin. Chem. Lab. Med. 38: 3-11). Furthermore, PPARα activation causes induction of hepatic apolipoprotein A-I and A-II expression, in humans, leading to increased plasma HDL cholesterol.

Likewise, the clinical benefit of PPARα agonists with respect to CVD risk is well established. For example, a secondary prevention study, the Veterans Affairs High-Density Lipoprotein Intervention Trial (VA-HIT), demonstrated a significant 22% reduction in coronary heart disease (CHD) events during a median follow-up of 5.1 years by treating patients with PPARα agonist gemfibrozil (a fibric acid derivative), when the predominant lipid abnormality was low HDLc (Otvos, J. D., et al., Circulation. 2006; 113: 1556-1563). In the same study, gemfibrozil treatment increased total HDL particles (10%) as a result of increased numbers of small HDL particles (21%) offsetting reductions in large- and medium-size HDL subclass particles.

TRT with concomitant administration of a hypolipidemic agent such as a PPARα agonist can mitigate any T-induced decreases in apoA1 and HDL. Moreover, both T and PPARα agonists upregulate SR-B1, which mediates CE from large HDL particles. They both also upregulate hepatic lipase, which generates very small HDL particles resulting in greater CE mediated through ABCA1 receptor. Furthermore, PPARα agonists further enhance CE through an increase in ABCA1 transcriptional activity by up-regulating the receptor that is the only gateway for mediating CE via small HDL small particles.

There remains a need for pharmaceutical products that safely treat testosterone deficiency and symptoms thereof, which includes mitigating any negative impact T may have on cardiovascular outcomes. Described herein are pharmaceutical products that meet such need through reliance on the mechanistic synergy between oral T esters and hypolipidemic agents such as PPARα agonists whereby both agents act to increase serum concentration of anti-atherotic very small HDL particles, including preβ-1 HDL.

SUMMARY OF THE INVENTION

One aspect of the present invention is directed to a pharmaceutical product comprising one or more pharmaceutical compositions, wherein the one or more pharmaceutical compositions comprise: a hypolipidemic agent that increases the plasma concentration of one or more HDL particle subclasses in an individual; and a testosterone ester. In some embodiments, the testosterone ester is testosterone undecanoate.

In some embodiments, the hypolipidemic agent described herein increases the plasma concentration of the $HDL_{3b}$ particle subclass in the individual selectively over one or more other HDL particle subclasses. In some embodiments, the hypolipidemic agent described herein increases the plasma concentration of the $HDL_{3c}$ particle subclass selectively over one or more other HDL particle subclasses. In some embodiments, the hypolipidemic agent described herein increases the plasma concentration of preβ-1 HDL particles over one or more other HDL particles. In some embodiments, the hypolipidemic agent described herein decreases the plasma concentration of the $HDL_{2a}$ particle subclass in the individual. In some embodiments, the hypolipidemic agent described herein decreases the plasma concentration of the $HDL_{2b}$ particle subclass in the individual.

In some embodiments, the hypolipidemic agent described herein is a peroxisome proliferator activating receptor (PPAR) agonist. In some embodiments, the PPAR agonist is a pan-PPAR agonist. In some embodiments, the PPAR agonist is a selective PPARδ agonist. In some embodiments, the PPAR agonist is a selective PPARα agonist. In some embodiments, selective PPARα agonist is selected from: bezafibrate, ciprofibrate, clofibrate, fenofibrate, and gemfibrozil.

In some embodiments, the testosterone ester is solubilized in a carrier comprising at least one lipophilic surfactant and at least one hydrophilic surfactant. In some embodiments, the total lipophilic surfactant to total hydrophilic surfactant ratio (w/w) in the carrier falls in the range of about 6:1 to 3.5:1.

One aspect of the present invention is directed to pharmaceutical products described herein comprising one or more pharmaceutical compositions, wherein oral administration of the one or more pharmaceutical compositions to the individual provides an average serum testosterone concentration at steady state in the individual falling in the range of about 300 to about 1100 ng/dL.

In some embodiments, the individual's serum testosterone $C_{max}$ does not exceed 2500 ng/dL when the one or more pharmaceutical compositions are administered to the individual. In some embodiments, the individual's serum testosterone $C_{max}$ does not exceed 2500 ng/dL when the one or more pharmaceutical compositions are administered to the individual with a meal. In some embodiments, the individual's serum testosterone $C_{max}$ does not exceed 1800 ng/dL when the one or more pharmaceutical compositions are administered to the individual. In some embodiments, the individual's serum testosterone $C_{max}$ does not exceed 1800 ng/dL when the one or more pharmaceutical compositions are administered to the individual with a meal. In some embodiments, the individual's serum testosterone $C_{max}$ does not exceed 1500 ng/dL when the one or more pharmaceutical compositions are administered to the individual. In some embodiments, the individual's serum testosterone $C_{max}$ does not exceed 1500 ng/dL when the one or more pharmaceutical compositions are administered to the individual with a meal.

One aspect of the present invention is directed to pharmaceutical products as described herein, wherein the at least one hydrophilic surfactant comprises Cremophor® RH 40 (polyoxyethyleneglycerol trihydroxystearate).

One aspect of the present invention is directed to pharmaceutical products as described herein, wherein the at least one lipophilic surfactant comprises oleic acid.

One aspect of the present invention is directed to pharmaceutical products comprising one or more pharmaceutical compositions as described herein, which upon oral administration of the one or more pharmaceutical compositions to the individual with a meal having a fat content ranging from as low as 20 wt % to as high as 50 wt %, provides an average serum testosterone concentration in the individual substantially the same as that observed upon oral administration of the one or more pharmaceutical compositions to the individual with a meal having a fat content of about 30 wt %.

One aspect of the present invention is directed to pharmaceutical products comprising one or more pharmaceutical compositions as described herein, which provides a serum testosterone rapid phase half-life in the individual of about 5 hours upon oral administration of the one or more pharmaceutical compositions to the individual.

One aspect of the present invention is directed to pharmaceutical products comprising one or more pharmaceutical compositions as described herein, which provides a serum testosterone terminal half-life in the individual of about 29 hours upon oral administration of the one or more pharmaceutical compositions to the individual.

One aspect of the present invention is directed to pharmaceutical products comprising one or more pharmaceutical compositions as described herein, which upon oral administration of the one or more pharmaceutical compositions to an individual suffering from testosterone deficiency or its symptoms, provides a mean serum testosterone concentration in the individual at day 30 of a daily treatment regimen with the pharmaceutical product, which is substantially the same as that observed on day 7.

One aspect of the present invention is directed to pharmaceutical products comprising one or more pharmaceutical compositions as described herein, wherein the mean serum testosterone concentration in the individual obtained at day 30 of a daily treatment regimen with the pharmaceutical product is substantially the same as that observed on day 60.

One aspect of the present invention is directed to pharmaceutical products as described herein, wherein the hypolipidemic agent and the testosterone ester are combined in the same pharmaceutical composition. In some embodiments, the pharmaceutical composition is a liquid-filled capsule, a powder-filled capsule, or a tablet. In some embodiments, the pharmaceutical composition comprises a self-emulsifying drug delivery system, a self-microemulsifying drug delivery system, or a self-nanoemulsifying drug delivery system. In some embodiments, the pharmaceutical composition comprises a solid adsorption carrier selected from: silicon dioxide, calcium aluminometasilicate, magnesium aluminometasilicate (e.g., Veegum®), and a layered 2:1 phyllosilicate. In some embodiments, the layered 2:1 phyllosilicate is selected from: montmorillonite, nontronite, beidellite, volkonskoite, hectorite, saponite, sauconite, sobockite, stevensite, and svinfordite. In some embodiments, the pharmaceutical composition comprises one or more hydrocolloid as solid adsorption carrier and thickening agent selected from: starches, cellulose esters (sodium carboxymethylcellulose, methyl cellulose, hydroxyethylcellulose, hydroxypropylmethylcellulose and microcrystalline cellulose), gums (guar gum, xanthan gum, gum arabic), gelatin, alginates, carrageenan and pectin. In some embodiments, the testosterone ester is testosterone undecanoate. In some embodiments, the pharmaceutical composition comprises testosterone undecanoate, peppermint oil, oleic acid, and Cremophor® RH40. In some embodiments, the pharmaceutical composition comprises testosterone undecanoate, peppermint oil, oleic acid, Cremophor® RH40, Neusilin® US2, croscarmellose sodium, and magnesium stearate. In some embodiments, the pharmaceutical composition comprises testosterone undecanoate, peppermint oil, oleic acid, Cremophor® RH40, copovidone, maltodextrin, and microcrystalline cellulose.

One aspect of the present invention is directed to pharmaceutical products as described herein, comprising a first pharmaceutical composition comprising a hypolipidemic agent that increases the plasma concentration of one or more HDL particle subclasses in an individual; and a second pharmaceutical composition comprising a testosterone ester. In some embodiments, the testosterone ester is testosterone undecanoate. In some embodiments, the second pharmaceutical composition comprises 18 to 22 percent by weight of a solubilized testosterone undecanoate. In some embodiments, the testosterone undecanote is solubilized in a carrier substantially free of ethanol. In some embodiments, the second pharmaceutical composition comprises 15 to 17 percent by weight of the at least one hydrophilic surfactant. In some embodiments, the second pharmaceutical composition 50 to 55 percent by weight of the at least one lipophilic surfactant. In some embodiments, the second pharmaceutical composition comprises a solid adsorption carrier selected from: silicon dioxide, calcium aluminometasilicate, magnesium aluminometasilicate, and a layered 2:1 phyllosilicate. In some embodiments, the second pharmaceutical composition comprises layered 2:1 phyllosilicate is selected from: montmorillonite, nontronite, beidellite, volkonskoite, hectorite, saponite, sauconite, sobockite, stevensite, and svinfordite. In some embodiments, the second pharmaceutical composition comprises testosterone undecanoate, peppermint oil, oleic acid, and Cremophor® RH40. In some embodiments, the second pharmaceutical composition comprises testosterone undecanoate, peppermint oil, oleic acid, Cremophor® RH40, Neusilin® US2, croscarmellose sodium, and magnesium stearate. In some embodiments, the second pharmaceutical composition testosterone undecanoate, peppermint oil, oleic acid, Cremophor® RH40, copovidone, maltodextrin, and microcrystalline cellulose.

One aspect of the present invention is directed to methods of treating testosterone deficiency or its symptoms comprising orally administering to an individual suffering from testosterone deficiency or its symptoms an effective amount of one or more pharmaceutical compositions described herein. In some embodiments, the one or more pharmaceutical compositions are administered once daily. In some embodiments, the one or more pharmaceutical compositions are administered twice daily.

One aspect of the present invention is directed to methods of treating testosterone deficiency or its symptoms comprising orally administering to an individual suffering from testosterone deficiency or its symptoms an effective amount of one or more pharmaceutical compositions described herein, wherein the method gives rise to a $C_{max}$ value in the individual falling in the range of about 900 to 1100 ng/dL.

One aspect of the present invention is directed to methods of treating testosterone deficiency or its symptoms comprising orally administering to an individual suffering from testosterone deficiency or its symptoms an effective amount of one or more pharmaceutical compositions described herein, wherein the one or more pharmaceutical compositions are administered to the individual with a meal comprising at least 20 wt % fat.

One aspect of the present invention is directed to methods of treating testosterone deficiency or its symptoms comprising orally administering to an individual suffering from testosterone deficiency or its symptoms an effective amount of one or more pharmaceutical compositions described herein, which gives rise to substantially no diurnal testosterone pharmacokinetic variation in the individual.

One aspect of the present invention is directed to methods of treating testosterone deficiency or its symptoms comprising orally administering to an individual suffering from testosterone deficiency or its symptoms an effective amount of the one or more pharmaceutical compositions described herein, which gives rise to an average serum testosterone $T_{max}$ value in the individual falling in the range of about 3 to 7 hours after oral administration. In some embodiments, the average serum $T_{max}$ value falls in the range of about 4 to 5 hours after oral administration to the individual.

One aspect of the present invention is directed to methods of treating testosterone deficiency or its symptoms comprising orally administering to an individual suffering from testosterone deficiency or its symptoms an effective amount of the one or more pharmaceutical compositions described herein, in which substantially no significant decline in steady state serum testosterone response is observed in the individual upon repeat dosing to the individual.

One aspect of the present invention is directed to pharmaceutical products comprising one or more pharmaceutical compositions as described herein for use in a method of treatment of the human or animal body by therapy. One aspect of the present invention is directed to pharmaceutical products comprising one or more pharmaceutical compositions as described herein for use in a method of treating testosterone deficiency or its symptoms. In some embodiments, the one or more pharmaceutical compositions are administered once daily. In some embodiments, the one or more pharmaceutical compositions are administered twice daily. In some embodiments, administration of the one or more pharmaceutical compositions to an individual, gives rise to a testosterone $C_{max}$ value in the individual falling in the range of about 900 to 1100 ng/dL. In some embodiments, the one or more pharmaceutical compositions are administered to the individual with a meal comprising at least 20 wt % fat. In some embodiments, administration of the one or more pharmaceutical compositions to an individual, gives rise to substantially no diurnal testosterone pharmacokinetic variation in the individual. In some embodiments, administration of the one or more pharmaceutical compositions to an individual, gives rise to an average serum testosterone $T_{max}$ value in the individual falling in the range of about 3 to 7 hours after oral administration to the individual. In some embodiments, the average serum $T_{max}$ value in the individual falls in the range of about 4 to 5 hours after oral administration. In some embodiments, substantially no significant decline in steady state serum testosterone response is observed in the individual upon repeat dosing to the individual.

In a preferred embodiment of the present invention, pharmaceutical product is provided comprising a hypolipidemic agent and a pharmaceutical composition comprising: (a) 15-25 percent by weight of a solubilized testosterone undecanoate; (b) 12-18 percent by weight of at least one hydrophilic surfactant; (c) 50-65 percent by weight of at least one lipophilic surfactant; (d) 10-15 percent by weight of a mixture of borage oil and peppermint oil, which composition may be free of monohydric alcohols generally, specifically, ethanol and, upon oral administration to an individual in need thereof, gives rise to a serum testosterone half-life ($T_{1/2}$) falling in the range of about 10 hours to about 18 hours. Cremophor® RH40 is a preferred hydrophilic surfactant and a preferred lipophilic surfactant is oleic acid. Borage oil and peppermint oil are both considered lipophilic surfactants.

In a particularly preferred embodiment, the pharmaceutical composition comprises: (a) 18-22 percent by weight of a solubilized testosterone undecanoate; (b) 15-17 percent by weight of at least one hydrophilic surfactant; (c) 50-55 percent by weight of at least one lipophilic surfactant; and; (d) 10-15 percent by weight of a mixture of borage oil and peppermint oil. The ratio of borage oil to peppermint oil may range from 8:1 to 3:1; preferably from 6:1 to 5:1; most preferably from 5:1 to 4:1. In addition, to Cremophor® RH40, Solutol® HS-15, Tween® 80 and TPGS are preferred hydrophilic surfactants; and, in addition to oleic acid, glycerol mono-/di-oleate, propylene glycol mono-/di-laurate, and glycerol mono-/di-caprylate/caprate are preferred lipophilic surfactants. Combinations of two or more lipophilic surfactants and two or more hydrophilic surfactants are also contemplated.

In another embodiment of the present invention, a method of treating testosterone deficiency is provided, the method comprising orally administering to a hypogonadal subject an effective amount of a hypolipidemic agent and a pharmaceutical composition comprising: (a) 15-25 percent by weight of a solubilized testosterone undecanoate; (b) 12-18 percent by weight of one or more hydrophilic surfactants; (c) 50-65 percent by weight of one or more lipophilic surfactants; (d) 10-15 percent by weight of a mixture of borage oil and peppermint oil, and free of ethanol, whose once- or twice-daily oral administration gives rise to an average (or a mean) steady state serum testosterone concentration, $C_{avg}$, falling in the range of about 300 and about 1100 ng/dL in the subject. The composition may optionally be administered with a meal whose fat content ranges from about 15 wt % to about 25 wt % or more. According to the method, any one or all of the following pharmacokinetic parameters may be achieved in the subject: (a) serum testosterone $C_{max}$ within 900 and 1100 ng/dL in the subject; (b) substantially no diurnal testosterone pharmacokinetic variation; (c) serum $T_{max}$ 3 to 7 hours after administering the composition; and (d) substantially no decline in steady state serum testosterone response is observed upon repeat dosing.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other moieties, methods and systems for carrying out the several purposes of the present invention. For example, some embodiments of the invention may combine a T ester and the hypolipidemic agent with other active drugs, including other hormones, in an oral delivery system that, in part, prevents or alleviates symptoms associated with testosterone deficiency. It is important, therefore, that the claims be regarded as including such equivalent constructions, which do not depart from the scope and spirit of the present invention.

DETAILED DESCRIPTION OF THE INVENTION

Figure 1:
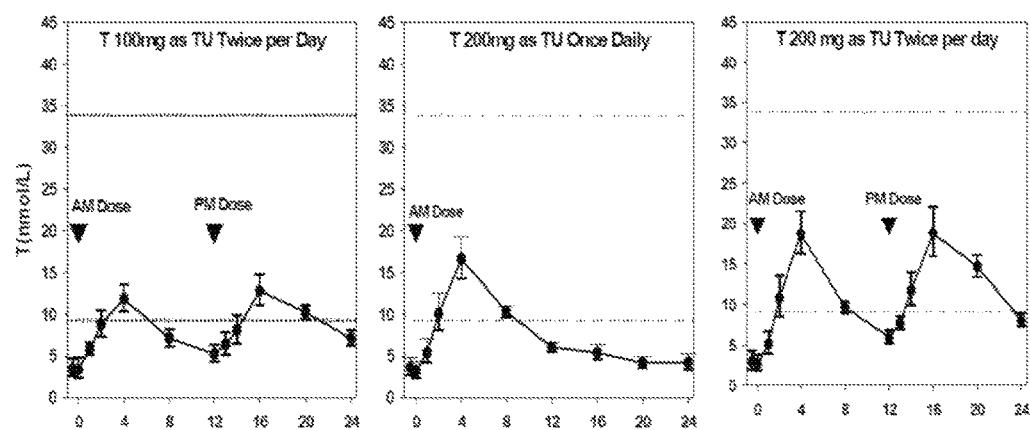
FIG. 1 provides serum T levels over a 24 hour period of once or twice daily oral dosing of a TU formulation described herein.

The present invention provides pharmaceutical products that include at least one hypolipidemic agent and a testosterone ester, and methods of using them. In some embodiments, the pharmaceutical product comprises a fixed-dose combination—a single formulation combining a hypolipidemic agent and a testosterone ester in a predetermined ratio. In some embodiments, the pharmaceutical product comprises a co-packaged product—a hypolipidemic agent in one formulation and a testosterone ester in a separate formulation, along with labeling to support their combined use. Two formulations in a co-packaged product may be administered simultaneously or sequentially. The present invention further provides methods of adjuvant therapy comprising prescribing or administering a hypolipidemic agent and a testosterone ester, to an individual in need thereof, in separate dosage forms in a ratio determined by a healthcare provider.

The fixed-dose combination formulations described herein comprise a hypolipidemic agent added to a testosterone ester formulation described herein. Such testosterone ester formulations may be modified as necessary or desirable due to the presence of the hypolipidemic agent, such as by increasing or decreasing the amount of the testosterone ester, altering the ratio of excipients, omitting one or more excipients, or including one or more additional excipients. Any mixing incompatibilities in fixed dose combinations may be overcome through the use of one or more of the following techniques well known in the art: bilayer, multilayer tablet-in-tablet, melt extruded granules, multigranule compressed tablets, particle coating, multiparticulates, and compartmentalized capsules. Such fixed-dose combinations may be prepared by methods of pharmacy well known to those skilled in the art (See, for example, Remington: The Science and Practice of Pharmacy, 21st ed., Lippincott Williams & Wilkins, Philadelphia, Pa. (2005)).

The co-packaged pharmaceutical products described herein comprise a hypolipidemic agent formulated, independently of the testosterone ester, into dosage forms suitable for oral administration. Formulations may be prepared by any suitable method, typically by uniformly mixing the active compound(s) with liquids or finely divided solid carriers, or both, in the required proportions and then, if necessary, forming the resulting mixture into a desired shape. Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. The co-packaged pharmaceutical products described herein may be prepared by methods of pharmacy well known to those skilled in the art (see, for example, Remington: The Science and Practice of Pharmacy, 21st ed., Lippincott Williams & Wilkins, Philadelphia, Pa. (2005)).

The pharmaceutical products of the present invention comprise a testosterone ester in an oral pharmaceutical composition, which when administered no more than twice a day to hypogonadal males, provides average steady state serum levels (concentrations) of testosterone in such males, which fall within a desired "normal" or eugonadal range (i.e., about 300-1100 ng/dL) while avoiding the high $C_{max}$ values that are considered by the United States Food and Drug Administration (FDA) to be undesirable, if not unacceptable. For instance FDA approval guidelines state that less than 85% of treated subjects may have a $C_{max}$ value of 1500 ng/dL or greater, and that none may have a $C_{max}$ value exceeding 2500 ng/dL. Less than 5% of treated subjects may have a $C_{max}$ value falling in the range of 1800-2500 ng/dL. Moreover, the testosterone ester formulations described herein are designed to be self-emulsifying drug delivery systems (SEDDS) so that a testosterone ester-containing emulsion (or dispersion) is formed upon mixing with intestinal fluids in the gastrointestinal tract.

SEDDS, as well as self-microemulsifying drug delivery systems (SMEDDS) and self-nanoemulsifying drug delivery systems (SNEDDS) form fine oil-in-water dispersions (emulsion, microemulsion, and nanoemulsion, respectively) upon dilution with aqueous media or in contact with gastrointestinal fluids. SEDDS dispersions i.e. emulsions are thermodynamically unstable and lipid droplets are heterogeneous in size ranging from 200 nm to 5 µm in diameter. SEDDS dispersions have a turbid appearance. SMEDDS dispersions i.e. microemulsions are thermodynamically stable and the droplet size is <200. nm. SMEDDS dispersions i.e. nanoemulsions have an optically clear to translucent appearance. SNEDDS produce kinetically stable nanoemulsion droplets <200 nm or more commonly <100 nm. SNEDDS dispersions have an optically clear appearance. The smaller the droplet size of the resulting oil-in-water droplets, the larger the surface area, which is advantageous for improved drug absorption through the portal route.

In one embodiment of the present invention, testosterone and/or esters at the C-17 position of the testosterone molecule and a hypolipidemic agent, alone or in combination with other active ingredients, may be orally delivered using the formulations described herein. For example, the combination of testosterone undecanoate and a hypolipidemic agent with an orally active inhibitor of Type I or Type II 5α-reductase or the combination of testosterone undecanoate and a hypolipidemic agent with a synthetic progestin may be preferable in some embodiments.

While many of the embodiments of the present invention will be described and exemplified with the undecanoate acid ester of testosterone (i.e., TU), other esters of lipophilic compounds, including T, can be adapted for oral delivery based on the teachings of the specification. In fact, it should be readily apparent to one of ordinary skill in the art from the teachings herein that the drug delivery systems and compositions therefrom described herein may be suitable for oral delivery of a hypolipidemic agent along with other testosterone esters, such as short-chain ($C_2$-$C_6$), medium-chain ($C_7$-$C_{13}$) and long-chain ($C_{14}$-$C_{24}$) fatty acid esters, preferably medium-chain fatty acid esters of testosterone.

Oral TU therapy leads to higher $C_{avg}$ values than therapy with T gel and a rapid (occurring as early as day 30) and sustained suppression of HDL in the 20% range (Example 7). HDL, cholesterol and triglycerides are important constituents of the lipid fraction of the human body. Cholesterol is an unsaturated alcohol of the steroid family of compounds; it is essential for the normal function of all animal cells and is a fundamental element of their cell membranes. It is also a precursor of various critical substances such as adrenal and gonadal steroid hormones and bile acids. Triglycerides are fatty acid esters of glycerol and represent the main lipid component of dietary fat and fat depots of animals. Cholesterol and triglycerides, being nonpolar lipid substances (insoluble in water), need to be transported in the plasma associated with various lipoprotein particles. Plasma lipoproteins are separated by hydrated density; electrophoretic mobility; size; and their relative content of cholesterol, triglycerides, and protein into five major classes: chylomicrons, very-low-density lipoproteins (VLDL), intermediate-density lipoproteins (IDL), low-density lipoproteins (LDL), and HDL. Since the levels of plasma lipids have a bell-shaped distribution in the general population, the definition of either a high or a low value of these substances has remained an arbitrary statistical decision. High values have been traditionally considered as those in the 90th and 95th percentiles; low values were considered to be those below the 5th percentile. The NIH Consensus Conference has recently revised the values concerning cholesterol, however, in view of clear evidence of an increased risk of coronary atherosclerosis in persons falling in the 75th to 90th percentiles. According to this last statement, cholesterol levels below 200 mg/dL are classified as "desirable blood cholesterol," those 200 to 239 mg/dL as "borderline-high blood cholesterol," and those 240 mg/dL and above as "high blood cholesterol (Cox et al. Clinical Methods: The History, Physical, and Laboratory Examinations. 3rd edition. Chapter 31: Cholesterol, Triglycerides, and Associated Lipoproteins).

A consensus statement from the National Lipid Association has proposed further classification of HDL particles according to their physical properties (Table 1) (Toth, P. P., et al., *J Clin Lipidol,* 2013. 7(5): p. 484-525).

| | Proposed Term | | | | |
|---|---|---|---|---|---|
| | Very Large (HDL-VL) | Large (HDL-L) | Medium (HDL-M) | Small (HDL-S) | Very Small (HDL-VS) |
| Density (g/mL) | 1.063-1.087 | 1.088-1.110 | 1.110-1.129 | 1.129-1.154 | 1.154-1.25 |
| Size (nm) | 12.9-9.7 | 9.7-8.8 | 8.8-8.2 | 8.2-7.8 | 7.8-7.2 |
| Density Gradient Ultracentrifugation Density (g/mL) | $HDL_{2b}$ 1.063-1.087 | $HDL_{2a}$ 1.088-1.110 | $HDL_{3a}$ 1.110-1.129 | $HDL_{3b}$ 1.129-1.154 | $HDL_{3c}$ 1.154-1.170 |
| Gradient Gel Electrophoresis Size (nm) | $HDL_{2b}$ 12.9-9.7 | $HDL_{2a}$ 9.7-8.8 | $HDL_{3a}$ 8.8-8.2 | $HDL_{3b}$ 8.2-7.8 | $HDL_{3c}$ 7.8-7.2 |
| 2D Gel Electrophoresis Size (nm) | a-1 11.2-10.8 | a-2 9.4-9.0 | a-3 8.5-7.5 | a-4 7.5-7.0 | preβ-1 HDL 6.0-5.0 |
| NMR | Large HDL-P | Medium HDL-P | | Small HDL-P | |

-continued

| | Proposed Term | | | | |
|---|---|---|---|---|---|
| | Very Large (HDL-VL) | Large (HDL-L) | Medium (HDL-M) | Small (HDL-S) | Very Small (HDL-VS) |
| Size range (nm) | 12.9-9.7 | 9.7-8.8 | 8.8-8.2 | 8.2-7.8 | 7.8-7.2 |
| Ion mobility 1 | $HDL_{ab}$ | $HDL_{2a} + HDL_3$ | $HDL_{3a}$ | $HDL_{3b}$ | $HDL_{3c}$ |
| Size (nm) | 14.5-10.5 | 10.5-7.65 | 8.8-8.2 | 8.2-7.8 | 7.8-7.2 |

Structure—function analysis has revealed that the HDL lipidome may strongly affect atheroprotective functionality (Camont, et al., *Arterioscler Thromb Vasc Biol.* 2013; 33:00-00). Our understanding of the relationship between the atheroprotective activities of HDL and heterogeneity of HDL particles has advanced greatly. HDL particles are highly heterogeneous in structure, intravascular metabolism and antiatherogenic activity. Small, dense HDL possesses potent antioxidative activity but this is compromised under conditions of atherogenic dyslipidemia. HDL functional deficiency frequently coincides with reductions in HDL-cholesterol concentration and alterations in HDL metabolism and structure. Formation of small, dense HDL particles with attenuated antiatherogenic activity can be mechanistically related to HDL enrichment in triglycerides and in serum amyloid A, depletion of cholesteryl esters, covalent modification of HDL apolipoproteins and attenuated anti-atherogenic function of apoA1. Low circulating levels of HDL cholesterol might, therefore, be associated with the defective functionality of small HDL particles of abnormal structure and composition. In common metabolic diseases, such as type 2 diabetes and metabolic syndrome, deficiency of HDL particle number and function favor accelerated atherosclerosis. Therapeutic normalization of the quantity, quality and biological activities of HDL particles thus represents a novel approach to attenuating atherosclerosis in dyslipidemic individuals with metabolic disease. Cholesteryl ester transfer protein inhibitors, nicotinic acid, reconstituted HDL and other HDL-raising agents are being investigated. Induction of selective increase in the circulating concentrations of small, dense $HDL_3$ particles with increased antiatherogenic activity seems especially promising, particularly for therapy of atherogenic dyslipidemia (Kontush and Chapman, *Nature Clinical Practice Cardiovascular Medicine*, March 2006, Vol. 3, No. 3).

Preβ-1 HDL, a very small HDL, is now recognized as the primary acceptor of cholesterol effluxed by the dominant ATP-binding cassette A1 (ABCA1) transporter in arterial macrophages, a critical step in reverse cholesterol transport. Preβ-1 HDL can be generated from $HDL_2$ by hepatic lipase. Bezafibrate, a PPARα agonist, is one of the fibric acid derivatives widely used to treat patients with hypertriglyceridemia and combined hyperlipidemia. Because bezafibrate increases lipase activity, it is highly possible that bezafibrate promotes conversion of $HDL_2$ to preβ-1 HDL. Such changes in the HDL subfractions may favor reverse cholesterol transport, an effect that might partly contribute to the anti-atherogenic action of bezafibrate (Miida et al., *Arterioscler Thromb Vasc Biol.* 2000; 20:2428-2433).

The pharmaceutical products described herein are useful for treating T deficiency and symptoms thereof, with concomitant administration of a hypolipidemic agent to mitigate any T-induced decreases in apoA1 and HDL. Hypolipidemic agents include niacin, statins (such as fluvastatin, simvastatin, and lovastatin), PPARα agonists, PPARδ agonists, and pan-PPAR agonists. Pan-PPAR agonists include aleglitazar, muraglitazar, saroglitazar, and tesaglitazar. PPARδ agonists include {4-[({4-methyl-2-[4-(trifluoromethyl)phenyl]-1,3-thiazol-5-yl}methyl)sulfanyl]-2-methylphenoxy}acetic acid (GW501516) and [4-[[[2-[3-fluoro-4-(trifluoromethyl)phenyl]-4-methyl-5-thiazolyl]methyl]thio]-2-methylphenoxy]-acetic acid (GW0742). Examples of selective PPARα agonists include fibric acid derivatives, such as aluminum clofibrate, beclobrate, bezafibrate, binifibrate, ciprofibrate, clinofibrate, clofibrate, clofibric acid, clofibride, dulofibrate, eniclobrate, ethofibrate, etofylline clofibrate, fenofibrate, fenofibric acid, gemfibrozil, nicofibrate, pirifibrate, ronifibrate, simfibrate, and theofibrate. PPARα agonists have been shown to improve cardiovascular outcome to various degrees through a number of mechanism that affect both LDL and HDL.

In the VA-HIT 2,531 men with CHD, low HDL-C (≤40 mg/dL) and moderately elevated LDL-C (≤140 mg/dL), were randomized to receive gemfibrozil 600 mg twice daily or placebo for 5 years. Participants were included if their triglyceride level was ≤300 mg/dL or 3.38 mmol/L. The primary outcome in this trial was nonfatal myocardial infarction or death of cardiac origin. A primary event occurred in 21.7% of those receiving placebo versus 17.3% receiving gemfibrozil for a relative risk reduction of 22% (95% CI 7-35, p=0.006). The relative risk reduction for combined cardiac events (nonfatal MI, death from coronary causes or stroke) with gemfibrozil was 24% compared to placebo (95% CI 11-36, p<0.001). An increase in apoA1 gene transcription and production, and an increase in apoA1 fractional catabolic rate, indicated an increase in apoA1 turnover usually associated with a positive impact on reverse cholesterol transport. The authors concluded that raising HDL-C and lowering triglycerides with gemfibrozil, without lowering LDL-C, reduced major CHD events (Rubins et al., N Engl J Med 1999; 341:410-418).

In a recent meta-analysis the average rise in HDL levels across a number of PPARα agonists is about 8%. This effect opposes the decrease in apoA1 production induced by TRT.

A second effect that enhances this known positive effect on reverse cholesterol transport comes from HDL fractionation studies where all fibrates studied so far selectively increase $HDL_3$ (a subfraction of the HDL particle spectrum; density: 1.125-1.21 g/mL; diameter 6-9 nm). This subfraction is home to preβ-1 HDL and nascent poorly lapidated HDL which have very high affinity for cholesterol removal from macrophages through the ABCA1 receptor. All of the beneficial effect of gemfibrozil in the VA-HIT is solely derived from the increase in the $HDL_3$ sub-fraction. Fibrates, like T increase the activity of hepatic lipase leading to hydrolysis of the triglyceride-rich $HDL_2$ subfraction (density: 1.063-1.125 g/mL; diameter 8-11 nm) to lipid poor $HDL_3$.

In small studies, HDL fractionation by NMR shows bezafibrate to increase HDL levels by 20% and the smallest HDL fraction was increased by 167%. In another study, fenofibrate administration to hypertriglyceridemic patients increased HDL by 18% while the smallest HDL fraction was increased by 109%. Fenofibrate in a separate study was also shown to increase the level preβ-1 HDL by 50% after 6 months of therapy, and using a different sub-fractionation method, an increase in small HDL particles of 18% was measured. Aside from these effects fibrates also increase levels of both SR-B1 and ABCA1 receptors.

U.S. Pat. No. 8,481,084 discloses combinations of cholesterol-interacting layered phyllosilicates with other hypolipidemic agents for the treatment of hypercholesteremia. Silicates in general, including layered phyllosilicates, are used as viscosity modifiers (thickening agents) in pharmaceutical dosage forms, such as suspensions, capsules and tablets. Silicates are also used as solid adsorbents to convert liquid SEDDS into free flowing powders (solid SEDDS) which can be filled into capsules or compressed into tablets along with other solid dose excipients, such as, fillers, diluents and lubricants. Direct adsorption of drugs onto layered phyllosilicates can provide sustained/controlled release of the incorporated drug. Layered phyllosilicates reduce the absorption of dietary cholesterol by interacting directly with cholesterol and/or bile salts and also by increasing the viscosity of the intestinal fluids and thus reducing the diffusion of cholesterol in the intestine. Layered phyllosilicates can be incorporated into dosage forms of oral testosterone esters including SEDDS with or without a further cholesterol-reducing agent. In some embodiments, the pharmaceutical product of the present invention comprises a testosterone ester and a hypolipidemic agent comprising a homoionic hydrogen ion-exchanged layered phyllosilicate material and a further cholesterol-reducing agent selected from: niacin, statins, PPARα agonists, PPARδ agonists, and pan-PPAR agonists. In some embodiments the pharmaceutical product of the present invention comprises a testosterone ester and a hypolipidemic agent comprising a homoionic hydrogen ion-exchanged layered phyllosilicate material and a PPARα agonist. Preferred swellable layered materials are phyllosilicates of the 2:1 type having a negative charge on the layers ranging from about 0.15 to about 0.9 charges per formula unit and a commensurate number of exchangeable metal cations in the 25 interlayer spaces. Most preferred layered materials are smectite clay minerals such as montmorillonite, nontronite, beidellite, volkonskoite, hectorite, saponite, sauconite, sobockite, stevensite, and svinfordite.

HPMC soluble fiber of different viscosity grades, especially high-viscosity grades, have shown to significantly lower cholesterol at well tolerated doses in mildy hepercholesterolemic human subjects (Reppas et al; *Eur. J. Clin. Nutr.* (2009); 63: 71-77). HPMC and other cellulose esters as discussed above can be included in the pharmaceutical T-ester compositions as thickening agents and oral adsorbents which can further act as synergistic hypolipidemic agents.

The pharmaceutical compositions of the present invention may further comprise plant sterols/stanols, for example sitosterols and sitostanols as synergistic hypolipidemic agents (Vanstone et al; Unesterified plant sterols and stanols, lower LDL-cholesterol concentrations equivalently in hypercholesterolemic persons, *Am J Clin. Nutr.* 2002; 76:1272-1278,). In addition to their cholesterol lowering ability, sitosterols/sitostanols can also enhance T-ester solubility in oils and surfactants as disclosed in US2011/0160168. The pharmaceutical products of the present invention comprise a T-ester dissolved in a mixture comprising one or more lipophilic surfactants and one or more hydrophilic surfactants. The T-ester is $C_3$-$C_{18}$ fatty acid ester, preferably a $C_{11-14}$ fatty acid ester and mixtures thereof. In a preferred embodiment of the present invention the T-ester is Testosterone Undecanoate. A lipophilic surfactant as defined herein has a hydrophilic-lipophilic balance (HLB) value of less than 10, and preferably less than 5. A hydrophilic surfactant as defined herein has an HLB value of greater than 10. (HLB is an empirical expression for the relationship of the hydrophilic and hydrophobic groups of a surface active amphiphilic molecule, such as a surfactant. It is used to index surfactants and its value varies from about 1 to about 45 and includes both non-ionic and ionic surfactants. The higher the HLB, the more water soluble/dispersible the surfactant.)

According to one aspect of the present invention, each of the components of the testosterone ester delivery system (i.e., the lipophilic and hydrophilic surfactants) individually have solubilizing characteristics and contribute, in part, to solubilizing the testosterone ester. Those lipophilic surfactants that contribute substantially to dissolving the testosterone ester are defined herein as "primary" solvent(s). It should be appreciated, however, that solubility can be affected by the temperature of the solvent/formulation. In the formulations described herein comprising, for example, surfactants and TU in a ratio of about 4:1, the TU remains soluble at or above 30° C., including in the range of 30 to about 40° C.

A hydrophilic surfactant component may be necessary to achieve desirable dispersability of the testosterone ester formulation in the GI tract and release of the testosterone ester. That is, a hydrophilic surfactant, in addition to serving as a secondary solvent, may be required to release the testosterone ester from within the lipid carrier matrix, or primary solvent. In this respect, a high HLB surfactant, such as Cremophor® RH40, can generally suffice. The levels (amounts) of the high HLB surfactant can be adjusted to provide optimum testosterone ester release without compromising the solubilization of the testosterone ester.

Lipophilic surfactants suitable in pharmaceutical products of the present invention include:

Fatty acids ($C_6$-$C_{24}$, preferably $C_{10}$-$C_{24}$, more preferably $C_{14}$-$C_{24}$), saturated, for example, octanoic acid, decanoic acid, undecanoic acid, lauric acid, myristic acid, palmitic acid, stearic acid, unsaturated, for example, oleic acid, linoleic acid, and linolenic acid, and mixtures thereof. Oleic acid (cis-9-octadecanoic acid) is preferred.

Mono- and/or di-glycerides of fatty acids, such as Imwitor® 988 (glyceryl mono-/di-caprylate), Imwitor® 742 (glyceryl mono-/di-caprylate/caprate), Imwitor® 308 (glyceryl mono-caprylate), Imwitor® 191 (glyceryl mono-stearate), Softigen® 701 (glyceryl mono-/di-ricinoleate), Capmul® MCM (glyceryl mono-/di-caprylate/caprate), Capmul® MCM(L) (liquid form of Capmul® MCM), Capmul® GMO (glyceryl mono-oleate), Capmul® GDL (glyceryl dilaurate), Maisine™ (glyceryl mono-linoleate), Peceol™ (glyceryl mono-oleate), Myverol™ 18-92 (distilled monoglycerides from sunflower oil) and Myverol™ 18-06 (distilled monoglycerides from hydrogenated soybean oil), Precirol® ATO 5 (glyceryl palmitostearate) and Gelucire® 39/01 (semi-synthetic glycerides, i.e., $C_{12-18}$ mono-, di- and tri-glycerides). The preferred members of this class of lipophilic surfactants are the partial glycerides of oleic, palmitic and stearic acids and blends thereof.

Acetic, succinic, lactic, citric and/or tartaric esters of mono- and/or di-glycerides of fatty acids, for example, Myvacet™ 9-45 (distilled acetylated monoglycerides), Miglyol 829 (caprylic/capric diglyceryl succinate), Myverol™ SMG (mono/di-succinylated monoglycerides), Imwitor®

370 (glyceryl stearate citrate), Imwitor® 375 (glyceryl monostearate/citrate/lactate) and Crodatem T22 (diacetyl tartaric esters of monoglycerides).

Propylene glycol mono- and/or di-esters of fatty acids, for example, Lauroglycol™ (propylene glycol monolaurate), Mirpyl (propylene glycol monomyristate), Captex® 200 (propylene glycol dicaprylate/dicaprate), Miglyol® 840 (propylene glycol dicaprylate/dicaprate) and Neobee® M-20 (propylene glycol dicaprylate/dicaprate).

Polyglycerol esters of fatty acids such as Plurol® oleique (polyglyceryl oleate), Caprol® ET (polyglyceryl mixed fatty acids) and Drewpol® 10.10.10 (polyglyceryl oleate).

Castor oil ethoxylates of low ethoxylate content (HLB<10) such as Etocas™ 5 (5 moles of ethylene oxide reacted with 1 mole of castor oil) and Sandoxylate 5 (5 moles of ethylene oxide reacted with 1 mole of castor oil).

Acid and ester ethoxylates formed by reacting ethylene oxide with fatty acids or glycerol esters of fatty acids (HLB<10) such as Crodet 04 (polyoxyethylene (4) lauric acid), Cithrol™ 2MS (polyoxyethylene (2) stearic acid), Marlosol® 183 (polyoxyethylene (3) stearic acid) and Marlowet® G12DO (glyceryl 12 EO dioleate). Sorbitan esters of fatty acids, for example, Span™ 20 (sorbitan monolaurate), Crill™ 1 (sorbitan monolaurate) and Crill™ 4 (sorbitan mono-oleate).

Transesterification products of natural or hydrogenated vegetable oil triglyceride and a polyalkylene polyol (HLB<10), e.g. Labrafil® M1944CS (polyoxyethylated apricot kernel oil), Labrafil® M2125CS (polyoxyethylated corn oil) and Gelucire® 37/06 (polyoxyethylated hydrogenated coconut). Labrafil® M1944CS is preferred.

Alcohol ethoyxylates (HLB<10), e.g. Volpo™ N3 (polyoxyethylated (3) oleyl ether), Brij™ 93 (polyoxyethylated (2) oleyl ether), Marlowet® LA4 (polyoxyethylated (4) lauryl ether).

Pluronics, for example, Polyoxyethylene-polyoxypropylene co-polymers and block co-polymers (HLB<10) e.g. Synperonic™ PE L42 (HLB=8) and Synperonic™ PE L61 (HLB=3).

Mixtures of suitable lipophilic surfactants, such as those listed above, may be used if desired, and in some instances are found to be advantageous.

Any pharmaceutically acceptable hydrophilic surfactant (i.e., having an HLB value greater than 10) may be used in the testosterone ester formulations described herein. Some non-limiting examples include:

Castor oil or hydrogenated castor oil ethoxylates (HLB>10), e.g. Cremophor® EL (polyoxyethylene (35) castor oil), Cremophor® RH40 (polyoxyethylene (40) hydrogenated castor oil), Etocas™ 40 (polyoxyethylene (40) castor oil), Nikkol HCO-60 (polyoxyethylene (60) hydrogenated castor oil), Solutol® HS-15 (polyethylene glycol 660 hydroxystearate), Labrasol® (caprylocaproyl macrogol-8 glycerides), α-tocopherol-polyethylene glycol-1000-succinate (TPGS) and ascorbyl-6 palmitate. Cremophor® RH40 is preferred.

Polyoxyethylene sorbitan fatty acid derivates, e.g. Tween® 20 (polyoxyethylene (20) monolaureate), Tween® 80 (polyoxyethylene (20) monooleate), Crillet™ 4 (polyoxyethylene (20) monooleate) and Montanox 40 (polyoxyethylene (20) monopalmitate). Tween® 80 (Polysorbate 80) is preferred.

Gelucires®, preferably Gelucire® 50/13 (PEG mono- and diesters of palmitic and stearic acids. (In reference to Gelucires®, the first number (i.e., 50) corresponds to the melting point of the material and the second (i.e., 13) to the HLB number.)

Fatty acid ethoxylates (HLB>10), e.g. Myrj™ 45 (polyoxyethylene (8) stearate), Tagat® L (polyoxyethylene (30) monolaurate), Marlosol® 1820 (polyoxyethylene (20) stearate) and Marlosol OL15 (polyoxyethylene (15) oleate). Myrj™ 45 is preferred.

Alcohol ethoxylates (HLB>10), e.g. Brij™ 96 (polyoxyethylene (10) oleyl ether), Volpo™ O15 (polyoxyethylene (15) oleyl ether), Marlowet® OA30 (polyoxyethylene (30) oleyl ether) and Marlowet® LMA20 (polyoxyethylene (20) $C_{12}$-$C_{14}$ fatty ether).

Polyoxyethylene-polyoxypropylene co-polymers and block co-polymers (HLB>10), that are commercially available under the trade name Pluronics® or poloxamers, such as poloxamers 188 and 407 also known as Synperonic™ PE L44 (HLB=16) and Synperonic™ F127 (HLB=22), respectively.

Anionic surfactants, e.g. sodium lauryl sulfate, sodium oleate and sodium dioctylsulfosuccinate.

Alkylphenol surfactants (HLB>10), e.g. Triton™ N-101 (polyoxyethylene (9-10) nonylphenol) and Synperonic™ NP9 (polyoxyethylene (9) nonylphenol).

As mentioned, in one aspect of the present invention, each of the components of the testosterone ester delivery system (i.e., the lipophilic and hydrophilic surfactants) individually has solvent characteristics and contributes, in part, to solubilizing the testosterone ester. In this way, without being bound by or limited to theory, the present invention does not require additional solvents, such as co-solvents, to solubilize the testosterone ester, but these may be optionally included in the inventive pharmaceutical products, systems and formulations.

Optional co-solvents suitable with the instant invention are, for example, water, short chain mono-, di-, and polyhydric alcohols, such as ethanol, benzyl alcohol, glycerol, propylene glycol, propylene carbonate, polyethylene glycol with an average molecular weight of about 200 to about 10,000, diethylene glycol monoethyl ether (e.g., Transcutol® HP), and combinations thereof. Preferably, such co-solvents, especially ethanol or other monoalkanols, are excluded altogether.

Additional oils that may be incorporated in embodiments of the present invention include complete glycerol triesters of medium chain ($C_7$-$C_{13}$) or long chain ($C_{14}$-$C_{22}$) fatty acids with low molecular weight (up to $C_6$) mono-, di- or polyhydric alcohols. Some examples of oils for use in this invention thus include: vegetable oils (e.g., soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond, borage, peppermint and apricot kernel oils) and animal oils (e.g., fish liver oil, shark oil and mink oil).

In other embodiments of the present invention, methods and pharmaceutical products for modulating (i.e., sustaining) the rate of available serum testosterone by incorporating component(s) that may biochemically modulate (1) testosterone ester absorption, (2) testosterone ester metabolism to T, and/or (3) metabolism of T to dihydrotestosterone (DHT). For example, the inclusion of medium to long chain fatty acid esters can enhance testosterone ester absorption. In this way, more testosterone esters may stave off hydrolysis in the gut and enter the blood stream. In other words, the fatty acid ester may competitively inhibit esterases that would otherwise metabolize the testosterone ester. Examples of other esters or combinations thereof include botanical extracts or benign esters used as food additives (e.g., propylparben, octylacetate and ethylacetate).

Other components that can modulate testosterone ester absorption include "natural" and synthetic inhibitors of 5α-reductase, which is an enzyme present in enterocytes and other tissues that catalyzes the conversion of T to DHT. Complete or partial inhibition of this conversion may both increase and sustain increases serum levels of T after oral dosing with a testosterone ester while concomitantly reducing serum DHT levels. Borage oil, which contains a significant amount of the 5α-reductase inhibitor, gamma-linolenic acid (GLA), is an example of a "natural" modulator of testosterone ester metabolism. Other than within borage oil, of course, GLA could be added directly as a separate component of a testosterone ester formulation described herein. Many natural inhibitors of 5α-reductase are known in the art (e.g., epigallocatechin gallate, a catechin derived primarily from green tea, and saw palmetto extract from berries of the *Serenoa repens* species), all of which may be suitable in the present invention. Non-limiting examples of synthetic 5α-reductase inhibitors suitable for use in the present invention include compounds such as finasteride, dutasteride and the like.

In addition to 5α-reductase inhibitors, the present invention contemplates the use of inhibitors of T metabolism via other mechanisms. One such point of inhibition may be the cytochrome P450 isozyme CYP3A4, which is present in enterocytes and in liver cells and thus capable of metabolizing testosterone. Accordingly, selected embodiments of the invention, include peppermint oil, which is known to contain components capable of inhibiting CYP3A4 activity.

Yet other optional ingredients which may be included in the compositions of the present invention are those which are conventionally used in oil-based drug delivery systems, e.g., antioxidants such as tocopherol, tocopherol acetate, ascorbic acid, butylhydroxytoluene (BHT), ascorbyl palmitate, butylhydroxyanisole and propyl gallate; pH stabilizers such as citric acid, tartaric acid, fumaric acid, acetic acid, glycine, arginine, lysine and potassium hydrogen phosphate; thickeners/suspending agents such as hydrogenated vegetable oils, beeswax, colloidal silicon dioxide, mannitol, gums, celluloses, silicates, bentonite; flavoring agents such as cherry, lemon and aniseed flavors; sweeteners such as aspartame, acesulfane K, sucralose, saccharin and cyclamates; etc.

The present inventors have learned that relative proportions of the one or more lipophilic surfactants and one or more hydrophilic surfactants can be critical to achieving the desired PK of the present invention. More specifically, the inventors have discovered a ratio of total lipophilic surfactant and total hydrophilic surfactant, which is not only able to solubilize a relatively large amount of T-ester (e.g., greater than 15%, 18%, 20%, 22%, or 25%) but one that is also able to provide optimum release of the T-ester from within the formulation. Preferably, the total oil (e.g., oleic acid+borage oil+peppermint oil, all of which are considered lipophilic surfactants) to hydrophilic surfactant ratio (w/w) falls in the range of about 6:1 to 1:1, 6:1 to 3.1, 6:1 to 3.5:1, or 6:1 to 4:1; and more preferably, from about 5:1 to 3:1, and most preferably, from about 4:1 to 3:1.

The following relative concentrations, by weight, are preferred (the percentages are based on the total weight of the testosterone ester formulation, not counting any hypolipidemic agent which may be present in the formulation):

Hydrophilic surfactant: 10-20%, more preferably 12-18%, and most preferably 15-17%.

Lipophilic surfactant: 50-70%, more preferably 50-65%, and most preferably 50-55%.

Other oils: 5-15%, more preferably 7-15%, and most preferably 10-13%

Testosterone Ester: 10-30%, more preferably 15-25%, and most preferably 18-22%.

The formulations comprising a testosterone ester described herein have self-emulsifying properties, forming a fine emulsion upon dilution with aqueous media or intestinal fluids in vivo. In other words, these formulations may have high surfactant and lipid content designed for optimum dispersion upon mixing with an aqueous medium. Qualitative description of the self-emulsification property of the testosterone ester formulations described herein can be visually observed during the dissolution of same in vitro. On the other hand, quantitative measurements may be taken of the particle size of the emulsified droplets using laser light scattering and/or turbidity measurements in the dissolution medium by UV/VIS spectrophotometer. Any of these methodologies are available and known to one of ordinary skill in the art.

The pharmaceutical compositions comprising a testosterone ester described herein are preferably liquid or semi-solid at ambient temperatures. Furthermore, these pharmaceutical compositions can be transformed into solid dosage forms through adsorption onto solid carrier particles, such as silicon dioxide, calcium or magnesium aluminometasilicate, and layered 2:1 phyllosilicates, such as montmorillonite, smectite clay minerals such as montmorillonite, nontronite, beidellite, volkonskoite, hectorite, saponite, sauconite, sobockite, stevensite, and svinfordite, to obtain free-flowing powders which can be either filled into hard capsules or compressed into tablets. See, e.g., US 2003/0072798, Aguzzi et al., *Applied Clay Science* 36 (2007) 22-36. Hence, the term "solubilized" herein, should be interpreted to describe an active pharmaceutical ingredient (API), which is dissolved in a liquid solution, or which is uniformly dispersed in a solid carrier. Also sachet type dosage forms can be formed and used.

The pharmaceutical products described herein comprise a testosterone ester that is solubilized in the presence of lipid surfactant excipients (e.g., any combination of the lipophilic and hydrophilic surfactants noted above). Accordingly, the melting point of the surfactants used is one factor that can determine whether the resulting composition will be liquid or semi-solid at ambient temperature. Particularly preferred testosterone ester compositions are liquid oral unit dosage forms, more preferably filled into hard or soft capsules, e.g. gelatin or non-gelatin capsules such as those made of cellulose, carrageenan, or pollulan. The technology for encapsulating lipid-based pharmaceutical preparations is well known to one of ordinary skill in the art. As the delivery systems and formulations comprising a testosterone ester described herein are not limited to any one encapsulation method, specific encapsulation techniques need not be discussed further.

The drug carrier systems and pharmaceutical preparations comprising a testosterone ester described herein may be prepared by conventional techniques for lipid-based drug carrier systems. In a typical procedure for the preparation of the preferred testosterone ester carrier systems, a lipophilic surfactant component is weighed out into a suitable stainless steel vessel and a hydrophilic surfactant component is then weighed and added to the container along with any additional components. In a preferred method, the hydrophobic testosterone ester may be first added to a lipophilic surfactant component (e.g., oleic acid) and completely dissolved before adding a hydrophilic surfactant component. In any case, mixing of the components may be effected by use of a homogenizing mixer or other high shear device and high temperature particularly when high melting point surfactants are used to ensure that all components are in homogenous liquid state before or after the addition of the testosterone ester.

In a situation in which testosterone ester is weighed and added to a combined lipid mixture, mixing is continued, preferably at high temperature, until a homogenous solution is prepared. The testosterone ester formulation may be de-aerated before encapsulation in either soft or hard capsules. In some instances the fill formulation may be held at elevated temperature using a suitable jacketed vessel to aid processing. Also, in some instances, the homogenous solution may be filtered (e.g., through a 5 micron filter) before filling into capsules.

Returning now to the delivery of testosterone, the pharmaceutical products of the present invention may be suitable for testosterone therapy. Testosterone is the main endogenous androgen in men. Leydig cells in the testes produce approximately 7 mg of testosterone each day resulting in serum concentrations ranging from about 300 to about 1100 ng/dL. Women also synthesize testosterone in both the ovary and adrenal gland, but the amount is about one-tenth that observed in eugonadal men. The majority (≥98%) of circulating testosterone is bound to sex hormone binding globulin and albumin and is biologically active only when released in the free form. The term "free" is thus defined as not being bound to or confined within, for example, biomolecules, cells and/or lipid matrices of the testosterone ester formulations described herein. Generally, "free" medicaments described herein refer to medicament that is accessible to metabolic enzymes circulating in serum.

While the present invention should not be limited to the delivery of testosterone or any particular ester thereof, TU has been found to offer unique chemical and physical characteristics that make its use preferable in some embodiments. The undecanoate acid ester of testosterone, in particular, can yield superior bioavailability to that found with other equivalent esters (e.g., TE).

What is more, the use of TU in the formulations described herein is associated with a substantially lower serum DHT to T ratio than has been reported for other forms of TRT—including oral formulations of TU (Table 2). Testosterone interacts with androgen receptors either directly or following its conversion to DHT via the action of 5α-reductase. DHT is a more potent androgen than testosterone and its elevated levels are thought by some scientists to increase the risk of prostate cancer.

TABLE 2

Comparison of Serum DHT and DHT:T Ratios Observed in Response to T-Replacement by Various Routes of Administration

| Form of Androgen Replacement/Dose | Length of Exposure | Avg. Serum DHT (ng/dL) | Avg. DHT:T Ratio | Multiple of Clarus DHT:T Ratio | Reference |
|---|---|---|---|---|---|
| Oral TU in SEDDS [200 mg T (as TU), BID] | 7-Days | 107 | 0.24 | 1 | |
| Oral TU in SEDDS [200 mg T (as TU), BID] | 30-Days | 109 | 0.25 | 1 | |
| Scrotal T-Patch (4-6 mg, QD) (Testoderm ®) | 8 years | 175 | 0.42 | 1.75 | Atkinson et al (1998)[1] |
| Transdermal T-Gel (5-10 g, QD) (AndroGel ®) | 3 years | 130-210 | 0.25-0.30 | 1-1.25 | Swerdloff et al (2000)[2], Wang et al (2004)[3] |
| Oral TU (Andriol) [50 mg T (as TU), BID] | Several Months | 93 | 0.40 | 1.7 | Houwing et al (2003)[4] |
| Oral TU (Andriol) [50 mg T (as TU), BID] | 10 years | 90 | 0.50 | 2.1 | Gooren et al (1994)[5] |

[1] Atkinson, LE, Chang, Y-L and Synder, PJ. (1998) Long-term experience with testosterone replacement through scrotal skin. In: Testosterone: Action, Deficiency and Substitution (Nieschlag, E and Behre, HM, eds). Springer-Verlag, Berlin, pp. 365-388.
[2] Swerdloff, RS, et a (2000). Long-term pharmacokinetics of transdermal testosterone gel in hypogonadal men. J. Clin. Endocrinol. Metab. 85: 4500-4510.
[3] Wang, C et al (2004). Long-term testosterone gel (AndroGel ®) treatment maintains beneficial effects on sexual function and mood, lean and fat mass and bone mineral density in hypogonadal men. J. Clin. Endocrinol. Metab. 89: 2085-2098.
[4] Houwing, NS et al (2003). Pharmacokinetic study in women of three different doses of a new formulation of oral testosterone undecanoate, Andriol Testocaps. Pharmcotherapy: 23: 1257-1265.
[5] Gooren, LJG (1994). A ten-year safety study of the oral androgen testosterone undecanoate. *J. Androl.* 15: 212-215.

Table 3 provides composition details of various formulations of TU. For calculation purposes, 1 mg of T is equivalent to 1.58 mg T-undecanoate.

The compositions details of Table 3 (mg/capsule and wt. percentage) are based on an approximate fill weight of 800 mg fill weight per '00' hard gelatin capsule, not counting any hypolipidemic agent which may be present in the formulation. However, at testosterone-ester amounts less than about 100 mg/capsule, the formulations may be proportionally adjusted for smaller total fill weights that would permit use of smaller hard gelatin capsules (e.g., size '0' or smaller size if needed).

As well, it should be apparent to one of ordinary skill in the art that many, if not all, of the surfactants within a category (e.g., lipophilic, hydrophilic, etc.) may be exchanged with another surfactant from the same category. Thus, while Table 3 lists formulations comprising oleic acid, one of ordinary skill in the art should recognize other lipophilic surfactants (e.g., those listed above) may be suitable as well. Similarly, while Table 3 lists formulations comprising Cremophor® RH40 (HLB=13), one of ordinary skill in the art should recognize other hydrophilic surfactants (e.g., those listed above) may be suitable. Borage oil, peppermint oil, BHT, and ascorbyl palmitate may be substituted for chemically similar substances or eliminated.

TABLE 3

Composition % w/w (mg/"00" capsule)[1]

| F. | TU | Oleic Acid | Cremophor ® RH40 | Borage Oil | Peppermint Oil | BHT | Ascorbyl Palmitate | Fill Wt. (mg)[2] |
|---|---|---|---|---|---|---|---|---|
| 1 | 20 (158) | 51 (413) | 16 (128.5) | 10 (80) | 2.5 (20) | 0.06 (0.5) | — | 800 |
| 2 | 15 (120) | 54.5 (436) | 18 (144) | 10 (80) | 2.5 (20) | 0.02 (0.2) | 0.8 (6.4) | 806.6 |
| 3 | 17 (136) | 52.5 (420) | 18 (144) | 10 (80) | 2.5 (20) | 0.02 (0.2) | 0.8 (6.4) | 806.6 |
| 4 | 19 (152) | 50.5 (404) | 18 (144) | 10 (80) | 2.5 (20) | 0.02 (0.2) | 0.8 (6.4) | 806.6 |
| 5 | 21 (168) | 50 (400) | 16.5 (132) | 10 (80) | 2.5 (20) | 0.02 (0.2) | 0.8 (6.4) | 806.6 |
| 6 | 23 (184) | 50 (400) | 14.5 (116) | 10 (80) | 2.5 (20) | 0.02 (0.2) | 0.8 (6.4) | 806.6 |
| 7 | 25 (200) | 50 (400) | 12.5 (100) | 10 (80) | 2.5 (20) | 0.02 (0.2) | 0.8 (6.4) | 806.6 |
| 8 | 16 (128) | 53.5 (428) | 18 (144) | 10 (80) | 2.5 (20) | 0.02 (0.2) | 0.8 (6.4) | 806.6 |
| 9 | 18 (144) | 51.5 (413) | 18 (144) | 10 (80) | 2.5 (20) | 0.02 (0.2) | 0.8 (6.4) | 806.6 |
| 10 | 22 (176) | 50 (400) | 15.5 (124) | 10 (80) | 2.5 (20) | 0.02 (0.2) | 0.8 (6.4) | 806.6 |
| 11 | 24 (192) | 50 (400) | 13.5 (108) | 10 (80) | 2.5 (20) | 0.02 (0.2) | 0.8 (6.4) | 806.6 |
| 12 | 15 (120) | 55.5 (444) | 17 (136) | 10 (80) | 2.5 (20) | 0.02 (0.2) | 0.8 (6.4) | 806.6 |
| 13 | 17 (136) | 53.5 (428) | 17 (136) | 10 (80) | 2.5 (20) | 0.02 (0.2) | 0.8 (6.4) | 806.6 |
| 14 | 19 (152) | 51.5 (412) | 17 (136) | 10 (80) | 2.5 (20) | 0.02 (0.2) | 0.8 (6.4) | 806.6 |
| 15 | 15 (120) | 56.5 (452) | 16 (128) | 10 (80) | 2.5 (20) | 0.02 (0.2) | 0.8 (6.4) | 806.6 |
| 16 | 17 (136) | 54.5 (436) | 16 (128) | 10 (80) | 2.5 (20) | 0.02 (0.2) | 0.8 (6.4) | 806.6 |
| 17 | 19 (152) | 52.5 (420) | 16 (128) | 10 (80) | 2.5 (20) | 0.02 (0.2) | 0.8 (6.4) | 806.6 |
| 18 | 21 (168) | 50.5 (404) | 16 (128) | 10 (80) | 2.5 (20) | 0.02 (0.2) | 0.8 (6.4) | 806.6 |
| 19 | 20 (160) | 50.5 (404) | 17 (136) | 10 (80) | 2.5 (20) | 0.02 (0.2) | 0.8 (6.4) | 806.6 |
| 20 | 20 (160) | 51.5 (412) | 16 (128) | 10 (80) | 2.5 (20) | 0.02 (0.2) | 0.8 (6.4) | 806.6 |
| 21 | 15 (120) | 57.5 (460) | 15 (120) | 10 (80) | 2.5 (20) | 0.02 (0.2) | 0.8 (6.4) | 806.6 |
| 22 | 16 (128) | 56.5 (452) | 15 (120) | 10 (80) | 2.5 (20) | 0.02 (0.2) | 0.8 (6.4) | 806.6 |
| 23 | 17 (136) | 55.5 (444) | 15 (120) | 10 (80) | 2.5 (20) | 0.02 (0.2) | 0.8 (6.4) | 806.6 |
| 24 | 18 (144) | (54.5) (436) | 15 (120) | 10 (80) | 2.5 (20) | 0.02 (0.2) | 0.8 (6.4) | 806.6 |
| 25 | 19 (152) | 53.5 (428) | 15 (120) | 10 (80) | 2.5 (20) | 0.02 (0.2) | 0.8 (6.4) | 806.6 |
| 26 | 20 (158) | 51.5 (413) | 16 (128.5) | 9.4 (75) | 3.1 (25) | 0.06 (0.5) | — | 800 |
| 27 | 20 (158) | 51.5 (413) | 16 (128.5) | 10.6 (85) | 1.9 (15) | 0.06 (0.5) | — | 800 |
| 28 | 20 (158) | 51.5 (413) | 16 (128.5) | 11.2 (90) | 1.2 (10) | 0.02 (0.2) | 0.8 (6.4) | 806.1 |
| 29 | 20 (158) | 51.5 (413) | 16 (128.5) | 11.8 (95) | 0.6 (5) | 0.02 (0.2) | 0.8 (6.4) | 806.1 |
| 30 | 25 (200) | 50 (400) | 12.5 (100) | 10.6 (85) | 1.9 (15) | 0.06 (0.5) | — | 800.5 |

[1]Milligram weights rounded to nearest whole number; 800 (±10%) 2 ± 8 mg

Examples of formulations of TU filled into size "00" capsules are:

Formulation A

| Ingredients | mg/capsule | %, w/w |
|---|---|---|
| Testosterone Undecanoate | 158.3 | 19.8 |
| Oleic Acid | 413.1 | 51.6 |
| Cremophor RH 40 | 128.4 | 16.1 |
| Borage Seed Oil | 80.0 | 10 |
| Peppermint Oil | 20.0 | 2.5 |
| BHT | 0.2 | 0.03 |
| Total | 800 | 100 |

Formulation B

| Ingredients | mg/capsule | %, w/w |
|---|---|---|
| Testosterone Undecanoate | 158.3 | 19.8 |
| Oleic Acid | 412.5 | 51.6 |
| Cremophor RH 40 | 128.4 | 16.0 |
| Peppermint Oil | 20.0 | 2.5 |
| Borage Seed Oil + 0.03% BHT | 80.0 | 10 |
| Ascorbyl Palmitate | 0.8 | 0.1 |
| Total | 800 | 100 |

In vivo and in vitro performance data of the testosterone ester formulations are described below. However, the scope of the invention should not be limited by following examples nor the specific formulations studied in the examples.

EXAMPLES

Example 1—Single-Day Study

Formulation B was studied for its single-day PK profile upon once- or twice-daily administration to hypogonadal men. The study was designed as an open-label, single-day dosing, sequential, cross-over, PK study. Twelve (12) hypogonadal men were enrolled after giving written informed consent, and all 12 subjects completed the study. Each subject received a daily dose of Formulation B as follows:
1. 200 mg T (as TU) QD, i.e., 2 capsules/dose
2. 200 mg T (as TU) BID (100 mg/dose), i.e., 1 capsule/dose
3. 400 mg T (as TU) BID (200 mg/dose)

The doses were administered as capsules to subjects five minutes after a meal (breakfast for QD, and breakfast and dinner for BID).

Table 4 provides the relevant PK parameters from the study:

TABLE 4

Single-Day Pharmacokinetic Parameters for T, DHT, and DHT:T Ratio

| Pharmacokinetic Parameter (unit) | Means (Standard Deviations) of Pharmacokinetic Parameters[a] | | |
|---|---|---|---|
| | Regimen 1 (TU QD 200 mg[b]) | Regimen 2 (TU BID 100 mg[b]) | Regimen 3 (TU BID 200 mg[b]) |
| T | | | |
| $AUC_{24}$ (ng · hr/dL) | 5907 (1840) | 6751 (2145) | 9252 (3173) |
| $C_{avg}$ (ng/dL) | 246 (77) | 281 (89) | 385 (132) |
| $T_{1/2}$ (hr)[a] | 15.5 (7.0-24.0) | 15.1 (4.5-43.4) | 8.0 (4.2-16.3) |
| $C_{max}$ (ng/dL) | 0-24 hrs: 557 (252) | 0-12 hrs: 470 (247) 12-24 hrs: 466 (160) | 0-12 hrs: 626 (267) 12-24 hrs: 718 (333) |
| $T_{max}$ (hr)[a] | 0-24 hrs: 4.0 (2.0-8.0) | 0-12 hrs: 4.0 (2.0-12.0) 12-24 hrs: 16.0 (14.0-20.0) | 0-12 hrs: 4.0 (2.0-12.0) 12-24 hrs: 16.0 (14.0-20.0) |
| DHT | | | |
| $AUC_{24}$ (ng · hr/dL) | 1097 (387) | 1400 (758) | 1732 (859) |
| $C_{avg}$ (ng/dL) | 45.7 (16.1) | 58.3 (31.6) | 72.2 (35.8) |
| $C_{max}$ (ng/dL) | 0-24 hrs: 122 (66) | 0-12 hrs: 81.3 (40.3) 12-24 hrs: 97.9 (51.2) | 0-12 hrs: 108 (59) 12-24 hrs: 114 (58) |
| $T_{max}$ (hr)[a] | 0-24 hrs: 4.0 (1.0-8.0) | 0-12 hrs: 4.0 (1.0-12.0) 12-24 hrs: 16.0 (13.0-20.0) | 0-12 hrs: 4.0 (1.0-12.0) 12-24 hrs: 16.0 (14.0-20.0) |
| DHT:T Ratio | | | |
| $R_{avg}$ (ng/dL) | 0.189 (0.070) | 0.233 (0.137) | 0.198 (0.041) |

[a]Values shown for half-life and time to maximum concentration are median and the range.
[b]Doses indicated are in T equivalents. Each TU capsule contained 158.3 mg TU, which corresponds to 100 mg T equivalents.

Mean serum T concentration during the 24-hour period post-dose ($C_{avg}$) indicated positive increases in serum T levels for all regimens studied, with the best response obtained in Regimen 3 ($C_{avg}$ 385 ng/dL). Mean peak serum T concentration observed in response to the oral T-ester preparations evaluated in this study never exceeded the upper limit of normal (i.e., 1100 ng/dL). And while some individual subjects did have $C_{max}$ T values above the normal upper limit, the vast majority of these peaks were in the range of 1200 to 1400 ng/dL. No subject in any treatment arm experienced a $C_{max}$ in excess of 1500 ng/dL.

Median serum T half-life ($T_{1/2}$) was approximately 15 hours for Regimens 1 and 2; for Regimen 3, $T_{1/2}$ was 8 hours. In each regimen, serum DHT concentrations increased in concert with serum T levels. The mean DHT:T ratios ($R_{avg}$) in all periods were modestly above the normal ranges as determined by liquid chromatography-mass spectroscopy (LC/MS/MS) (i.e., 0.03-0.1), but were clinically insignificant.

TU dosed at 200 mg T equivalents, BID with food yielded the most promising results with 75% of the subjects achieving a serum T $C_{avg}$ above 300 ng/dL (lower normal eugonadal limit). Similarly, 75% of the subjects achieved an average serum T within the normal range (i.e., 0.03-0.1 ng/dL). Those subjects that did not achieve a $C_{avg}$ of at least 300 ng/dL were all above 200 ng/dL, indicating that a modest increase in the testosterone ester dose would have been effective oral T replacement therapy in these subjects.

Serum T and DHT concentrations increased in concert in the majority of subjects regardless of T-ester dose. Excellent dose linearity for oral TU was observed when data were corrected for serum T at baseline. Although DHT:T ratios were modestly elevated, any elevation was considered clinically insignificant. Less inter-subject variability was observed with the formulation than equivalent formulations of other T-esters (e.g., TE). Furthermore, in the "BID" dosing regimens, there was no difference in mean peak serum T concentrations or in the 12-hour AUCs between the morning and evening dose.

Concerning safety, although headache was reported as an adverse effect, in each treatment regimen, no adverse event was reported by more than one subject. No serious adverse events or deaths occurred during the study, and no subjects prematurely discontinued the study due to adverse events. Hence, all adverse events were considered to be of mild intensity.

Example 2—Seven-Day Study

Formulation B was studied for its acute tolerability and steady-state serum PK profile at two doses administered twice-daily to hypogonadal men. The study was designed as an open-label, repeat dose, cross-over, PK study (with food effect examined in one arm).

Twenty nine (29) hypogonadal men were enrolled after giving written informed consent, 24 of which completed the study. Each subject who completed the study received a regimen of Formulation B as follows:
1. 7 daily doses of 600 mg T as TU BID (300 mg/dose), i.e., 3 capsules/dose
2. 8 daily doses of 400 mg T as TU BID (200 mg/dose).

Doses were administered as capsules to subjects 30 minutes after initiation of meals (breakfast and dinner), except for Day 8, when the morning dose was administered fasting.

Peak exposure ($C_{max}$) to T and total exposure (AUC) to T were dose proportional after correction for the endogenous baseline T. The time of peak T concentrations ($T_{max}$) occurred at approximately 4 hours post-dose with each of the treatments. As well, the serum concentrations of both TU and DHTU rose and fell within the dosage interval with concentrations at the beginning and end of the dosing interval being less than 20% of the peak concentration for TU and less than 25% of the peak concentration for DHTU. Baseline T concentrations due to endogenous T production decreased progressively for each treatment. The observation is consistent with a progressive and persistent suppression of gonadotropins by exogenous T, thereby resulting in a decreased production of endogenous T. At least partial suppression was maintained over a 14-day washout period.

Again, serum T PK did not show diurnal variation with serum T concentrations. The night dose (administered at approximately 8 PM) produced a similar concentration-time profile as the morning dose (administered at approximately 8 AM) (FIG. 1). On account of the similarity between concentrations after AM and PM dosing (assessed in Regimen 1), 12-hour PK data from Regimen 2 (fed) were used to accurately predict a full 24-hour PK profile in response to 200 mg T (as TU), BID dosing. The simulated results indicated that (a) 77% of the subjects achieved a serum T $C_{avg}$ in the eugonadal range over the 24-hour period based on AUC thereby meeting the current FDA efficacy requirement of 75% for a T-replacement product; and (b) none of the subjects experienced a $C_{max}$ in excess of 1500 ng/dL, which is exceeds current FDA criterion that less than 85% of subjects have a $C_{max}$ of greater than 1500 ng/dL for a T-replacement product. Hence, also consistent with current FDA mandated efficacy endpoints, no subjects had a $C_{max}$ in excess of 2500 ng/dL and less than 5% of the subjects studied had a $C_{max}$ in the range of 1800-2500 ng/dL. It is noteworthy that these results were achieved in the absence of any dose adjustment.

Table 5 provides a comparison of steady state AM and PM pharmacokinetics of T with BID Dosing:

TABLE 5

|  | Treatment Regimen 1 300 mg T, as TU, BID | |
| --- | --- | --- |
|  | AM Dose Mean ± SEM | PM Dose Mean ± SEM |
| $C_{max}$ (ng/dL) | 1410 ± 146 | 1441 ± 118 |
| $T_{max}$ (hr, time after dose) | 4.50 ± 0.39 | 5.9 ± 0.5 |
| $C_{min}$ (ng/dL) | 305 ± 30 | 324 ± 36 |
| $AUC_{0-12}$ (ng · hr/dL) | 9179 ± 754 | 9830 ± 659 |
| $C_{avg}$ (ng/dL) | 765 ± 63 | 819 ± 55 |
| FI ratio | 1.37 ± 0.09 | 1.36 ± 0.09 |
| $C_{min}/C_{max}$ ratio | 0.256 ± 0.029 | 0.243 ± 0.022 |

Administration of TU with a high-fat meal produced a similar serum T-concentration-time profile as administration with a standard meal. In contrast, administration of TU under fasting conditions resulted in greater than 50% decrease in serum T exposures ($C_{max}$ and AUC). Table 6. In all cases, a strong correlation between the observed $C_{max}$ and the calculated $C_{avg}$ was observed, suggesting that targeting of a particular $C_{avg}$ with the oral T-ester formulation can result in predictable peak T levels after dosing.

TABLE 6

|  | After High Fat Breakfast | | While Fasting | | Geometric Mean of |
| --- | --- | --- | --- | --- | --- |
|  | Arithmetic Mean | Geometric Mean | Arithmetic Mean | Geometric Mean | Individual Ratios |
| $C_{max}$ (ng/dL) | 955 | 854 | 394 | 365 | 0.426 |
| $AUC_{0-12}$ (ng · hr.dL) | 6217 | 5682 | 2894 | 2692 | 0.471 |

Administration under fed conditions (high fat breakfast) was used as the reference DHT concentrations tracked T concentrations, although DHT concentrations were only 11-34% of the T concentrations. Conversion of T to DHT showed a slight nonlinearity, increasing at a less than a concentration-proportional rate compared to T. The DHT/T ratio was least when T concentrations were highest, and the DHT/T ratio prior to starting TU treatment was approximately 0.1, while during treatment, at steady-state, the mean ratio was 0.24 and ranged from approximately 0.1 to 0.35 depending on the time of sampling after oral TU was administered.

Mean estradiol concentration prior to starting the oral TU treatment was approximately 11 pg/mL, and ranged from 19 pg/mL to 33 pg/mL on Day 7 of the various treatments (pre-dose concentrations). Pre-dose steady-state estradiol concentrations were approximately 20-30 pg/mL.

Example 3—Four-Week Study

Formulation B was also studied to determine the time required to reach steady state when hypogonadal men are treated for 28 days with twice daily dosing of 200 mg T (as TU) (i.e., 2 capsules/dose). The study was designed as an open-label, repeat dose, PK study.

Fifteen (15) hypogonadal men were enrolled after giving written informed consent, and all completed the study. Each subject received twice-daily doses of 200 mg T as TU for 28 days.

For each subject, the "Day 28" serial PK sampling day was scheduled for Day 32 of the study. Therefore, each dose compliant subject received a total of 31 daily doses of 400 mg T as TU (i.e., 200 mg T, BID), and a final morning dose of 200 mg T as TU. Doses were administered as capsules, with subjects instructed to take doses 30 minutes after initiation of meals (breakfast and dinner).

Table 7 provides the relevant PK data from the study:

TABLE 7[A]

|  | T | DHT | DHT/T | $E_2$ |
|---|---|---|---|---|
| $C_{max}$ or $R_{max}$[b] | 995 ± 436 (43.9%) ng/dL | 151 ± 75 (49.5%) ng/dL | 0.380 ± 0.181 (47.7%) ratio | 30.6 ± 14.9 (48.7%) pg/mL |
| $T_{max}$ | 4.87 ± 1.96 (40.3%) hr | 5.87 ± 2.80 (47.7%) hr | 5.87 ± 6.02 (102.7%) hr | 6.67 ± 3.09 (46.3%) hr |
| $C_{min}$ or $R_{min}$[b] | 199 ± 108 (54.2%) ng/dL | 64.6 ± 47.6 (73.8%) ng/dL | 0.131 ± 0.047 (36.0%) ratio | 15.4 ± 9.2 (59.9%) pg/mL |
| $C_{avg}$ or $R_{avg}$[b] | 516 ± 226 (43.7%) ng/dL | 109 ± 61 (55.8%) ng/dL | 0.245 ± 0.077 (31.5%) ratio | 22.0 ± 10.9 (49.8%) pg/mL |
| $AUC_{0-12}$ | 6197 ± 2708 (43.7%) ng·hr/dL | 1312 ± 732 (55.8%) ng·hr/dL | 2.94 ± 0.93 (31.5%) hr | 264 ± 131 (49.8%) pg·hr/mL |
| $C_{min}/C_{max}$ or $R_{min}/R_{max}$b | 23.5% ± 16.2% (69.0%) % | 41.5% ± 17.0% (40.9%) % | 37.3% ± 11.5% (30.8%) % | 50.2% ± 15.1% (30.0%) % |
| Absolute Change in $C_{baseline}$[c] | −168 ± 188 (112.2%) ng/dL | 3.50 ± 16.80 (480.1%) ng/dL | 0.197 ± 0.116 (59.0%) ratio | −0.405 ± 5.345 (1320.8%) pg/mL |
| Percent Change in $C_{baseline}$[c] | −53.4% ± 79.5% (148.8%) % | 18.8% ± 95.0% (506.6%) % | 267% ± 170% (63.8%) (2224.6%) % | −1.9% ± 41.5% |
| Fluctuation Index | 156% ± 64% (40.8%) % | 84.7% ± 30.6% (36.1%) % | 96.0% ± 29.7% (30.9%) % | 74.5% ± 41.6% (55.9%) % |
| $\lambda_z$ | 0.0726 ± 0.0676 (93.1%) 1/hr | 0.0793 ± 0.0373 (47.1%) 1/hr | NA | 0.0544 ± 0.0176 (32.4%) 1/hr |
| $T_{1/2}$ | 29.0 ± 32.7 (112.8%) hr | 10.8 ± 5.8 (53.6%) hr | NA | 14.0 ± 5.3 (37.8%) hr |

[a] Results expressed as mean ± SEM. Co-efficient over variation is expressed as % in parentheses.
[b] $R_{max}$, $R_{min}$, $R_{avg}$ are the Maximum ratio, the Minimum ratio and the Time Averaged ratio, respectively for the DHT/T ratio (analogous to $C_{max}$, $C_{min}$ and $C_{avg}$)
[c] Change in Baseline determined as concentration (or ratio) in the final sample of Day 28 - concentration (or ratio) in the pre-treatment sample (Day 0).

86.7% of subjects achieved serum T $C_{avg}$ within the normal range, with no subjects having $C_{max}$ concentrations greater than 1800 ng/dL, and with just 13.3% of subjects having $C_{max}$ concentrations greater than 1500 ng/dL. (Note: No dosing adjustments were made during the conduct of this study to titrate subjects to be within the targeted efficacy and safety ranges.) The half-life of T in response to TU in the formulation tested was appreciably longer than has been reported for T alone or for other TU formulations given orally. For example, in clinical studies of an oral TU formulation consistent with the invention described herein, an elimination half-life (a phase) of about approximately 5 hours was observed compared to a value estimated to be roughly half that (i.e., 2 to 3 hours) based on published serum T profiles after oral dosing of an alternative formulation of TU. A long elimination (i.e., terminal) half-life of 29 hours was also observed with the inventive oral TU formulation. Endogenous T production was suppressed, however, by the administration of exogenous T, with only limited suppression occurring for the first 3 days, and requiring 5-7 days of continued treatment for maximal suppression.

Concentrations of T and DHT reached steady state by Day 7 of treatment. Concentrations of T and DHT were greater on Day 3 than on Day 5, indicating that a period of time was required for the exogenously administered T to suppress endogenous T production thus enabling achievement of steady-state in response to oral TU. Indeed, addition of the exogenous T suppressed endogenous T levels from 276 ng/dL pretreatment to 108 ng/dL after 28 days of supplementary T treatment.

Figure 2:
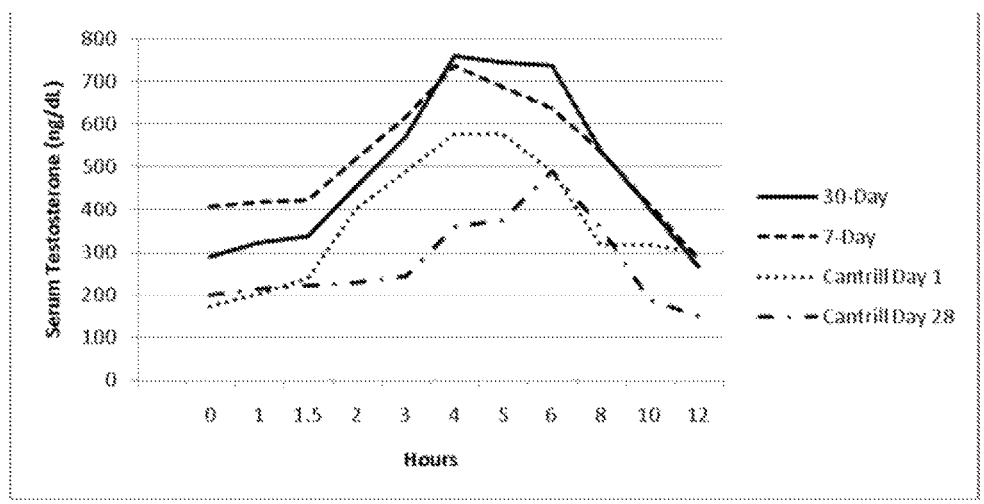
FIG. 2 shows a serum T response over time in hypogonadal men upon administration of a formulation described herein vs. a conventional oral TU formulation comprising TU in oleic acid (Restandol).

Significantly, however, once steady state was achieved for serum T in response to twice-daily oral TU, little to no decline in serum T response was observed over time (i.e., no trend toward lower serum T level with continued TU dosing). For example, the $C_{avg}$ at Day 15 was substantially similar to the $C_{avg}$ observed at day 28 (FIG. 2). By contrast, other oral TU formulations have been reported to trend toward a lower mean T over time (Cantrill, J. A. Clinical Endocrinol (1984) 21: 97-107). In hypogonadal men treated with different formulations of oral TU it has been reported that the serum T response observed after 4 weeks of therapy was about 30% less than that observed on the initial day of therapy in hypogonadal men, most of whom had a form of primary hypogonadism and thus low baseline levels of serum T (e.g., <100 ng/dL), so the decrease in T cannot be explained by suppression of endogenous T alone.

Serum DHT concentrations closely tracked T concentrations, with DHT and DHT/T values increasing 4 to 7 fold during treatment. Average DHT/T ratio over a 12-hour dosing interval was 0.245, although values over the dosing interval ranged from a mean maximum ratio of 0.380 to a mean minimum ratio of 0.131. DHT concentrations returned to pretreatment levels within 36 hours of discontinuing treatment with oral TU. However, T concentrations did not return to pretreatment levels as quickly, ostensibly because of the suppression of endogenous T production/release is not as rapidly reversed.

Concentrations of estradiol (E2) showed a monotonic, progressive increase to the steady state, which was also reached by Day 7 of treatment. E2 concentrations also showed systematic variation over the dosing interval that tracked the changes in T. The mean $C_{max}$, $C_{avg}$, and $C_{min}$ values for E2 were 30.6 pg/mL, 22.0 pg/mL and 15.5 pg/mL, respectively. E2 concentrations returned to pretreatment levels within 36 hours of discontinuing treatment with oral TU.

Mean $C_{max}$, $C_{avg}$, and $C_{min}$ concentrations at steady state (morning dose of Day 28) for T were 995 ng/dL, 516 ng/dL and 199 ng/dL, respectively. Median $T_{max}$ for T occurred at 5.0 hours post dose. $C_{min}$ averaged 23.5% of $C_{max}$, resulting in a Fluctuation Index of 156%. The elimination half-life of T could only be evaluated in about half the subjects, and its median value in those subjects was 18.4 hours (mean $T_{1/2}$ was 29 hours).

Example 4—Food Effects Study

Any effect of dietary fat on the PK of Formulation B in hypogonadal men was studied in an open-label, two-center, five-way crossover study. After a washout period of 4-10 days, a single dose of 300 mg of T (475 mg TU, 3 capsules of Formulation B) was administered to sixteen hypogonadal men with serum baseline T level of 205.5±25.3 ng/dL (mean±SE, range 23-334.1 ng/dL). Subjects were randomized to receive the drug in the fasting state or 30 minutes after consumption of meals containing ~800 calories with specific amounts of fat (wt %): very low fat (6-10%); low fat (20%); "normal" diet fat (30%); or high fat (50%). The "normal" diet was, a priori, established as the comparator (i.e., reference diet) for purposes of statistical comparisons. Serial blood samples were collected for a total of 24 hours after drug administration to determine serum testosterone and dihydrotestosterone (DHT) levels by liquid chromatography-mass spectroscopy (LC/MS/MS).

Figure 3:
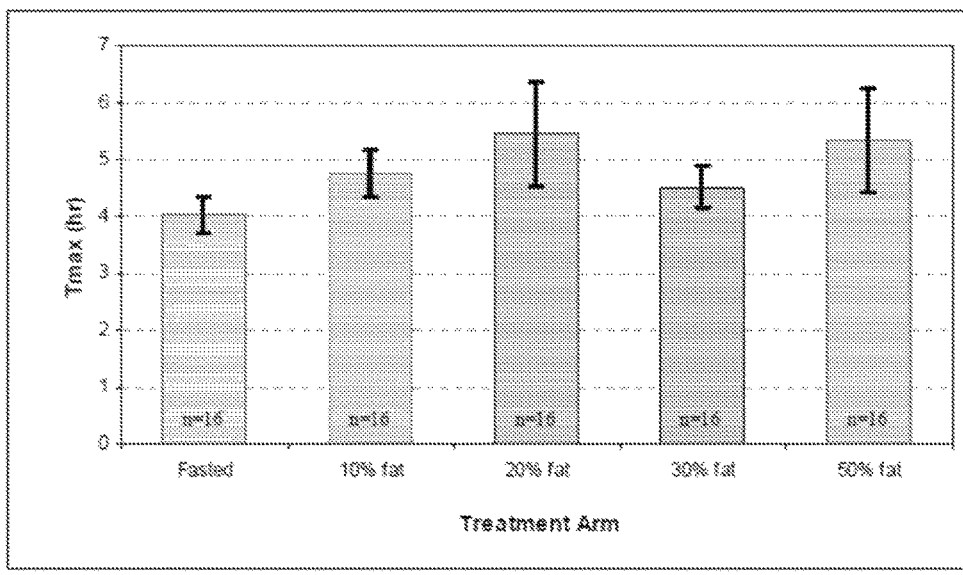
FIG. 3 provides $T_{max}$ values of serum T levels in subjects having consumed meals of varying fat content (as a percentage by weight) prior to oral administration of a TU formulation described herein.
Figure 4:
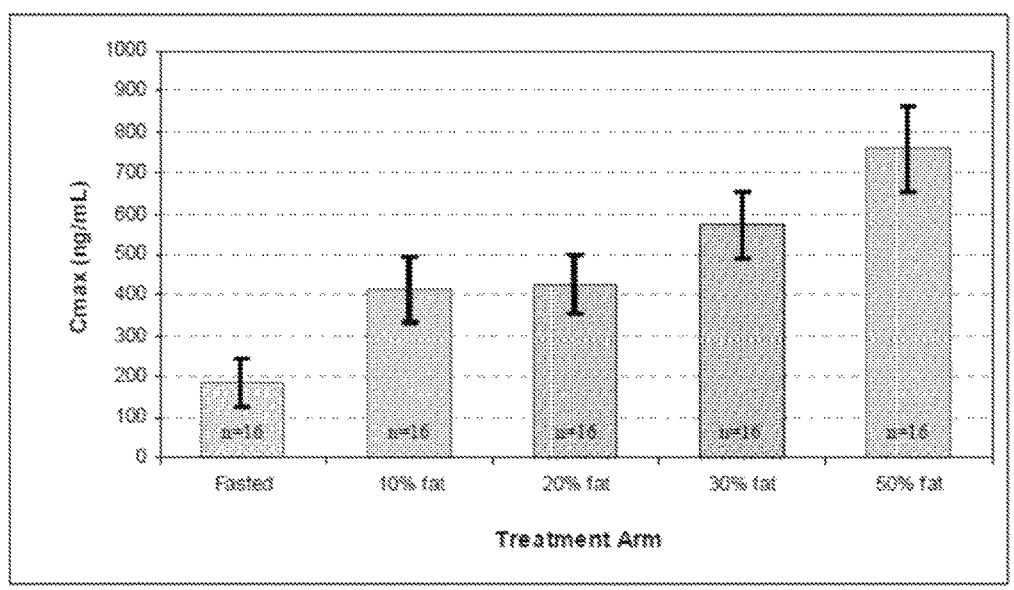
FIG. 4 provides $C_{max}$ values of serum T levels in subjects having consumed meals of varying fat content (as a percentage by weight) prior to oral administration of a TU formulation described herein.
Figure 5:
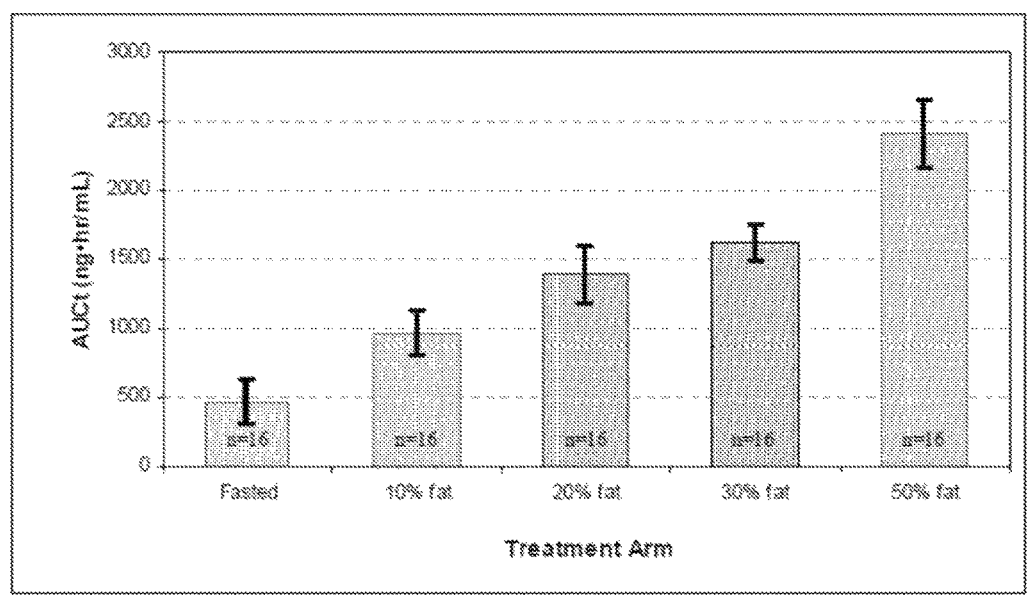
FIG. 5 provides area under the curve (AUC) values of serum T levels in subjects having consumed meals of varying fat content (as a percentage by weight) prior to oral administration of a TU formulation described herein.
Figure 6:
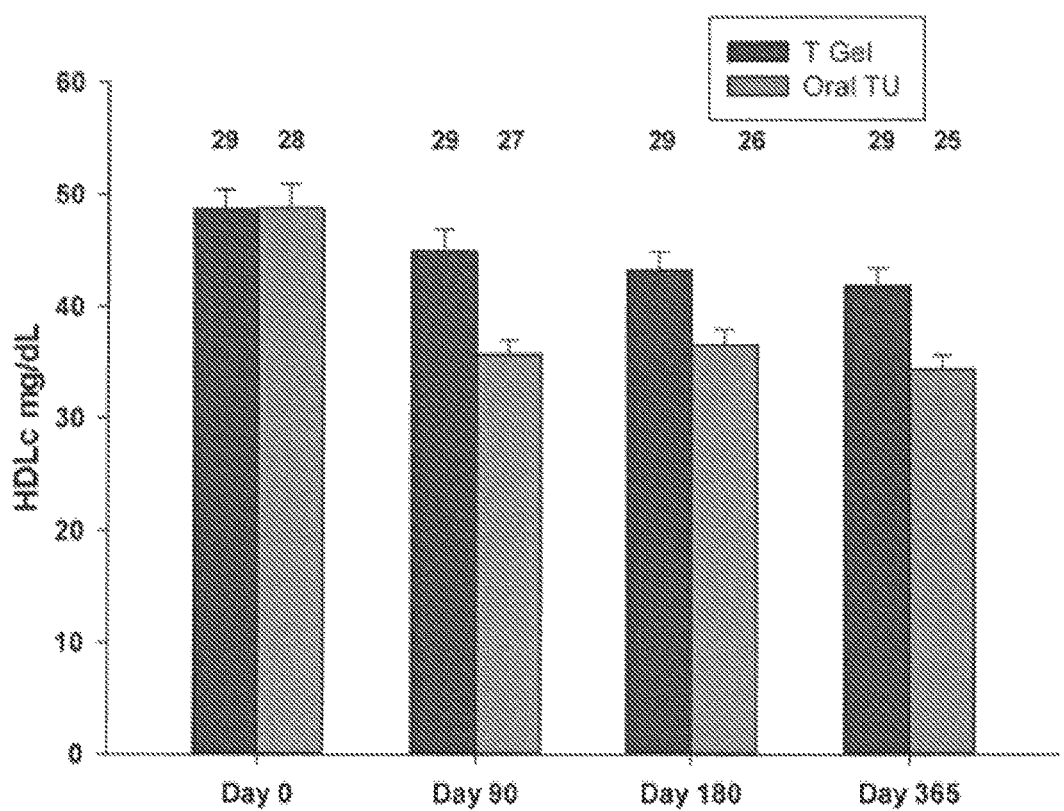
FIG. 6 provides mean±SEM HDLG response to oral TU group vs. AndroGel® at Baseline (Day 0) and Days 90, 180 and 365 after treatment in the study described in Example 7.
Figure 7:
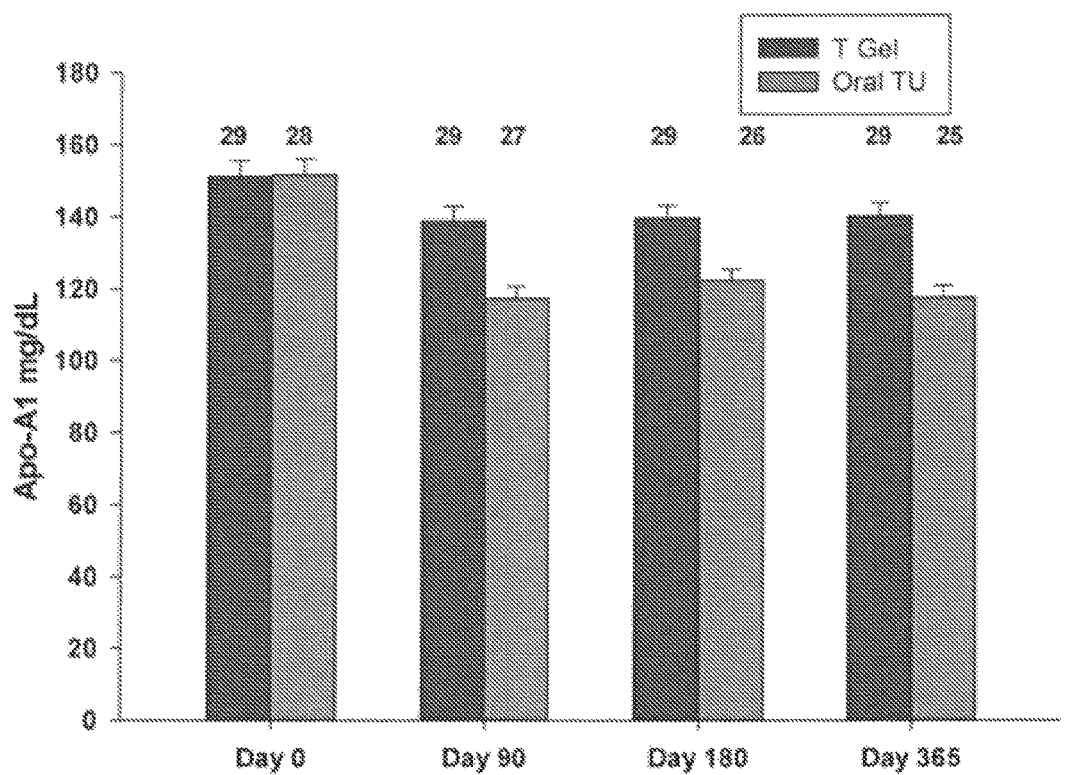
FIG. 7 provides mean±SEM apoA1 response to oral TU group vs. AndroGel® at Baseline and Days 90, 180 and 365 after treatment in the study described in Example 7.
Figure 8:
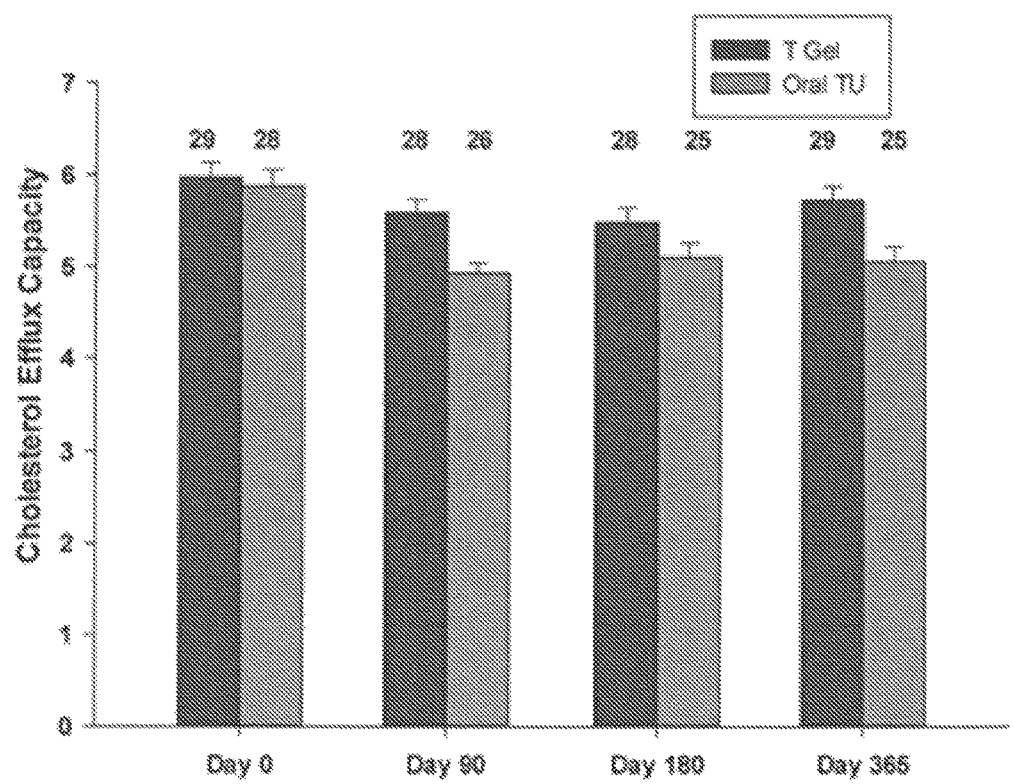
FIG. 8 provides mean±SEM CE capacity expressed as % in oral TU group vs. AndroGel® at Baseline and Days 90, 180 and 365 after treatment in the study described in Example 7.
Figure 9:
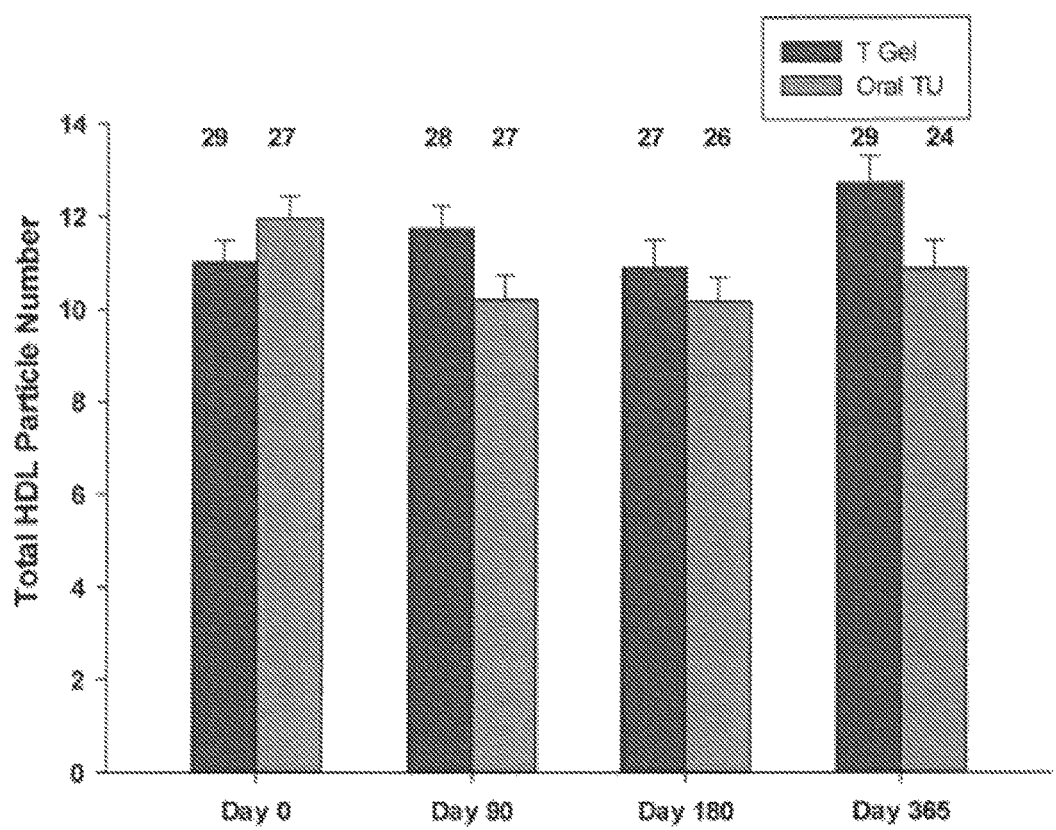
FIG. 9 provides mean±SEM of total HDL particle number expressed as nmol/L in oral TU group vs. AndroGel® at baseline and Days 90, 180 and 365 after treatment in the study described in Example 7.
Figure 10:
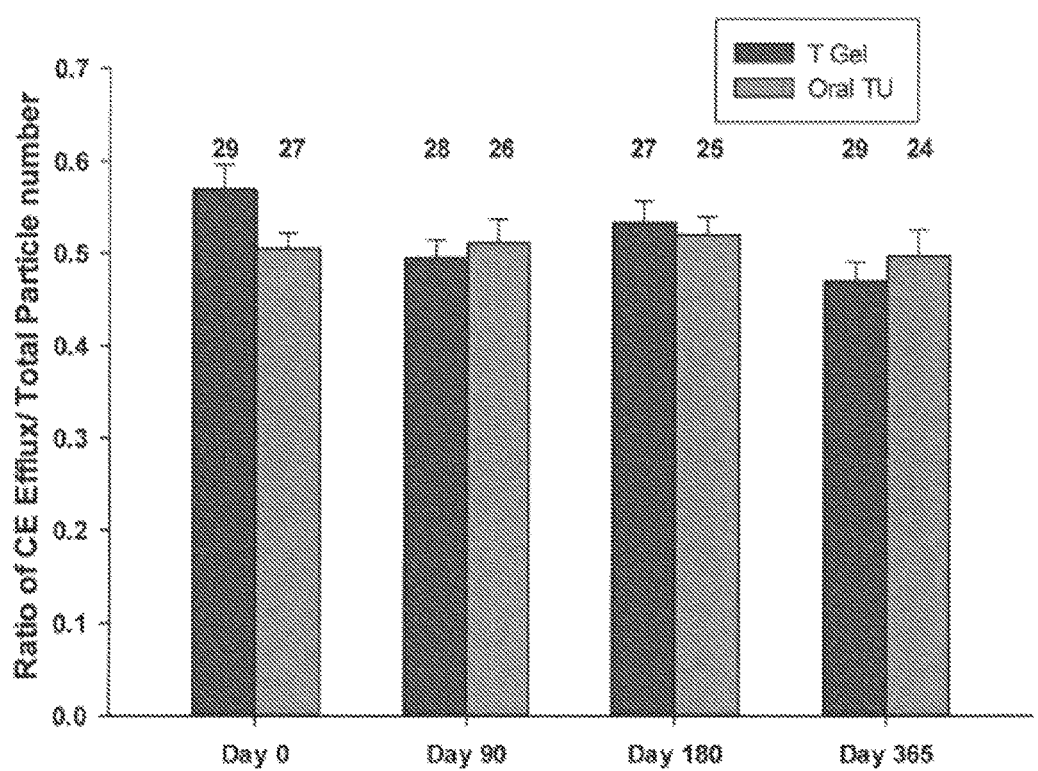
FIG. 10 provides mean±SEM of ratio CE/HDLtp in oral TU group vs. AndroGel® at baseline and Days 90, 180 and 365 after treatment in the study described in Example 7.
Figure 11:
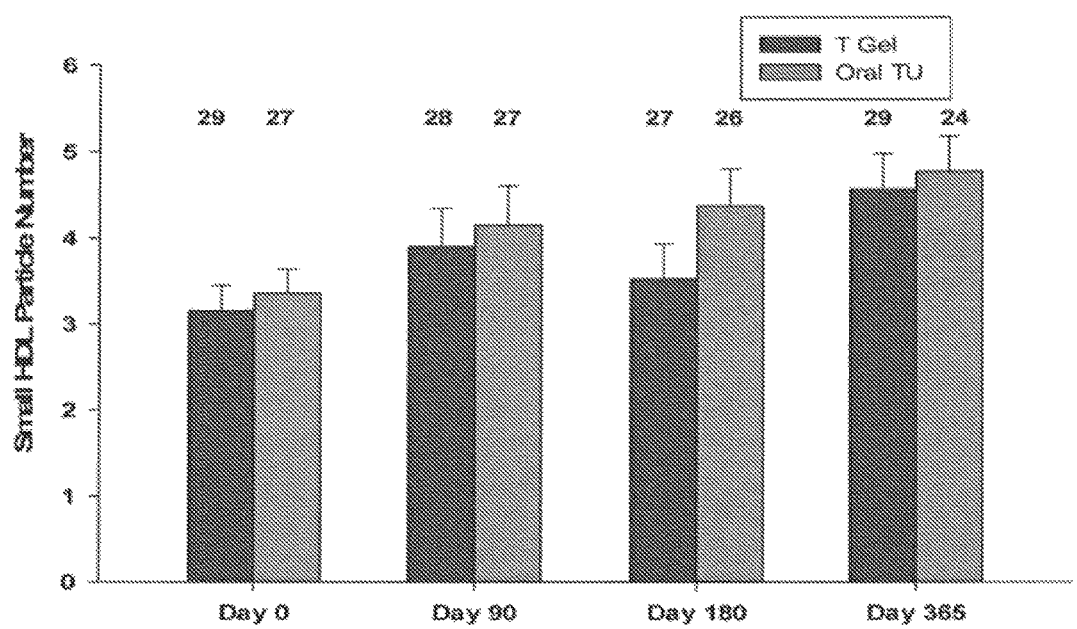
FIG. 11 provides mean±SEM response of small HDL particle number over time in men treated with oral TU or AndroGel® for 365 days. Particle concentrations in nmol/L in oral TU group vs. AndroGel® at Baseline and Days 90, 180 and 365 after treatment in the study described in Example 7.
Figure 12:
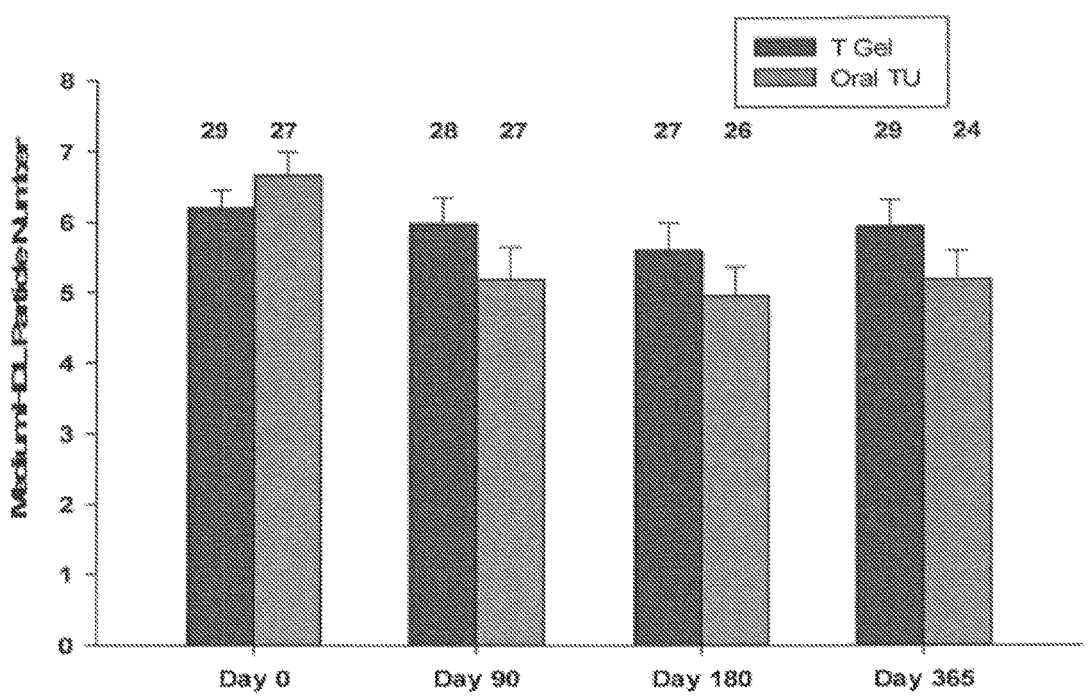
FIG. 12 provides mean±SEM response of medium HDL particle number over time in men treated with oral TU or AndroGel® for ~365 days. Particle concentrations in nmol/L in oral TU group vs. AndroGel® at Baseline and Days 90, 180 and 365 after treatment in the study described in Example 7.
Figure 13:
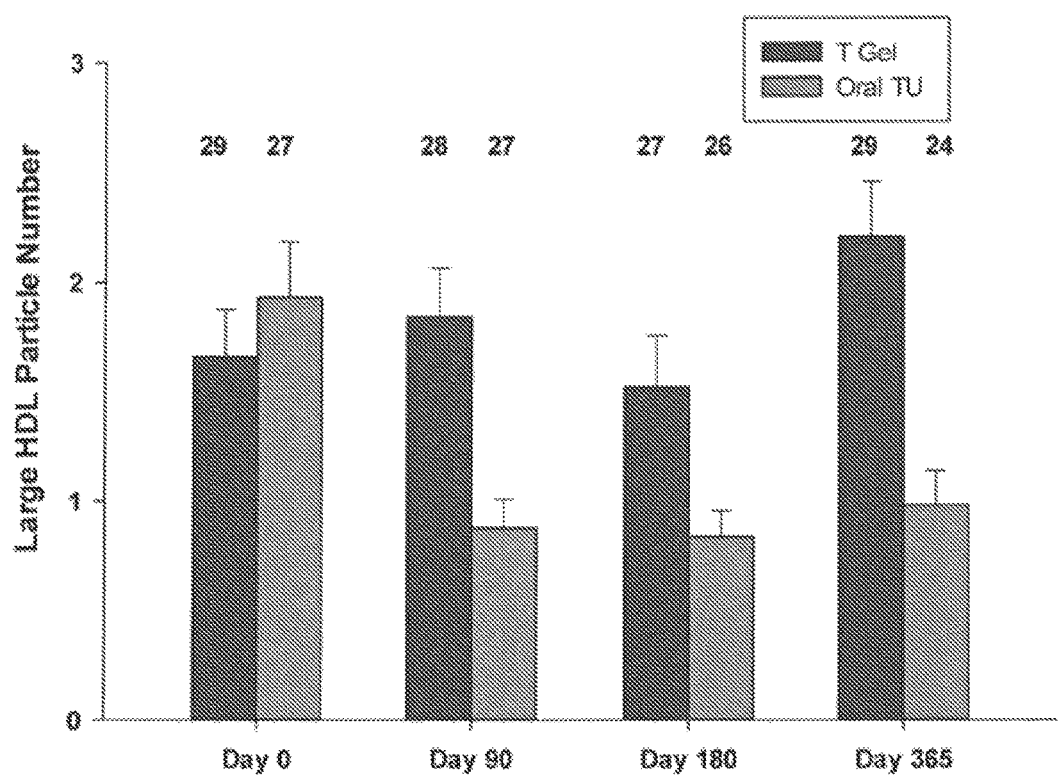
FIG. 13 provides mean±SEM of large HDL particle concentrations in nmol/L in oral TU group vs. AndroGel® at Baseline and Days 90, 180 and 365 after treatment in the study described in Example 7.
Figure 14:
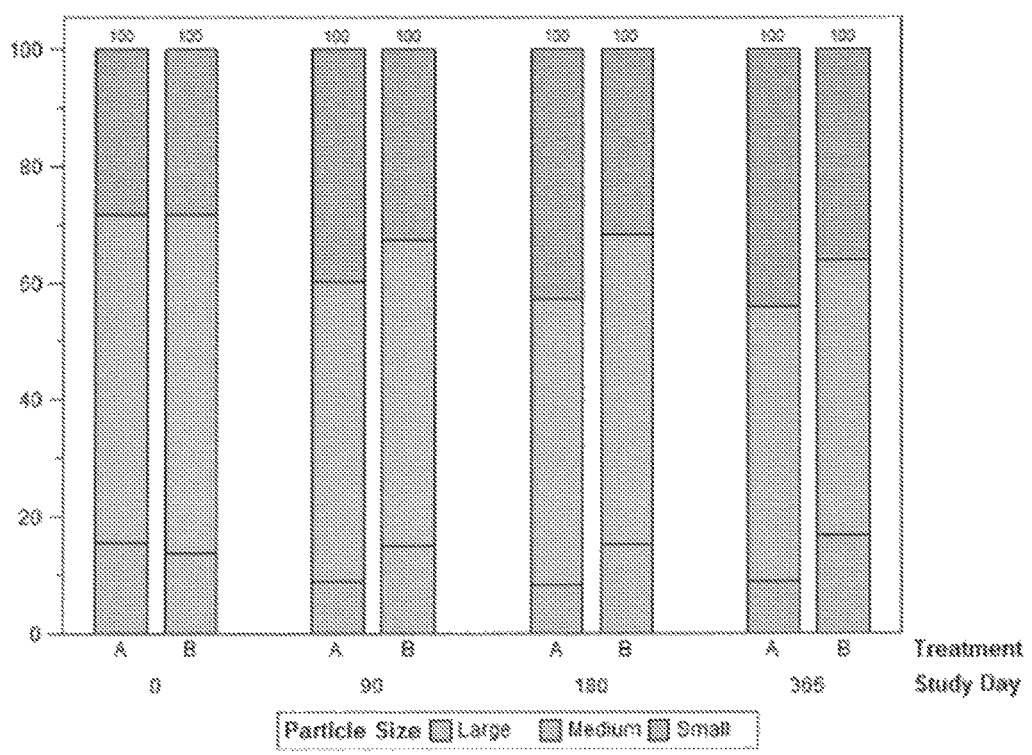
FIG. 14 provides percentile of small HDL particles, medium HDL particles, and large particles in oral TU group (Treatment A) vs. AndroGel® group (Treatment B) at Baseline and Days 90, 180 and 365 in the study described in Example 7.
Figure 15:
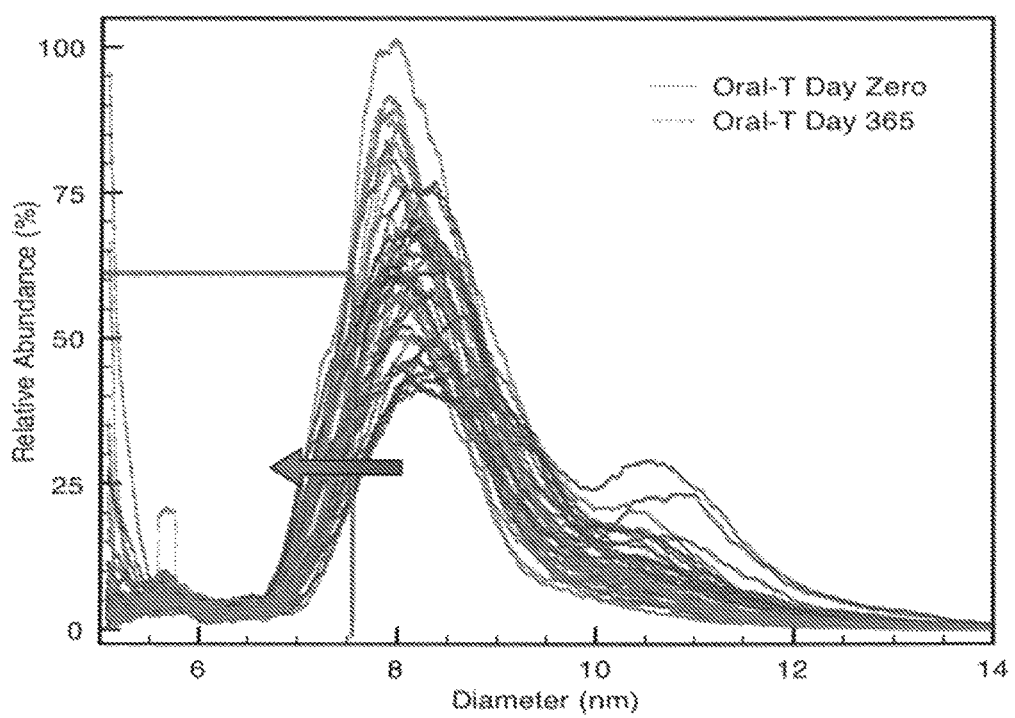
FIG. 15 provides spectra of HDL particle composition from oral TU subjects at Day 0 and Day 365 in the study described in Example 7. Note that in the square (lower left quadrant) showing spectra of HDL particle <7.5 nm, a shift occurs to the left (see arrow) in the very small HDL particle <7.5 nm on Day 365 as opposed to Day 0 particles.
Figure 16:
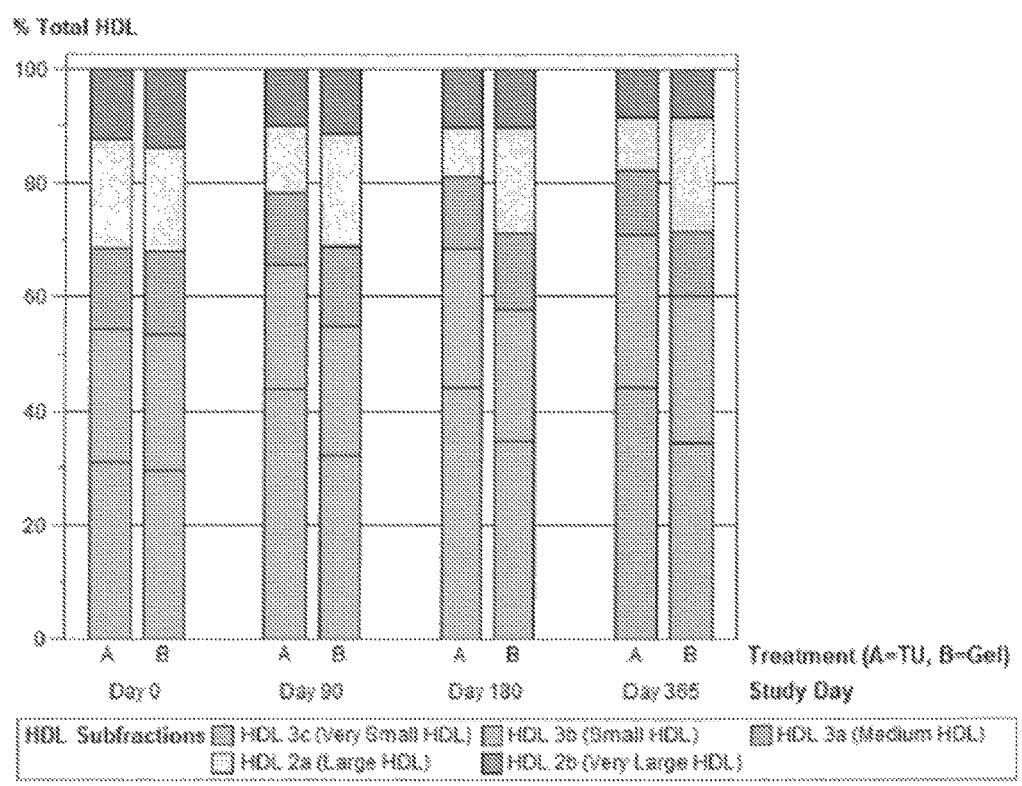
FIG. 16 provides the percentile of very small HDL particles, small HDL particles, medium particles, large particles, and very large particles, in oral TU group (Treatment A) vs. AndroGel® group (Treatment B) at baseline and Days 90, 180 and 365 in the study described in Example 7.

PK parameters (Table 8, FIGS. 3-5) observed for serum T in response to a single, high-dose of oral TU were found to be similar for a low-fat and normal fat diet—in fact so much so that they were bioequivalent (i.e., the 90% confidence interval was between 85-125%). Similar serum T PK parameters were also observed when the normal- and high-fat meals were compared. And although the high-fat meal yielded a greater serum T response (albeit not statistically different), the mean ratio of least square means fell within 70-143% when compared to the normal-fat meal—a clinically insignificant difference of <30%.

7-day treatment (Example 2) and from the 30-day treatment (Example 3), where repeat dose studies of oral TU where the PK under the differing meal conditions still showed similar results for $C_{max}$ and $C_{avg}$ distributions [both studies administered 200 mg T (as TU), BID].

Statistical comparisons of the serum T response observed after oral TU was taken without food or with a very low fat, low fat, or high fat diet versus a normal fat diet (i.e., reference diet) revealed that there was no statistically significant difference at the p<0.05 level between the low-fat or high-fat diets versus the normal diet. Conversely, administration of oral TU as a SEDDS formulation while fasting or with a very low-fat breakfast yielded serum T PK parameters significantly different (i.e., lower) from a normal diet. Accordingly, the fat content of meals taken with the testosterone ester formulations provided herein can differ substantially from "normal", without a clinically significant impact on the levels of T obtained. Thus, a patient is permitted flexibility in eating habits from meal to meal, and from day to day, which is not possible with other oral TU formulations. Other oral TU formulations are unable to achieve any meaningful serum T levels in the fasted state.

Example 5—In Vitro Dissolution Tests

Dissolution studies of TU formulations described herein were studied in vitro to assess their correlation with the PK profiles observed in vivo. In a first study, the dissolution of Formulation B was studied. Andriol® Testocaps® (40 mg TU per softgel dissolved in a mixture of castor oil and propylene glycol laurate) was included for comparison. The study was conducted with essentially equivalent doses of TU, i.e., 1 capsule of Formulation B (158.3 mg TU) and 4 softgels of Testocaps® (4×40 mg=160 mg TU). The dissolution (i.e., the release of TU from the respective formulations) was studied in Fed State Simulated Intestinal Fluid (FeSSIF) medium, which simulates intestinal fluid upon stimulation by a meal. FeSSIF contains sodium hydroxide, glacial acetic acid, potassium chloride, lecithin, and sodium taurocholate. The final emulsion is adjusted to pH 5.0.

Data presented in Tables 9 and 10 demonstrate that the TU formulation released approximately 40% of its TU within the first 30 minutes and about 60% of the total capsule after 4 hours. For the Testocaps®, however, there was little to no drug released (1%) for the entire 4 hours. The observed

TABLE 8

| | Serum T pharmacokinetic parameters (mean ± SD) in response to oral TU administered with different diets | | | | |
|---|---|---|---|---|---|
| | Fasting | 6-10% Fat | 20% Fat | 30% Fat | 50% Fat |
| $C_{Avg}$[1] (ng/dL) | 526 ± 324 | 781 ± 385 | 884 ± 505 | 1010 ± 356 | 1260 ± 477 |
| $C_{Max}$ (ng/dL) | 948 ± 798 | 1370 ± 732 | 1520 ± 711 | 1760 ± 598 | 2140 ± 901 |
| $T_{Max}$ (hr) | 4.1 ± 0.96 | 4.9 ± 1.8 | 6.3 ± 3.9 | 5.1 ± 1.5 | 6.4 ± 4.9 |
| AUC (ng * h/dL) | 7796 ± 3673 | 10855 ± 4285 | 12477 ± 5028 | 13639 ± 3773 | 16464 ± 5584 |

$C_{avg}$ is calculated as $AUC_{0-\infty}/\tau$ ($\tau$ = dosing interval = 12 hours for BID dosing)

Variability in PK response appeared to be highest following the first dose, or first few doses of oral TU, and decreased as therapy continued. Consequently, any impact of dietary fat across the range of low-normal-high on serum T PK parameters is likely to be insignificant during chronic dosing. This stance is consistent with the PK findings from the major difference in the dissolution of TU from these two formulations can be attributed, at least in part, to the presence of the hydrophilic surfactant, e.g., Cremophor® RH40 in Formulation B. In contrast, Andriol® Testocaps® incorporate an oil (castor oil) and a lipophilic surfactant (propylene glycol laureate) only.

TABLE 9

% Release of TU from Formulation B

| Time (Hours) | 1 | 2 | 3 | Average |
|---|---|---|---|---|
| 0.5 | 39.3 | 39.2 | 34.6 | 37.7 |
| 1 | 46.2 | 43.6 | 44.3 | 44.7 |
| 2 | 52.8 | 50.9 | 49.8 | 51.2 |
| 4 | 62.7 | 61.7 | 61.3 | 61.9 |
| Infinity | 96.0 | 100.1 | 90.9 | 95.6 |

TABLE 10

% Release of TU from Andriol Testocaps ®

| Time (Hours) | 1 | 2 | 3 | Average |
|---|---|---|---|---|
| 0.5 | 0.0 | 0.0 | 0.0 | 0.0 |
| 1 | 0.0 | 0.0 | 0.0 | 0.0 |
| 2 | 0.0 | 0.9 | 0.0 | 0.3 |
| 4 | 1.3 | 1.1 | 1.3 | 1.3 |
| Infinity | 3.9 | 3.6 | 1.5 | 3.0 |

In a second study, Formulation A was subjected to a similar assay, but using a 5% Triton X100 potassium phosphate buffer (pH 6.8) as a dissolution medium. The results are provided in Table 11 below. In this study, 98% of the TU from the TU formulation was released within the first 15 minutes of dissolution and once again the presence of the hydrophilic surfactant Cremophor® RH40 certainly facilitated this fast dissolution and TU release.

TABLE 11

% Release of TU from Formulation A

| Time (M) | 1 | 2 | 3 | 4 | 5 | 6 | Average |
|---|---|---|---|---|---|---|---|
| 0 | 0.0 | 0.0 | 0.0 | 0.0 | 0.0 | 0.0 | 0.0 |
| .25 | 98.9 | 96.9 | 97.7 | 95.7 | 96.6 | 101.0 | 97.8 |
| 0.5 | 98.9 | 97.8 | 98.4 | 98.3 | 97.5 | 100.0 | 98.5 |
| 1.0 | 99.5 | 98.2 | 98.0 | 98.4 | 98.1 | 100.2 | 98.7 |

Example 6—Pharmacokinetic Efficacy of Oral TU (Rextoro®) in Two Phase III Trials (CLAR09007 and CLAR12011)

Figure 17:
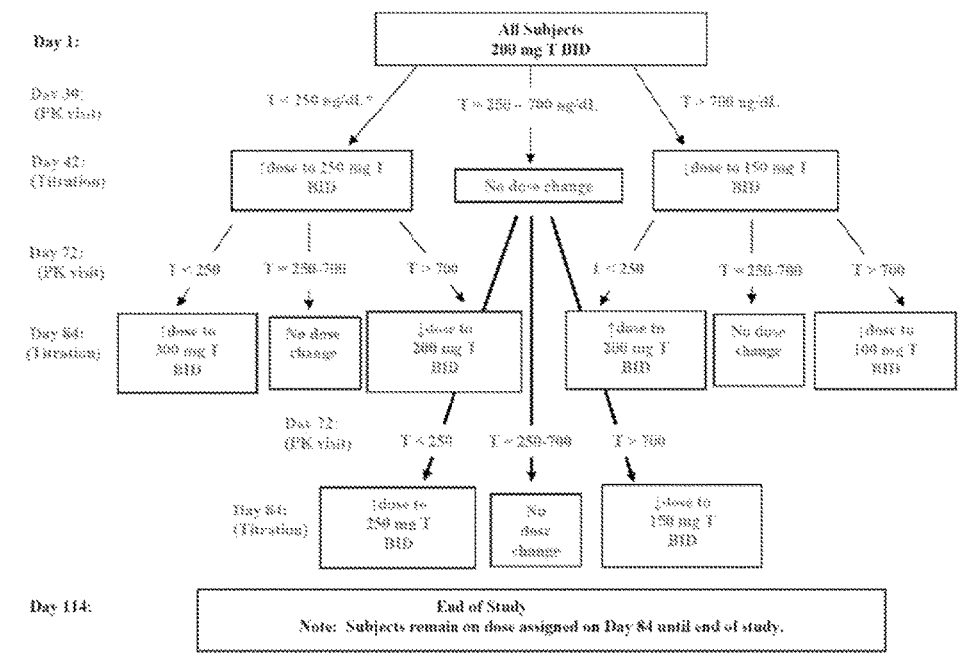
FIG. 17 provides the dose titration scheme used in the study described in Example 7.
Figure 18:
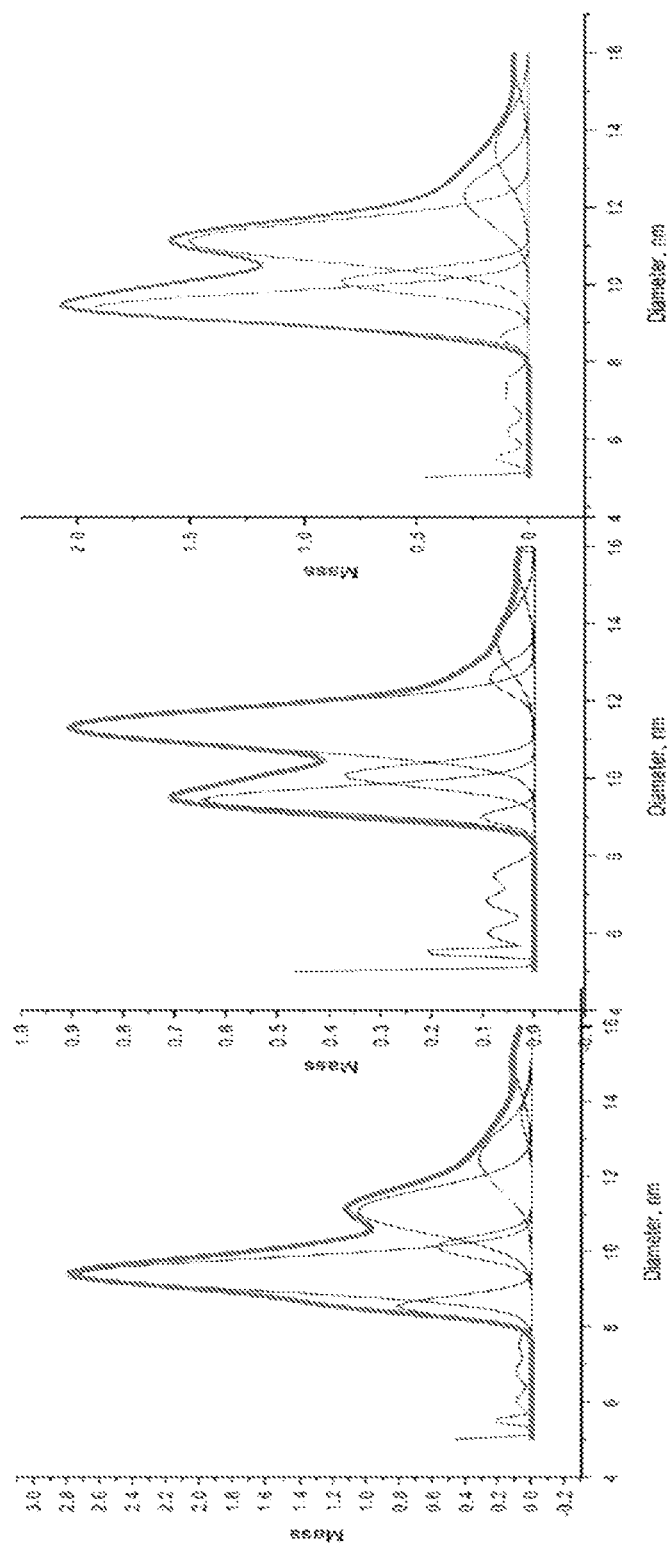
FIG. 18 provides representative results for ion mobility analysis of HDL particle subclasses performed on 3 representative plasma samples. The y-axis shows mass concentration (arbitrary units) derived from transformation of particle concentration, which is measured directly by this procedure. Shown from left to right are deconvoluted curves that delineate the 5 major HDL subclasses (HDL-VS, HDL-S, HDL-M, HDL-L, and HDL-VL) as described in Table 1. This method also indicates small peaks larger than HDL-VL, which have not yet been characterized. Particle concentration for each subclass is determined from the area under the curve. HDL, high-density lipoprotein; HDL-L, large high-density lipoprotein; HDL-M, medium high-density lipoprotein; HDL-S, small high-density lipoprotein; HDL-VL, very large high-density lipoprotein; HDL-VS, very small high-density lipoprotein (Toth et al., *Journal of Clinical Lipidology* (2013) 7, 484-525).
Figure 19:
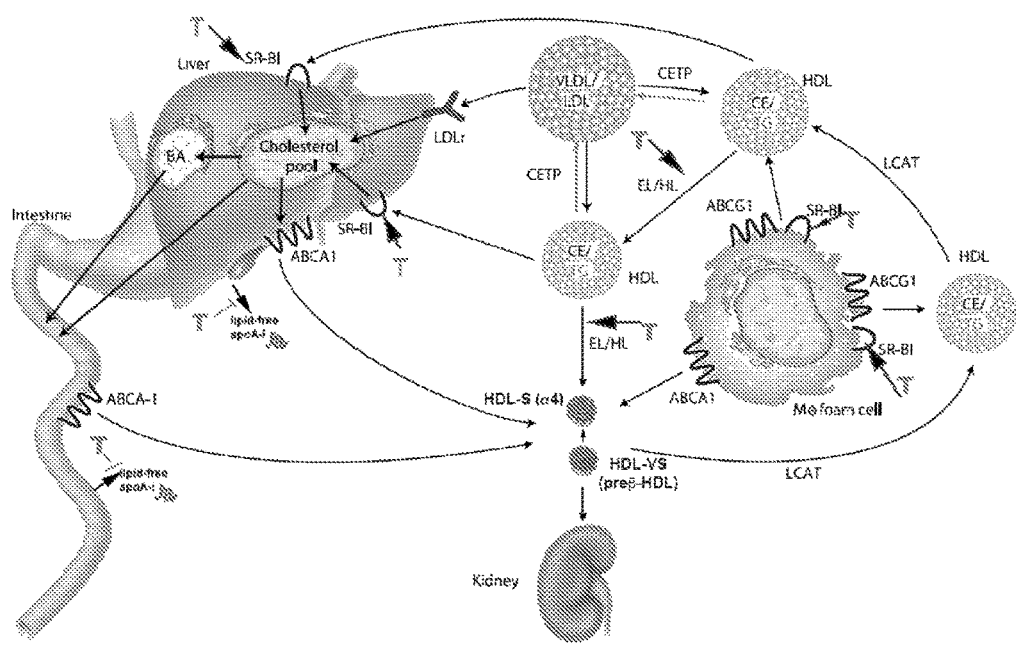
FIG. 19 provides the effects of testosterone on HDL metabolism.
Figure 20:
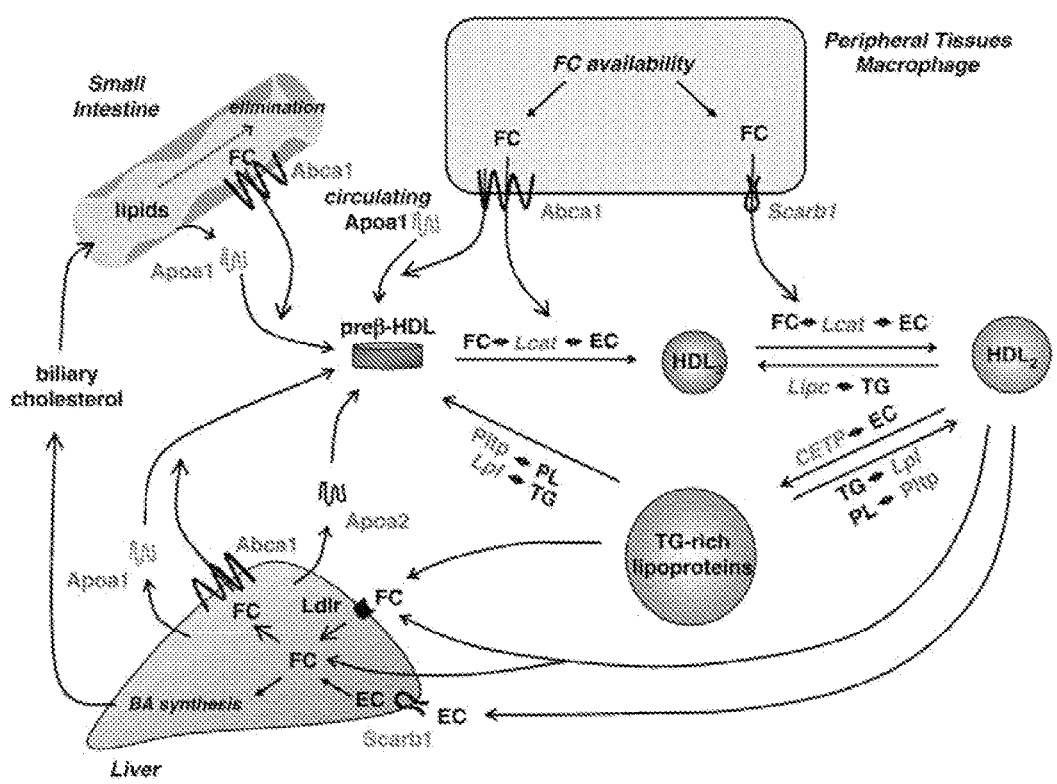
FIG. 20 provides the effect of PPARα on HDL metabolism. PPARα impacts HDL-cholesterol metabolism by modulating synthesis, HDL remodelling, and reverse cholesterol transport. The PPARα targets listed here distinguished by up-regulation (Apoa1, Apoa2, Abca1, Scarb1 in the peripheral tissues, Lcat, Lipc, Pltp, and Lpl) or down-regulation (CEPT and Scarb1 in the liver) of the mRNA gene expression (regular text) or protein expression/activity (italics). PL=phospholipid.
Figure 21:
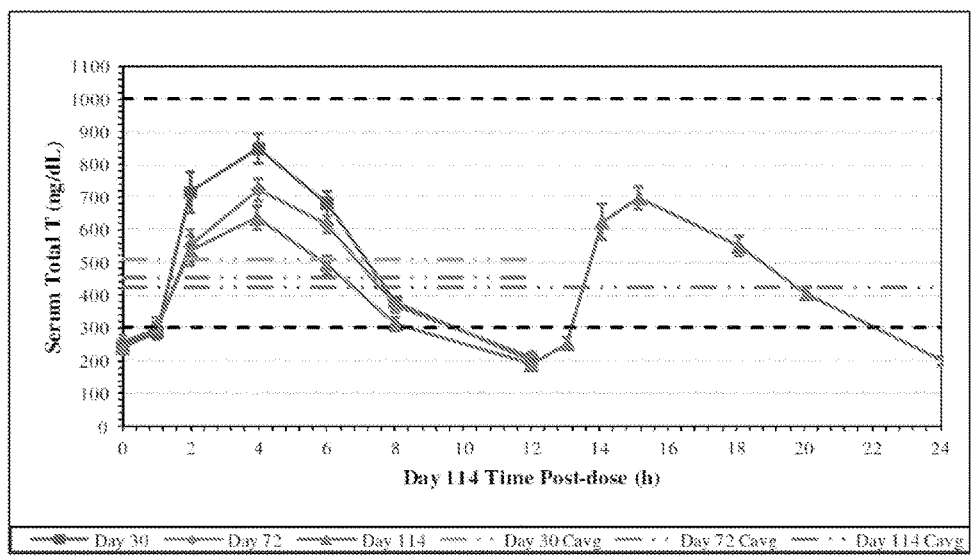
FIG. 21 provides serum total T on PK evaluable days in response to two dose titrations after an original dose of 200 mg T (as TU) bid on day 30 (CLAR12011). The black dashed lines represent the serum T range in eugonadal men.
Figure 22:
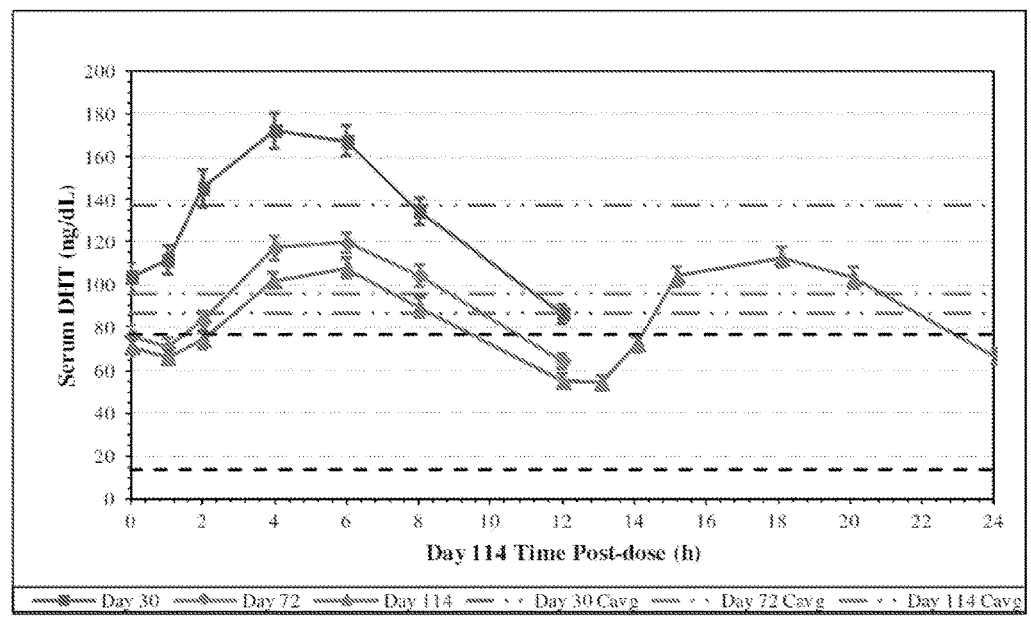
FIG. 22 provides serum DHT on PK evaluable days in response to two dose titrations after an original dose of 200 mg T (as TU) BID on day 30 (CLAR12011). The black dotted lines represent the DHT range in eugonadal men.

Two Phase 3 trials have evaluated the safety of Rextoro® in hypogonadal men and have been used to refine and validate a dose titration algorithm. The initial phase 3 trial, CLAR09007, compared Rextoro® to AndroGel® 1%. The dose titration algorithm used for Rextoro® in this study resulted in acceptable T replacement with 87% of men achieving a eugonadal T $C_{avg}$ but the frequency of high $C_{max}$ levels was greater than desired. Based on PK results from CLAR09007, the dose titration algorithm was modified (see FIG. 17) and a second phase 3 trial, namely, CLAR12011, was performed. CLAR12011 was a single-arm study which demonstrated that the revised algorithm yielded acceptable T replacement with 75% of men achieving eugonadal T $C_{avg}$. Moreover, the $C_{max}$ profile was generally aligned with FDA targets with a low frequency of high $C_{max}$ levels. In both phase 3 trials, serial PK measurements were obtained for T and DHT. Predictably, based on previous reports in the literature, oral dosing with TU increased serum DHT and the DHT/T ratio. Table 13 presents T and DHT concentrations and the T/DHT ratio for CLAR09007 on the primary analysis day (Day 90) and the end of the study (Day 365) and for CLAR12011 for the primary analysis day which was the end of the study (Day 114). FIGS. 21 and 22 provide the serum profiles for serum T, DHT and the DHT/T ratios observed in CLAR12011 in response to an initial oral dose of 200 mg T (as TU) BID with dose titrations at Days 30 and 72 based on the 3-5 hours post dose value, if needed. The DHT and DHT/T ratio reference range for the Phase 3 trials, is 13.69-76.88 ng/dL and 0.036-0.114, respectively. T and DHT were measured by LC/MS/MS.

Clinical trials of Rextoro® indicate that this treatment approach, with appropriate dose titration, can be used to effectively restore serum T to the normal range in hypogonadal men and do so without excessive frequency of supraphysiological peak serum T concentrations. Importantly, oral TU therapy resulted in only modest elevations in serum dihydrotestosterone (DHT) and in the DHT/T ratio—well within the range observed in the literature for other forms of TRT. Dihydrotestosterone and DHT/T ratios were been measured in a number of TRT clinical trials. The effects of various TRTs, some of which are FDA approved and others which are used in countries outside the U.S., on prostate are summarized in Table 12. This table indicates that even dramatic elevations in the DHT and DHT/T ratios for prolonged periods (e.g., up to 24 months) fail to cause clinically meaningful effects on prostate. Of particular note is the fact that DHT concentrations and DHT/T ratios observed in response to Rextoro® are similar or less than other TRTs approved for use in the clinical management of male hypogonadism—none of which have been associated with DHT-specific safety signals despite their long-standing use. Published studies of DHT-gel use in hypogonadal men provide a sound basis on which to conclude that this form of androgen therapy is without a demonstrable negative impact on prostate. Studies of 3, 6 and 24 months duration have not yielded evidence that DHT causes prostate hyperplasia (i.e., BPH) nor has DHT therapy been associated with an increased rate of prostate cancer, and this is in men who have sustained DHT levels in the 600 ng/dL range.

TABLE 12

Results from Studies CLAR-09007 and CLAR-12011 of serum DHT and DHT/T Ratios presented as mean ± SD.

| | CLAR-09007 | | | | | | CLAR-12011 | |
|---|---|---|---|---|---|---|---|---|
| | T-Gel | | | Oral TU | | | Oral TU | |
| | Baseline | Day 90 | Day 365 | Baseline | Day 90 | Day 365 | Baseline | Day 114 |
| N | 163 | 162 | 132 | 148 | 145 | 127 | 144 | 116 |
| DHT mean (ng/dL) | 17 | 80 | 69 | 17 | 125 | 118 | 18 | 87 |

TABLE 12-continued

Results from Studies CLAR-09007 and CLAR-12011 of serum DHT and DHT/T Ratios presented as mean ± SD.

| | CLAR-09007 | | | | | | CLAR-12011 | |
|---|---|---|---|---|---|---|---|---|
| | T-Gel | | | Oral TU | | | Oral TU | |
| | Baseline | Day 90 | Day 365 | Baseline | Day 90 | Day 365 | Baseline | Day 114 |
| DHT SD (ng/dL) | 12 | 46 | 33 | 11 | 74 | 64 | 9 | 36 |
| DHT Range (ng/dL) | 1-106 | 16-330 | 11-172 | 1-76 | 23-539 | 31-496 | 2-42 | 29-242 |
| DHT/T Mean | 0.096 | 0.168 | 0.171 | 0.114 | 0.209 | 0.240 | 0.077 | 0.220 |
| DHT/T SD | 0.094 | 0.067 | 0.069 | 0.176 | 0.090 | 0.114 | 0.043 | 0.086 |
| DHT/T Range | 0.012-0.693 | 0.044-0.540 | 0.024-0.409 | 0.010-1.720 | 0.077-0.562 | 0.058-0.847 | 0.007-0.412 | 0.052-0.537 |

Example 7—Study to Determine the Effects of Testosterone Replacement on HDL-Mediated Cholesterol Efflux A sub-study was performed of a randomized, open-label, active controlled, 2-arm, 12-month study (CLAR09007) in hypo gonadal men conducted at three sites. Subjects were randomized to either oral TU (Group A) or AndroGel®, a transdermal T gel (Group B). In the oral TU group, where higher $C_{avg}$ values of T were observed, there was a rapid (occurring as early as day 30) and sustained suppression of HDL in the 20% range. There was a redistribution in HDL subclasses in the oral TU group with a significant shift toward very small, more anti-atherogenic, HDL subclass particles. In the AndroGel® group, HDL suppression was in the expected 10% range. There was a modest but statistically significant drop in mean CE capacity in the oral TU group compared to AndroGel®, but both treatments were associated with a decrease in CE capacity. In the experiments performed as described, CE capacity and HDL total particle number were reduced by a lesser magnitude than HDL or Apo-A1 in both treatment arms, and this suppression got better with time. CE per HDL particle was greater in the oral TU group then in the AndroGel® group (FIGS. 6-16). However, this assay represents baseline CE and not ApoA1-mediated efflux which is a more appropriate measure of pre-beta HDL and small particle-mediated efflux through the ABCA1 receptor. In future experiments, CE capacity will be measured using the cyclic AMP mediated ApoA1-receptor or cell lines that over-express ABCA1. Further future experiments will measure cyclic AMP stimulated expression of ABCA1, or cell lines over expressing the ABCA1 receptor will be utilized to measure small particle CE capacity. Alternatively, in vivo methods of measuring CE can be used, such as those described in Hu Y. W. et al., *PLoS-ONE* 2014. 9(4): e94997, or mice harboring knock-ins or knock-outs of the various CE receptors SRV1, ABCA1, ABCG1.

Particle concentrations of HDL subfractions were analyzed by two methods in specific particle-size intervals using ion mobility (IM), which permits direct particle quantification as a function of particle diameter following removal of plasma proteins (Caulfield, M. P., et al., *Clin Chem*, 2008. 54(8): p. 1307-16. The IM instrument utilized an electrospray to create an aerosol of particles, which then passed through a differential mobility analyzer coupled to a particle counter. Particle concentrations (nmol/L) were determined using lipoproteins isolated by ultracentrifugation. Inter-assay variation was minimized by inclusion of two controls in each analysis. Inter- and intra-coefficients of variance were <20%. The main difference between the two methods in HDL fractionation was in the deconvolution of the HDL subfractions. Method I deconvoluted HDL into three subcategories, small HDL particles (7.5-8 nm diameter), medium (8-9 nm diameter) and large (9-12.9 nm diameter). This small category contains the small discoidal (≈7.4 nm diameter) with α4 mobility on 2-D gel electrophoresis, and some of the larger heterogeneous preβ-1 and discoid α4 subspecies (up to 7.4 nm and a fraction of $HDL_3$ fraction grouped together). (See FIG. 14). The traditional ion mobility method, Method II, in its original incarnation grouped HDL subfractions into two bins, namely, $HDL_{2b}$ (14.5-10.5 nm diameter) and $HDL_{2a}+HDL_3$ (10.5-7.65 nm diameter). A more recent deconvolution program along with method improvements allowed for deconvoluting HDL into five subfractions (Toth, P. P., et al., *J Clin Lipidol*, 2013. 7(5): p. 484-525) agreed upon by the expert panel representing all major researchers in the lipid fraction field (Rosenson et al., *Clin Chem*, 2011. 57(3): p. 392-410) and adopted by the National Lipid Association (Toth, P. P., et al., *J Clin Lipidol*, 2013. 7(5): p. 484-525). This refined method allowed for a higher degree of resolution of the very small $HDL_{3c}$ (7.2-7.8 nm diameter) a subfraction that contains both the larger preβ-1 particles and discoidal lipid poor HDL particles (i.e., high affinity ligands for ABCA1). Another important change was the fractionation of traditional $HDL_3$ fraction into two more subfractions: small $HDL_{3b}$ (8.2-7.8 nm diameter) and medium HDL ($HDL_{3c}$: 8.2-8.8 nm diameter) with large HDL ($HDL_{2a}$: 8.8-9.7 nm diameter) and very large HDL ($HDL_{2b}$: 9.7-12.9 nm diameter) accounting for the remainder of the fractions. (See FIG. 16). HDL modifications were observed in the 09007 study. Although this sub-study was using subjects from the CLAR09007 study, similar results would be expected from a substudy of subjects from the CLAR12011 study.

Example 8—Phase III, Open-Label Study of the Safety and Efficacy of Oral TU in Hypogonadal Men (CLAR12011)

A 4-month open-label, repeat-dose, dose-titration study was performed with 148 hypogonadal men at multiple study sites. The screening period was followed by a treatment period of approximately 114 days during which up to 2 dose titrations occurred as necessary. All subjects began treatment at an oral dose of 200 mg T, twice a day (BID). Subjects were instructed to take their study medication within 15 minutes after completion of a meal (i.e., not on an empty stomach). Serial PK samples over 12 h were obtained at Visit 2 (Day 30) and Visit 4 (Day 72). Serial PK samples over 24 h were obtained at Visit 6 (Day 114) (±3 days). Doses could be titrated at Visit 3 (Day 42) (±3 days) and/or Visit 5 (Day 84) (±3 days), if needed, based upon the serum T concentrations obtained at Visit 2 (Day 30) and Visit 4 (Day 72), respectively. The need for dose titration for each subject was determined by the serum T concentration from the sample drawn 3-5 h post AM dose on Visit 2 (Day 30) and Visit 4 (Day 72) as detailed in the scheme depicted in FIG. 17.

The primary objective of this clinical study was to assess the efficacy of an oral TU SEDDS formulation for the replacement of T in hypogonadal men on Day 114 of treatment. Efficacy was assessed as the percentage of treated subjects meeting the specific endpoint of having their 24-hour $C_{avg}$ of serum total T within the eugonadal range of 300 ng/dL to 1000 ng/dL on Day 114. If the observed percentage was 75% or greater, and the lower bound of the 95% CI about that observed rate was greater than 65%, the product would meet the efficacy target typical for T replacement products. The study met its primary endpoint with 75.0% (87/116) of subjects on Day 114 in the eugonadal range. The lower bound of the 95% CI, 66.1%, also met the efficacy target. The mean serum T $C_{avg}$ on Day 114 was 422.3 ng/dL.

Oral TU was generally safe and well tolerated. Adverse events reported in this study were consistent with those reported in the study described in Example 6 by subjects on oral TU and by TRT in general. The most frequently reported treatment-emergent adverse events (TEAEs) were diarrhea and upper respiratory tract infection (3.5% each) and dyspepsia, hypertension, and peripheral edema (2.8% each). Other TEAEs of typically associated with TRT that were reported only once (0.7%) included breast tenderness, polycythemia, and nipple disorder. Related TEAEs occurred at a low frequency, with the most frequently reported related TEAEs having an incidence of 2.1% (3/144). These included dyspepsia, diarrhea, eructation, hematocrit (Hct) increase, prostatomegaly, and hypertension. There were no deaths in the study and only two subjects reported serious TEAEs that were considered definitely not related to study drug. A total of three subjects had a TEAE that led to study drug discontinuation.

Decreases from baseline in total cholesterol and HDL were substantially smaller than that seen in the trial described in Example 6 and this is possibly related to the change in the dosing algorithm which resulted in subjects having a lower mean $C_{avg}$. Higher HDL concentrations have been associated with a reduced risk of myocardial infarction, although pharmaceutical mediated increases in HDL concentration have not uniformly been associated with reductions in cardiovascular (CV) events. Some pharmaceutical agents lower HDL, as an unintended consequence. For instance, beta blockers and hydrochlorothiazide can lower HDL, but these agents reduce the rate of CV events. These agents' pharmacological activities (e.g., beta blockers reduce heart rate/decrease sympathetic tone, hydrochlorothiazide reduces BP) may confound any negative effect of the change in HDL. Although TRT can cause decreases in HDL, they also are associated with positive changes in other CV risk factors such as improvements in insulin resistance and obesity.

At baseline, the mean HDL was 44.3 mg/dL which placed the subjects in the 2nd risk quartile from the Framingham Study for myocardial infarction (Abbott et al., *Arteriosclerosis*. 1988; 8(3): 207-11). At Day 114, the mean HDL was 38.5 mg/dL. This value also corresponds to the 2nd risk quartile. Therefore, the mean change in HDL did not correspond to a change in risk quartile.

Example 9—Liquid-Filled Capsule Fixed-Dose Combinations

A liquid self-emulsifying drug delivery system (SEDDS) formulation of a testosterone ester (e.g., TU) such as Formulation A or B, (or alternatively a SMEDDS or SNEDDS testosterone ester formulation) is mixed with a PPARα agonist, a PPARδ agonist, or a pan-PPAR agonist, either alone or in combination with one or more further excipients, and the resulting mixture is then filled into "00" capsules. A SEDDS formulation of a testosterone ester (e.g., TU) which is semi-solid at room temperature but liquid at 37° C. or higher temperature can also be prepared using high melting point lipophilic surfactants, such as Precirol ATO5 (glyceryl palmitostearate), or high melting point polyethylene glycol (PEG), such as PEG with a molecular weight greater than 600 and preferably greater than 1,000 g/mol, and upon mixing with one or more PPAR agonist and other excipients at high temperature is subsequently filled into "00" capsules.

Example 10—Solid Fixed-Dose Combinations

A liquid self-emulsifying drug delivery system (SEDDS) formulation of a testosterone ester (e.g., TU) such as Formulation A or B, (or alternatively a SMEDDS or SNEDDS TU formulation) is adsorbed onto solid carrier particles, such as silicon dioxide, calcium silicate, magnesium aluminometasilicate, or 2:1 layered phyllosilicate to obtain a free-flowing powder. This powder is mixed with a PPARα agonist, a PPARδ agonist, or a pan-PPAR agonist, and upon mixing with other solid dose excipients, such as fillers, diluents, disintegrants and lubricants, the resulting mixture is then either filled into hard capsules or compressed into tablets.

Example 11—Solid Fixed-Dose Combinations

A liquid SEDDS of a testosterone ester (e.g., TU) is mixed with a liquid SEDDS of a PPARα agonist, a PPARδ agonist, or a pan-PPAR agonist at the desired ratio and the mixture is then adsorbed onto solid carrier particles. Upon mixing with other solid dose excipients, the mixture is then either filled into hard gelatin capsules or compressed into tablets.

Example 12—Adsorption of Liquid TU Compositions onto a Carrier: Liquid Loaded Tablets (LLT)

Liquid compositions of TU (SEDDS) are adsorbed onto solid carriers to improve the flow properties of the lipids and along with other solid dose excipients such as diluents, fillers and disintegrants used to prepare free flowing powders which can then be filled into hard shell capsules or compressed into tablets. Suitable solid adsorbents include: a) porous $SiO_2$, 300 m$^2$/g, 3.2 μm (Sylysia 320) and 500 m$^2$/g, 3.9 μm (Sylysia 550), b) porous calcium silicate, 120 m$^2$/g, 26.1 μm (Florite RE) and c) magnesium aluminometasilicate, 280 m$^2$/g, 75 μm (Neusilin® US2) and 110 m$^2$/g, 100 μm (Neusilin S2). Suitable diluents and fillers include microcrystalline cellulose and lactose. Suitable disintegrants include copovidone and croscarmellose. Wetting agents such as sodium lauryl phosphate (SLS) and lubricants such as magnesium stearate may also be included. The above list of diluents, fillers, and disintegrants, as well as other pharmaceutical excipients, is not meant to be exhaustive but merely illustrative as a person of ordinary skill in the art would recognize that additional types and combination of excipients could be used to achieve the desired in vitro dissolution and in vivo pharmacokinetics.

Example 13—Preparation of TU Liquid Loaded Tablets (LLTs)

50 g of a SEDDS liquid formulation of TU is first prepared as described in U.S. Pat. No. 8,492,369 having the following composition (%, w/w): TU (19.8), oleic acid (51.6), Cremophor® RH40 (16.1), borage oil (10.0), peppermint oil (2.5) and BHT (0.03). For the adsorption onto a solid carrier, 25 g of the SEDDS liquid formulation of TU is transferred into a 500 mL glass beaker equipped with a lab scale mixer using a twisted blade stirrer. Subsequently, 25 g of Neusilin® US2 adsorbent is added gradually to the beaker and the mixture is stirred at a speed of 500-700 rpm. Stirring is continued for additional 5-10 min after the addition of the adsorbent is completed in order to break down any large aggregates (lumps) of the mixture. A free flowing powder is obtained at the end of the mixing process. The free flowing powder can be passed through an 800 μm sieve to remove any not visible lumps that they be present in the formulation. Standard USP tests are used to determine the flow characteristics of the powder and include, the angle of repose, Carr's compressibility index and the Hausner ratio. The resulting free flowing powder is either filled directly into hard gelatin capsules or compressed into tablets. For the preparation of an 840 mg tablet, 748 mg of the free flowing powder is mixed with 84 mg of croscarmellose sodium, a cross-linked carboxy methyl cellulose which acts as a super disintegrant, and 8.4 mg of magnesium stearate (lubricant) and compressed at an optimum pressure of 130-160 MPa. The tensile strength and friability of the LLT1 is measured using standard methodology. The dissolution of the LLT is determined and compared to that of free flowing powder filled into hard gelatin capsules. The composition of the free flowing powder and/or the compressed tablets as well as the various process parameters are adjusted as needed in order to optimize the in vitro dissolution of TU from LLTs. LLTs of TU can readily be prepared using other TU liquid compositions (SEDDS).

Example 14—Liquid and Tablet Formulations of TU Incorporating a Eutectic Mixture of TU with Essential Oil The formation of the eutectic mixture between TU and an essential oil at various ratios (w/w) of TU to the essential oil is monitored through a m.p. depression of TU using differential scanning calorimetry. The essential oil is selected from the group consisting of menthol, peppermint oil, spearmint oil, anise oil, and lemon oil, and mixtures thereof. The essential oil is preferably peppermint oil. The preferred ratio of TU to the essential oil is 1:1 (w/w). For the formation of a liquid or semi-solid SEDDS formulation of TU, the eutectic mixture is solubilized in a lipophilic and hydrophilic surfactant. Preferred lipophilic surfactants include oleic acid, glycerol monolein (Peceol™), glycerol monolinoleate (Maisine™ 35-1), glyceryl palmitostearate (Precirol ATO5), $C_8/C_{10}$ mono-/diglycerides (Capmul® MCM) and mixtures thereof. Cremophor® EL and Cremophor® RH40 are the preferred hydrophilic surfactants. The resulting liquid or semi-solid formulation of TU are filled into hard or soft gelatin capsules or mixed with solid dose excipients to produce free flowing powders which can be filled into capsules or compressed into tablets as described in Example 1. Exemplary compositions are provided in Tables 12-14 below

TABLE 13

Liquid SEDDS formulations of a TU-Peppermint Oil Eutectic Mixture

| Component | % w/w |
|---|---|
| TU | 15 |
| Peppermint Oil | 15 |
| Oleic Acid/Maisine 35-1/Capmul ® MCM | 50 |
| Cremophor EL/Cremophor RH40 | 20 |
| TOTAL | 100 |

TABLE 14

A liquid loaded tablet composition of TU-Peppermint Oil Eutectic Mixture

| Component | % w/w |
|---|---|
| Neusilin ® US2 (1:1) | 89 |
| Croscarmellose Sodium | 10 |
| Magnesium Stearate | 1 |
| TOTAL | 100 |

TABLE 15

A liquid loaded tablet composition of TU without Neusilin ® US2

| Component | % w/w |
|---|---|
| TU | 10 |
| Peppermint oil | 10 |
| Capmul MCM/Oleic Acid/Maisine 35-1 | 20 |
| Cremophor EL/Cremophor RH40 | 10 |
| Copovidone | 10 |
| Maltodextrin | 30 |
| Microcrystalline Cellulose (Avicel PH112) | 10 |

Example 14—Clinical Study of Oral Testosterone Ester and Hypolipidemic Agent Combination The effects of the oral testosterone ester/hypolipidemic agent combinations described herein on hypogonadal men are studied using: protocols similar to those described in Examples 1-4 or 7; and the formulations described in Examples 8 or 9; or a testosterone formulation such as Formulation A or B, and a separate dosage form comprising a hypolipidemic agent.

In yet another embodiment of the present invention, the pharmaceutical products disclosed herein may also be suitable for ameliorating some of the side-effects of certain strategies for male contraception. For example, progestin-based male contraception substantially suppresses luteinizing hormone (LH) and follicle-stimulating hormone (FSH), and thereby suppresses spermatogenesis, resulting in clinical azoospermia (defined as less than about 1 million sperm/mL semen for 2 consecutive months). However, administration of progestins also has the undesirable side-effect of significantly reducing steady-state serum testosterone levels.

In such situations, for example, it may be preferable to provide preparations of progestin concomitantly with testosterone or a testosterone derivative (e.g., TU). More preferably, a pharmaceutical product as described herein is provided, comprising progestin—in an amount sufficient to substantially suppress LH and FSH production—in combination with testosterone, and a hypolipidemic agent. In some embodiments, the pharmaceutical product is for once-daily, oral delivery.

Formulations of the present invention can provide extended release formulations that can deliver testosterone into the serum over several hours. Indeed, the half-life of serum testosterone according to the invention is between 3 and 7 hours, preferably greater than 4, 5, or 6 hours. The serum half-life of testosterone in men, by contrast, is considered to be in the range of 10 to 100 minutes.

Without being bound by or limited to theory, it is believed that the inventive pharmaceutical products achieve these results, in one aspect, by enhancing absorption of a medicament therein by the intestinal lymphatic system rather than by way of portal circulation. In another aspect, again without being bound by or limited to theory, it is believed that by using an ester of testosterone, the time required for de-esterification to occur contributes to a longer T half-life.

Oral dosages of the present invention can be taken by a patient in need of testosterone therapy once every about twelve hours to maintain desirable levels of serum testosterone. In a more preferred embodiment, oral dosages are taken by a patient in need of testosterone therapy once every about twenty four hours. In general, "desirable" testosterone levels are those levels found in a human subject characterized as not having testosterone deficiency.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

We claim:

1. A oral pharmaceutical composition comprising:
   a. a hypolipidemic agent that is a peroxisome proliferator activating receptor (PPAR) agonist; and
   b. 18 to 22 percent by weight of solubilized testosterone undecanoate, solubilized in a carrier comprising
      i. 15 to 17 percent by weight of hydrophilic surfactant;
      ii. 50 to 55 percent by weight of lipophilic surfactant; and
      iii. 10-15 percent by weight of a mixture of borage oil and peppermint oil.

2. The pharmaceutical product of claim 1, wherein said PPAR agonist is a pan-PPAR agonist.

3. The pharmaceutical product of claim 1, wherein said PPAR agonist is a selective PPARδ agonist.

4. The pharmaceutical product of claim 1, wherein said PPAR agonist is a selective PPARα agonist.

5. The pharmaceutical product of claim 4, wherein said selective PPARα agonist is selected from: bezafibrate, ciprofibrate, clofibrate, fenofibrate, and gemfibrozil.

6. The pharmaceutical product of claim 1, wherein said hypolipidemic agent and said testosterone ester are combined in the same pharmaceutical composition.

7. The pharmaceutical product of claim 6 wherein said pharmaceutical composition is a liquid- or semi-solid filled capsule, a powder-filled capsule, or a tablet.

8. A method of treating testosterone deficiency or its symptoms comprising orally administering to an individual suffering from testosterone deficiency or its symptoms an effective amount of a pharmaceutical product of claim 1.

9. The method of claim 8 in which said one or more pharmaceutical compositions are administered once daily.

10. The method of claim 8 in which said one or more pharmaceutical compositions are administered twice daily.

11. The method of claim 8 which gives rise to a testosterone $C_{max}$ value in said individual falling in the range of about 900 to 1100 ng/dL.

* * * * *